(12) United States Patent
Kwant et al.

(10) Patent No.: US 10,370,407 B2
(45) Date of Patent: Aug. 6, 2019

(54) AFFINITY-ASSISTED PROTEIN MODIFICATION AND RECYCLING

(71) Applicant: The Regents Of The University Of California, Oakland, CA (US)

(72) Inventors: Richard L. Kwant, Oakland, CA (US); Matthew B. Francis, Berkeley, CA (US); Christian B. Rosen, Berkeley, CA (US); Meera Rao, San Francisco, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 0 days.

(21) Appl. No.: 15/545,459

(22) PCT Filed: Jan. 21, 2016

(86) PCT No.: PCT/US2016/014354
§ 371 (c)(1),
(2) Date: Jul. 21, 2017

(87) PCT Pub. No.: WO2016/118770
PCT Pub. Date: Jul. 28, 2016

(65) Prior Publication Data
US 2018/0148472 A1    May 31, 2018

Related U.S. Application Data

(60) Provisional application No. 62/105,937, filed on Jan. 21, 2015, provisional application No. 62/277,763, filed on Jan. 12, 2016, provisional application No. 62/277,767, filed on Jan. 12, 2016.

(51) Int. Cl.
| | |
|---|---|
| *C07K 1/107* | (2006.01) |
| *C07K 1/13* | (2006.01) |
| *C08B 37/16* | (2006.01) |
| *C08H 1/00* | (2006.01) |

(52) U.S. Cl.
CPC ............ *C07K 1/1077* (2013.01); *C07K 1/13* (2013.01); *C08B 37/0012* (2013.01); *C08B 37/0015* (2013.01); *C08H 1/00* (2013.01)

(58) Field of Classification Search
None
See application file for complete search history.

(56) References Cited

FOREIGN PATENT DOCUMENTS

FR       2522656 A1 * 9/1983    ........... C07K 5/1005

OTHER PUBLICATIONS

Chen, Chang-Sheng et al, "Photoswitched self assembly of a gemini alpha helical peptide into supramolecular architectures." Nanoscale (2013) 5 p. 6270-6274.*
Del Valle, E. M. Martin, "Cyclodextrins and their uses: a review." Process Biochemistry 2004) 39 p. 1033-1046.*
León-Rodríguez, Luis M. De and Kovac, Zoltan; "The synthesis and chelation chemistry of dota peptide conjugates." Bioconjugate Chem. (2008) 19(2) p. 391-402.*
Liu, Hongcheng and May, Kimberly; "Disulfide bond structures of igg molecules." mAbs (2012) 4(1) p. 17-23.*
Bongini, Lorenzo et al, "A dynamic study of antibody antigen encounter reactions." Phys. Biol. (2007) 4 p. 172-180.*
Machine translation of Diaz et al, Fr 2522656.*
Strack, Martin et al, "Silyl based alkyne modifying linker for the preparation of c-terminal acetylene derivatized protected peptides." J. Org. Chem. (2012) 77 p. 9954-9958.*
Uryga-Polowy, Vivane et al, "Resin bound aminofluorescein for c-terminal labeling of peptides: high affinity polarization probes binding to polyproline specific gyf domains." ChemBioChem (2008) 9 p. 2452-2462.*
Koglin, Norman et al, "Facile and selective nanoscale labeling of peptides in solution by using photolabile protecting groups." J. Med.Chem. (2003) 46 p. 4369-4372.*
Smolková-Keulemansová, Eva, "Cyclodextrins in chromatography and isotachophoresis." from Proceedings of the Fourth International Symposium on Cyclodextrins, O. Huber and J. Szejtli, eds (1988) p. 451-463.*

* cited by examiner

*Primary Examiner* — Fred H Reynolds
(74) *Attorney, Agent, or Firm* — Mintz, Levin, Cohn, Ferris, Glovsky and Popeo, P.C.

(57) ABSTRACT

Methods for preparing a protein conjugate having a defined number of conjugate groups are provided. The method includes: forming a mixture containing a macrocyclic matrix material and a plurality of proteins; eluting the proteins to obtain a first separated protein fraction and a second separated protein fraction, wherein substantially all of the proteins in the first separated protein fraction have the same number of handle moieties; contacting the handle moieties with a conversion reagent under conditions sufficient to convert the handle moieties in the first separated protein fraction to reactive moieties; and contacting the reactive moieties with a conjugation reagent under conditions sufficient to form a plurality of protein conjugates, wherein substantially all of the protein conjugates in the plurality have the same number of conjugate groups. Methods also include recovering enzymes and other proteins from mixtures for isolation and/or reuse of the enzymes and proteins.

14 Claims, 28 Drawing Sheets
Specification includes a Sequence Listing.

Alkyne-terminated resin

β-cyclodextrin-terminated resin

4

5

6

FIG. 14 – continued
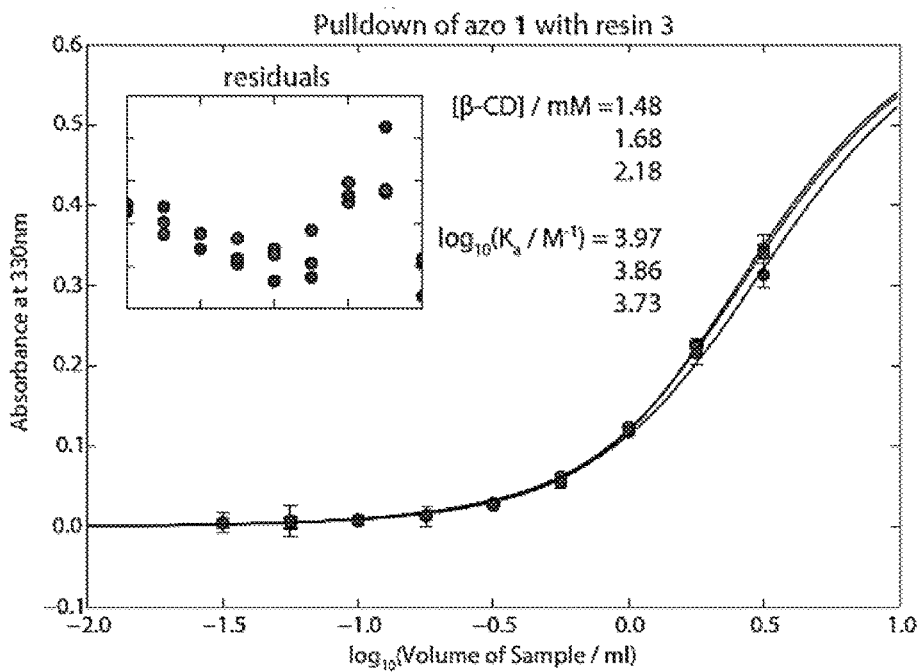
FIG. 15
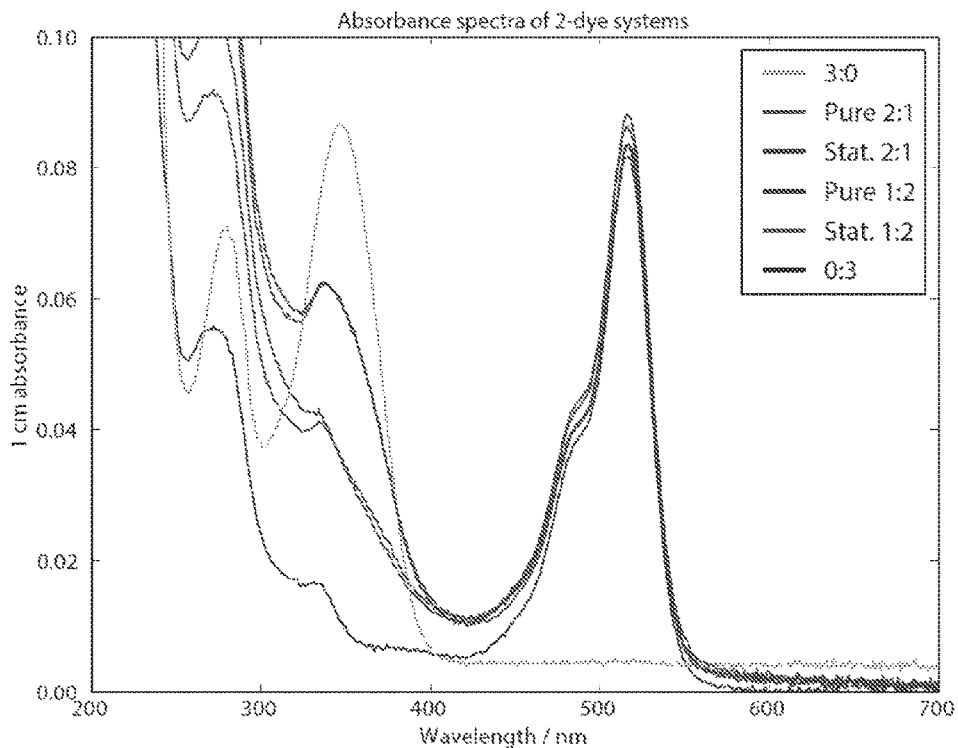

RNase A-lithocholic acid conjugate

AFFINITY-ASSISTED PROTEIN MODIFICATION AND RECYCLING

CROSS-REFERENCES TO RELATED APPLICATIONS

This present application is the U.S. National Stage Entry under § 371 of International Application No. PCT/US2016/014354, filed Jan. 21, 2016, which claims priority to U.S. Provisional Patent Appl. Nos. 62/105,937, filed Jan. 21, 2016; 62/277,763 filed on Jan. 12, 2016; and 62/277,767, filed on Jan. 12, 2016 which applications are incorporated herein by reference in their entirety.

STATEMENT AS TO RIGHTS TO INVENTIONS MADE UNDER FEDERALLY SPONSORED RESEARCH AND DEVELOPMENT

This invention was made with Government support under Grant No. DE-AC02-05CH11231, awarded by the U.S. Department of Energy, and Grant No. FA9550-11-C-0028, awarded by the U.S. Department of Defense. The Government has certain rights in this invention.

SEQUENCE LISTING

[0002.1] The content of the following submission on ASCII text file is incorporated herein by reference in its entirety: a computer readable form (CRF) of the Sequence Listing (file name: 052565-506N01US_Sequence_Listing_ST25.txt, date created: Feb. 20, 2019, size: 1,342 bytes).

BACKGROUND OF THE INVENTION

The importance of protein bioconjugates has grown as they have found widespread use as therapeutics, chemical sensors, scaffolds for new materials, and tools for basic research. The construction of such materials depends on the ability to modify proteins selectively and quantitatively, producing a continual demand for new strategies. While myriad methods for protein modification exist, it remains difficult to modify native proteins in a well-defined manner. This problem is particularly apparent with one of the most common methods for protein modification: acylation of lysine residues with NHS-esters. This modification strategy results in inseparable statistical mixtures of proteins with differing levels of modification. It is possible to circumvent this limitation by using chemistries that target rare (engineered cysteines, tyrosines), unique (N-terminus, C-terminus), or introduced (small molecule tags, peptide tags) moieties on proteins, but the applicability of these methods varies on a case-by-case basis.

This problem has motivated much of current research into strategies for site-selective protein modification, and it has slowed the development of many protein-based materials. For example, it is known that the drug loading on antibody-drug conjugates affects their efficacy, yet traditional methods like lysine acylation often result in over-modification. It remains challenging to construct antibody-drug conjugates with controlled levels and locations of drug loading. This problem has been encountered during the construction of mimics of light harvesting arrays. Efficient light-harvesting systems require the precise arrangement of multiple unique dyes. These systems have been successfully approximated by using viral coat proteins to template pairs of dyes that participate in Förster resonance energy transfer (FRET). However, because the modification site on each protein monomer is chemically identical, it is impossible to control the exact ratio of acceptors to donors on each protein assembly in a precise manner. As a result, these efforts have been limited to the study of statistical mixtures of light-harvesting mimics with different dye compositions.

While the development of site-selective bioconjugation reactions certainly has a role to play in addressing these problems, one missing piece is a general separation technique that can distinguish between bioconjugates with different levels and sites of modification. Such a technique would be akin to silica gel chromatography, which is used frequently for small molecule synthesis.

Those who modify proteins seldom use chromatography to separate proteins based on their degree of modification because most available methods-including gel filtration, ion-exchange chromatography, and hydrophobic interaction chromatography-poorly discern the small differences in polarity, charge, and size brought about by modification with small molecules. In contrast, affinity chromatography has the unique ability to select for proteins bearing small, specific chemical groups. This technique has been used in specific instances to purify proteins modified with certain groups like fluorescent dyes or prenyl groups. However, it has not been explored as a general method for the isolation of homogeneous bioconjugates that are modified with arbitrary chemical moieties. There is a need for general methods for separation of proteins based on degree of modification and improved methods for preparation of well-defined bioconjugates. The present invention meets these and other needs.

BRIEF SUMMARY OF THE INVENTION

In one aspect, the invention provides a method for preparing a protein conjugate having a defined number of conjugate groups. The method includes:
i) forming a mixture containing a macrocyclic matrix material and a plurality of proteins, wherein:
each protein in a first population of proteins in the plurality has a first number of handle moieties,
each protein in a second population of proteins in the plurality has a second number of handle moieties, and
the mixture is formed under conditions sufficient to bind the modified proteins to the macrocyclic matrix material;
ii) eluting the proteins from the macrocyclic matrix material to obtain a first separated protein fraction and a second separated protein fraction, wherein:
substantially all of the proteins in the first separated protein fraction have the first number of handle moieties, and
substantially all of the proteins in the second separated protein fraction have the second number of handle moieties;
iii) contacting the handle moieties with a conversion reagent under conditions sufficient to convert the handle moieties in the first separated protein fraction to reactive moieties; and
iv) contacting the reactive moieties with a conjugation reagent under conditions sufficient to form a plurality of protein conjugates, wherein substantially all of the protein conjugates in the plurality have the same number of conjugate groups;
thereby preparing the protein conjugate.

In some embodiments, the handle moiety includes an azo group. In some embodiments, the macrocyclic matrix material includes a plurality of cyclodextrin groups.

In another aspect, the invention provides a method for conducting an enzymatic reaction. The method includes:
   a) forming a reaction mixture containing an enzyme and an enzyme substrate, wherein the enzyme has a prosthetic guest moiety, under conditions sufficient to convert the enzyme substrate to a product;
   b) adding a matrix material containing a macrocyclic host moiety to the reaction mixture under conditions sufficient to form an enzyme-matrix host-guest complex; and
   c) recovering the enzyme-matrix host-guest complex from the reaction mixture;
   thereby conducting the enzymatic reaction.

In some embodiments, the method further includes eluting the enzyme from the enzyme-matrix host-guest complex and reusing the enzyme.

In a related aspect, the invention provides a method for isolating a protein. The method includes:
   i) forming a mixture containing a matrix material and a protein conjugate, wherein:
   the matrix material contains a macrocyclic host moiety,
   the protein conjugate has a prosthetic guest moiety, and
   the mixture is formed under conditions sufficient to form a protein-matrix host-guest complex; and
   ii) recovering the protein-matrix host-guest complex from the mixture;
   thereby isolating the protein.

In some embodiments, the prosthetic guest moiety includes a bile acid group. In some embodiments, the macrocyclic host moiety includes a β-cyclodextrin group.

BRIEF DESCRIPTION OF THE DRAWINGS

FIG. 15 shows absorbance spectra of protein samples described herein.

DETAILED DESCRIPTION OF THE INVENTION

I. General

Figure 1A:
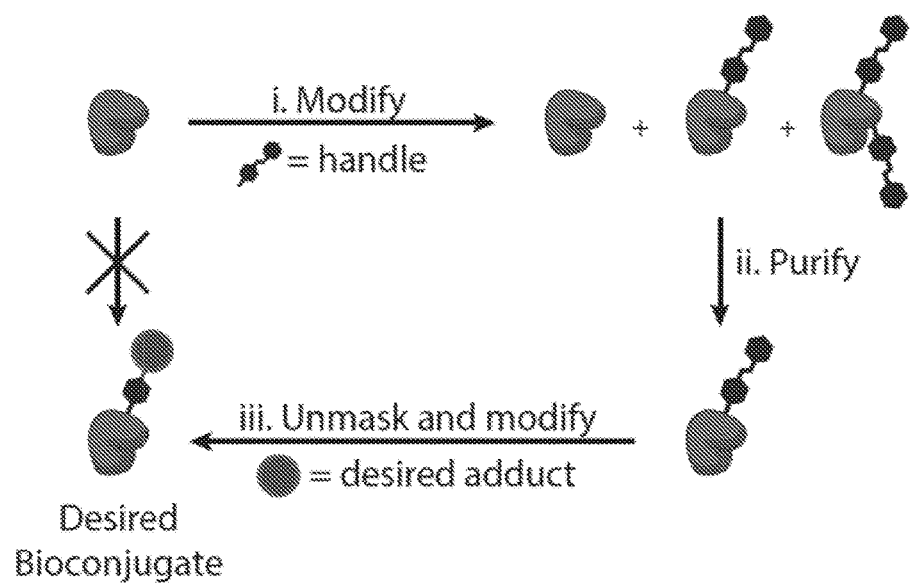
FIG. 1A shows a proposed method for chromatography-assisted protein modification. The protein is first modified with a handle (step i). The protein with the desired level of modification is isolated based on an affinity interaction with this handle (step ii). Innate reactivity in the handle is unmasked, and the handle is modified with a desired bioconjugate (step iii).

The present invention provides a method for the construction of well-defined protein bioconjugates through the use of affinity chromatography-assisted oxidative coupling. As described herein, this method has been used to isolate pure samples of protein modified a particular number of times, such as the protein trimer Mth1491 modified with specific numbers of fluorophores for constructing protein-templated FRET pairs. Such FRET pairs are challenging to make using traditional approaches, and the well-defined compositions prepared according to the method of the invention exhibit different behavior from statistically prepared light harvesting scaffolds. The method can also be applied generally to the modification of other proteins. The methods described herein are of significant synthetic utility in making protein-based materials of increasing complexity. In addition, methods for efficient recovery and reuse of modified proteins (e.g., modified enzymes) are provided.

II. Definitions

As used herein, the terms "protein," "peptide," and "polypeptide" are used interchangeably herein to refer to a polymer of amino acid residues. All three terms apply to naturally occurring amino acid polymers and non-natural amino acid polymers, as well as to amino acid polymers in which one (or more) amino acid residue is an artificial chemical mimetic of a corresponding naturally occurring amino acid. As used herein, the terms encompass amino acid chains of any length, including full-length proteins, wherein the amino acid residues are linked by covalent peptide bonds.

The term "amino acid" refers to any monomeric unit that can be incorporated into a peptide, polypeptide, or protein. Amino acids include naturally-occurring α-amino acids and their stereoisomers, as well as unnatural (non-naturally occurring) amino acids and their stereoisomers. "Stereoisomers" of a given amino acid refer to isomers having the same molecular formula and intramolecular bonds but different three-dimensional arrangements of bonds and atoms (e.g., an L-amino acid and the corresponding D-amino acid).

Naturally-occurring amino acids are those encoded by the genetic code, as well as those amino acids that are later modified, e.g., hydroxyproline, γ-carboxyglutamate, and O-phosphoserine. Naturally-occurring α-amino acids include, without limitation, alanine (Ala), cysteine (Cys), aspartic acid (Asp), glutamic acid (Glu), phenylalanine (Phe), glycine (Gly), histidine (His), isoleucine (Ile), arginine (Arg), lysine (Lys), leucine (Leu), methionine (Met), asparagine (Asn), proline (Pro), glutamine (Gln), serine (Ser), threonine (Thr), valine (Val), tryptophan (Trp), tyrosine (Tyr), and combinations thereof. Stereoisomers of a naturally-occurring α-amino acids include, without limitation, D-alanine (D-Ala), D-cysteine (D-Cys), D-aspartic acid (D-Asp), D-glutamic acid (D-Glu), D-phenylalanine (D-Phe), D-histidine (D-His), D-isoleucine (D-Ile), D-arginine (D-Arg), D-lysine (D-Lys), D-leucine (D-Leu), D-methionine (D-Met), D-asparagine (D-Asn), D-proline (D-Pro), D-glutamine (D-Gln), D-serine (D-Ser), D-threonine (D-Thr), D-valine (D-Val), D-tryptophan (D-Trp), D-tyrosine (D-Tyr), and combinations thereof.

Unnatural (non-naturally occurring) amino acids include, without limitation, amino acid analogs, amino acid mimetics, synthetic amino acids, N-substituted glycines, and N-methyl amino acids in either the L- or D-configuration that function in a manner similar to the naturally-occurring amino acids. For example, "amino acid analogs" can be unnatural amino acids that have the same basic chemical structure as naturally-occurring amino acids (i.e., a carbon that is bonded to a hydrogen, a carboxyl group, an amino group) but have modified side-chain groups or modified peptide backbones, e.g., homoserine, norleucine, methionine sulfoxide, methionine methyl sulfonium. "Amino acid mimetics" refer to chemical compounds that have a structure that is different from the general chemical structure of an amino acid, but that functions in a manner similar to a naturally-occurring amino acid. Amino acids may be referred to herein by either the commonly known three letter symbols or by the one-letter symbols recommended by the IUPAC-IUB Biochemical Nomenclature Commission.

As used herein, the term "signaling protein" refers to a protein that is part of a cellular signal transduction pathway. Examples of signaling pathways include, but are not limited to, MAP kinase signaling, PI3K/Akt signaling, protein kinase C signaling, and phospholipase signaling. Examples of signaling proteins include, but are not limited to, kinases, phosphatases, phosphodiesterases, nucleotide cyclases, G-proteins, and channel proteins.

As used herein, the term "structural protein" refers to a protein that provides structural support to cells and other biological structures. Structural proteins often assemble to form structures such as filaments, cables, and sheets to provide biomechanical properties necessary for maintenance of cell shape and function. Non-limiting examples of structural proteins include actin, tubulin, myosin, keratin, fibroin, collagen, elastin, and proteoglycans.

As used herein, the term "transport protein" refers to a polypeptide which functions to convey molecules into (e.g., uptake proteins) and out of (e.g., efflux proteins) a cell, as well as transportation of molecules intracellularly (e.g., translocation proteins) and other related transport activity. Examples of transport proteins include, but are not limited to, annexins, clathrin, caveolins, SNARE proteins, glucose transporter proteins, and aquaporins.

As used herein, the terms "targeting protein" and "targeting polypeptide" refer to a protein that can selectively interact with a target feature such as a cellular receptor or another cell surface protein. Examples of targeting proteins include, but are not limited to, antibodies, antibody fragments such as synthetic $F_{ab}$'s, and aptamers.

As used herein, the term "hormone protein" refers to a protein that functions as an extracellular signal to elicit a response from a target cell or tissue. Examples of hormone proteins include, but are not limited to, insulin, luteinizing hormone, and platelet-derived growth factor.

As used herein, the term "enzyme" refers to a protein that catalyzes the transformation of a starting material to a reaction intermediate or a reaction product. The catalytic function of an enzyme is referred to the enzyme's "activity," and enzymes are typically classified according to the type of catalytic functions they carry out, e.g., hydrolysis of peptide bonds in the case of proteases. The term "enzymatic reaction" refers to an enzyme-catalyzed process (e.g., a single step process or multi-step process) in which a starting material is converted to a reaction intermediate or a reaction product. The term "enzyme substrate" refers to a molecule or other substance upon which the enzyme performs its catalytic activity to generate the intermediate or product.

As used herein, the term "protein conjugate" refers to a protein having one or more prosthetic conjugate groups (e.g., handle moieties and reactive moieties as described below) covalently bonded to the protein. By "prosthetic," it is meant that the conjugate groups are not present in the protein following expression of the protein in an organism from which the protein is derived (i.e., after translation and/or post-translational modification in the organism or a heterologous expression system). Rather, prosthetic conjugate groups are appended to the protein via reaction with one or more chemical reactants so as to modify the protein—i.e., to covalently bond the conjugate group to the protein. Conjugate groups can be covalently bonded to the protein at one or more amino acid residue sidechains (e.g., at a terminal amino group in a lysine sidechain or a thiol group in a cysteine sidechain), at one or positions in the peptide backbone of the protein (e.g., at the N-terminus or C-terminus of the protein), or at other locations in the protein (e.g., in a sugar moiety of a glycosylated protein).

As used herein, the term "macrocyclic matrix material" refers to a material containing an insoluble support and a plurality of macrocyclic host moieties. By "insoluble," it is meant that the matrix material does not dissolve when contacted with liquid media of the sort typically used for handling proteins and other biomolecules (e.g., aqueous buffers and aqueous mixtures containing organic co-solvents). Examples of support materials include, but are not limited to, crosslinked polysaccharides; porous silica gels; silica and mineral oxides modified with hydrogel-forming polymers; crosslinked polyacrylamides (e.g., bis-acrylamide copolymers and acrylamide-poly(ethylene glycol) copolymers); and monolithic materials. A "monolith" refers to a porous, three-dimensional material having a continuous interconnected pore structure in a single body. The term monolith is meant to be distinguished from a collection of individual particles packed into a bed formation.

As used herein, the term "crosslinked polysaccharide" refers to a beaded resin formed from carbohydrate polymers (e.g., dextrose, agarose, and combinations thereof) that are rendered insoluble in liquid media (e.g., aqueous solutions and aqueous mixtures containing organic co-solvents) by reaction with crosslinking reagents such as epihalohydrin, bis-epoxides, divinyl sulfone, and the like. A number of crosslinked polysaccharides are commercially available under tradenames including SEPHADEX, SEPHAROSE, SEPHACRYL (GE Healthcare Life Sciences), and others.

As used herein, the term "host-guest complex" refers to a supramolecular assembly containing a macrocylic host species and a guest species bound together via non-covalent interactions (e.g., hydrophobic forces, electrostatic forces, van der Waals forces, hydrogen bonding). "Macrocyclic" species are those having a chemical structures that include at least one ring or cycle formed by nine or more covalently bonded atoms (e.g., cyclodextrins, cucurbiturils, and the like, as described herein). Macrocylic hosts are typically characterized by a cavity within which at least a portion of guest moiety resides. Van der Waals forces and other non-covalent interactions can stabilize the complex such that the guest is "captured" from an external environment (e.g., an aqueous solution).

As used herein, the term "cyclodextrin" refers to a compound having 1,4-linked glycopyranose residues bonded together to form a macrocyclic structure. Cyclodextrins include α-cyclodextrin (α-CD), β-cyclodextrins (β-CD), and γ-cyclodextrins (γ-CD), having six, seven, and eight glycopyranose residues, respectively, which can be produced from enzymatic degradation of starch. Cyclodextrins are characterized by a truncated cone morphology with a hydrophobic cavity at the center and a hydrophilic periphery having primary and secondary hydroxyl groups. Cyclodextrins can act as host moieties for a wide variety of chemical species (guests) to form host-guest complexes.

As used herein, the term "cucurbituril" refers to a cyclic oligomer formed by linking glycoluril subunits via methylene bridges. Cucurbit[n]urils (having "n" glycoluril subunits) are characterized a rigid central cavity with two portals to the central cavity. These portals are typically surrounded by polar groups and are typically narrower in diameter than the internal diameter of the central cavity. Substituted and unsubstituted cucurbiturils are described, for example, in U.S. Pat. Nos. 6,365,734; 6,869,466; and 7,501,523.

As used herein, the term "guest moiety" refers to a chemical structure that can form non-covalent interactions with a host moiety. The non-covalent interactions can be sufficient to capture the guest moiety from an external environment. Examples of guest moieties include, but are not limited to, bile acids, adamantane and derivatives thereof, azobenzene groups, ferrocene groups, p-xylylene-diammonium groups, pyridinium and bi-pyridinium groups, and triazole groups.

In certain instances, the guest moiety will contain a functional "handle" that be converted into a reactive group for further chemical modification. Examples of handle moieties include, but are not limited to, azo groups (including aromatic azo groups), disulfide groups, hydrazone groups, imine groups, and diol groups (including diols with hydroxyl groups on adjacent carbon atoms, referred to a vicinal diols). The term "reactive moiety" refers to a functional group capable of reacting with one or more reagents to form a protein conjugate. Examples of reactive moieties include, but are not limited to, amines (including aromatic amines such as anilines), thiols, aldehydes, and ketones.

As used herein, the term "salt" refers to acid or base salts of the compounds used in the methods of the present invention. Non-toxic (i.e., pharmaceutically acceptable salts) are particularly preferred for use in various embodiments of the invention. Illustrative examples of pharmaceutically acceptable salts are mineral acid (hydrochloric acid, hydrobromic acid, phosphoric acid, and the like) salts, organic acid (acetic acid, propionic acid, glutamic acid, citric acid and the like) salts, quaternary ammonium (methyl iodide, ethyl iodide, and the like) salts. Additional information on suitable salts can be found in *Remington: The Science and Practice of Pharmacy*, 21$^{st}$ Edition, 2005, Hendrickson, Ed., Lippincott, Williams & Wilkins, which is incorporated herein by reference.

As used herein, the term "linking moiety" refers to a functional group that covalently bonds two or more moieties in a compound or material. For example, the linking moiety can serve to covalently bond a conjugate group (e.g., a handle moiety) to a protein in a protein conjugate or to covalently bond a macrocyclic host moiety (e.g., a cyclodextrin) to a support in a matrix material. Useful bonds for connecting linking moieties to proteins and other materials include, but are not limited to, amides, amines, esters, carbamates, ureas, thioethers, thiocarbamates, thiocarbonates, and thioureas. A "divalent" linking moiety contains two points of attachment for linking two functional groups; polyvalent linking moieties can have additional points of attachment for linking further functional groups. For example, divalent linking moieties include divalent polymer moieties such as divalent poly(ethylene glycol), divalent poly(propylene glycol), and divalent poly(vinyl alcohol).

As used herein, the term "alkyl" refers to a straight or branched, saturated, aliphatic radical having the number of carbon atoms indicated. Alkyl can include any number of carbons, such as $C_{1-2}$, $C_{1-3}$, $C_{1-4}$, $C_{1-5}$, $C_{1-6}$, $C_{1-7}$, $C_{1-8}$, $C_{1-9}$, $C_{1-10}$, $C_{2-3}$, $C_{2-4}$, $C_{2-5}$, $C_{2-6}$, $C_{3-4}$, $C_{3-5}$, $C_{3-6}$, $C_{4-5}$, $C_{4-6}$ and $C_{5-6}$. For example, $C_{1-6}$ alkyl includes, but is not limited to, methyl, ethyl, propyl, isopropyl, butyl, isobutyl, sec-butyl, tert-butyl, pentyl, isopentyl, hexyl, etc. Alkyl can also refer to alkyl groups having up to 30 carbons atoms, such as, but not limited to heptyl, octyl, nonyl, decyl, etc. Alkyl groups can be substituted or unsubstituted. "Substituted alkyl" groups can be substituted with one or more groups selected from halo, hydroxy, amino, oxo (=O), alkylamino, amido, acyl, nitro, cyano, and alkoxy.

As used herein, the term "carbocycle" refers to a saturated or partially unsaturated, monocyclic, fused bicyclic, or bridged polycyclic ring assembly containing from 3 to 12 ring atoms, or the number of atoms indicated. Carbocycles can include any number of carbons, such as $C_{3-6}$, $C_{4-6}$, $C_{5-6}$, $C_{3-8}$, $C_{4-8}$, $C_{5-8}$, $C_{6-8}$, $C_{3-9}$, $C_{3-10}$, $C_{3-11}$, and $C_{3-12}$. Saturated monocyclic carbocyclic rings include, for example, cyclopropyl, cyclobutyl, cyclopentyl, cyclohexyl, and cyclooctyl. Saturated bicyclic and polycyclic carbocyclic rings include, for example, norbornane, [2.2.2] bicyclooctane, decahydronaphthalene and adamantane. Carbocyclic groups can also be partially unsaturated, having one or more double or triple bonds in the ring. Representative carbocyclic groups that are partially unsaturated include, but are not limited to, cyclobutene, cyclopentene, cyclohexene, cyclohexadiene (1,3- and 1,4-isomers), cycloheptene, cycloheptadiene, cyclooctene, cyclooctadiene (1,3-, 1,4- and 1,5-isomers), norbornene, and norbornadiene. A "divalent" carbocycle refers to a carbocyclic group having two points of attachment for covalently linking two moieties in a molecule or material.

As used herein, the term "heterocycle" refers to heterocycloalkyl groups and heteroaryl groups. "Heteroaryl," by itself or as part of another substituent, refers to a monocyclic or fused bicyclic or tricyclic aromatic ring assembly containing 5 to 16 ring atoms, where from 1 to 5 of the ring atoms are a heteroatom such as N, O or S. Additional heteroatoms can also be useful, including, but not limited to, B, Al, Si and P. The heteroatoms can be oxidized to form moieties such as, but not limited to, —S(O)— and —S(O)$_2$—. Heteroaryl groups can include any number of ring atoms, such as 3 to 6, 4 to 6, 5 to 6, 3 to 8, 4 to 8, 5 to 8, 6 to 8, 3 to 9, 3 to 10, 3 to 11, or 3 to 12 ring members. Any suitable number of heteroatoms can be included in the heteroaryl groups, such as 1, 2, 3, 4, or 5, or 1 to 2, 1 to 3, 1 to 4, 1 to 5, 2 to 3, 2 to 4, 2 to 5, 3 to 4, or 3 to 5. The heteroaryl group can include groups such as pyrrole, pyridine, imidazole, pyrazole, triazole, tetrazole, pyrazine, pyrimidine, pyridazine, triazine (1,2,3-, 1,2,4- and 1,3,5-isomers), thiophene, furan, thiazole, isothiazole, oxazole, and isoxazole. The heteroaryl groups can also be fused to aromatic ring systems, such as a phenyl ring, to form members including, but not limited to, benzopyrroles such as indole and isoindole, benzopyridines such as quinoline and isoquinoline, benzopyrazine (quinoxaline), benzopyrimidine (quinazoline), benzopyridazines such as phthalazine and cinnoline, benzothiophene, and benzofuran. Other heteroaryl groups include heteroaryl rings linked by a bond, such as bipyridine. Heteroaryl groups can be substituted or unsubstituted. "Substituted heteroaryl" groups can be substituted with one or more groups selected from halo, hydroxy, amino, alkylamino, amido, acyl, nitro, cyano, and alkoxy.

Heteroaryl groups can be linked via any position on the ring. For example, pyrrole includes 1-, 2- and 3-pyrrole, pyridine includes 2-, 3- and 4-pyridine, imidazole includes 1-, 2-, 4- and 5-imidazole, pyrazole includes 1-, 3-, 4- and 5-pyrazole, triazole includes 1-, 4- and 5-triazole, tetrazole includes 1- and 5-tetrazole, pyrimidine includes 2-, 4-, 5- and 6-pyrimidine, pyridazine includes 3- and 4-pyridazine, 1,2,3-triazine includes 4- and 5-triazine, 1,2,4-triazine includes 3-, 5- and 6-triazine, 1,3,5-triazine includes 2-triazine, thiophene includes 2- and 3-thiophene, furan includes 2- and 3-furan, thiazole includes 2-, 4- and 5-thiazole, isothiazole includes 3-, 4- and 5-isothiazole, oxazole includes 2-, 4- and 5-oxazole, isoxazole includes 3-, 4- and 5-isoxazole, indole includes 1-, 2- and 3-indole, isoindole includes 1- and 2-isoindole, quinoline includes 2-, 3- and 4-quinoline, isoquinoline includes 1-, 3- and 4-isoquinoline, quinazoline includes 2- and 4-quinoazoline, cinnoline includes 3- and 4-cinnoline, benzothiophene includes 2- and 3-benzothiophene, and benzofuran includes 2- and 3-benzofuran.

"Heterocyclyl," by itself or as part of another substituent, refers to a saturated ring system having from 3 to 12 ring members and from 1 to 4 heteroatoms of N, O and S. Additional heteroatoms can also be useful, including, but not limited to, B, Al, Si and P. The heteroatoms can be oxidized to form moieties such as, but not limited to, —S(O)— and —S(O)$_2$—. Heterocyclyl groups can include any number of ring atoms, such as, 3 to 6, 4 to 6, 5 to 6, 3 to 8, 4 to 8, 5 to 8, 6 to 8, 3 to 9, 3 to 10, 3 to 11, or 3 to 12 ring members. Any suitable number of heteroatoms can be included in the heterocyclyl groups, such as 1, 2, 3, or 4, or 1 to 2, 1 to 3, 1 to 4, 2 to 3, 2 to 4, or 3 to 4. The heterocyclyl group can include groups such as aziridine, azetidine, pyrrolidine, piperidine, azepane, azocane, quinuclidine, pyrazolidine, imidazolidine, piperazine (1,2-, 1,3- and 1,4-isomers), oxirane, oxetane, tetrahydrofuran, oxane (tetrahydropyran), oxepane, thiirane, thietane, thiolane (tetrahydrothiophene), thiane (tetrahydrothiopyran), oxazolidine, isoxazolidine, thiazolidine, isothiazolidine, dioxolane, dithiolane, morpholine, thiomorpholine, dioxane, or dithiane. The heterocyclyl groups can also be fused to aromatic or non-aromatic ring systems to form members including, but not limited to, indoline. Heterocyclyl groups can be unsubstituted or substituted. "Substituted heterocyclyl" groups can be substituted with one or more groups selected from halo, hydroxy, amino, oxo (=O), alkylamino, amido, acyl, nitro, cyano, and alkoxy.

Heterocyclyl groups can be linked via any position on the ring. For example, aziridine can be 1- or 2-aziridine, azetidine can be 1- or 2-azetidine, pyrrolidine can be 1-, 2- or 3-pyrrolidine, piperidine can be 1-, 2-, 3- or 4-piperidine, pyrazolidine can be 1-, 2-, 3-, or 4-pyrazolidine, imidazolidine can be 1-, 2-, 3- or 4-imidazolidine, piperazine can be 1-, 2-, 3- or 4-piperazine, tetrahydrofuran can be 1- or 2-tetrahydrofuran, oxazolidine can be 2-, 3-, 4- or 5-oxazolidine, isoxazolidine can be 2-, 3-, 4- or 5-isoxazolidine, thiazolidine can be 2-, 3-, 4- or 5-thiazolidine, isothiazolidine can be 2-, 3-, 4- or 5-isothiazolidine, and morpholine can be 2-, 3- or 4-morpholine.

As used herein, the terms "halo" and "halogen," by themselves or as part of another substituent, refer to a fluorine, chlorine, bromine, or iodine atom.

As used herein, the term "carbonyl," by itself or as part of another substituent, refers to —C(O)—, i.e., a carbon atom double-bonded to oxygen and bound to two other groups in the moiety having the carbonyl.

As used herein, the term "amino" refers to a moiety —NR$_3$, wherein each R group is H or alkyl. An amino moiety can be ionized to form the corresponding ammonium cation.

As used herein, the term "hydroxy" refers to the moiety —OH.

As used herein, the term "cyano" refers to a carbon atom triple-bonded to a nitrogen atom (i.e., the moiety —C≡N).

As used herein, the term "carboxy" refers to the moiety —C(O)OH. A carboxy moiety can be ionized to form the corresponding carboxylate anion.

As used herein, the term "amido" refers to a moiety —NRC(O)R or —C(O)NR$_2$, wherein each R group is H or alkyl.

As used herein, the term "nitro" refers to the moiety —NO$_2$.

As used herein, the term "oxo" refers to an oxygen atom that is double-bonded to a compound (i.e., O=).

As used herein, the terms "bind" and "binding" refer to the non-covalent interaction between a pair of partner molecules or portions thereof (e.g., a host moiety and guest moiety) that exhibit mutual affinity or binding capacity. Binding can occur such that the partners are able to interact with each other to a substantially higher degree than with other, similar substances. This specificity can result in stable complexes (e.g., host-guest complexes) that remain bound during handling steps such as chromatography, centrifugation, filtration, and other techniques typically used for separations and other processes. The terms "elute" and "eluting" refer to the disruption of non-covalent interactions between binding partners (e.g., a host moiety and guest moiety) such that the partners become unbound from one another. The disruption can be effected via introduction of a competitive binding species, or via a change in environmental conditions (e.g., ionic strength, pH, or other conditions).

As used herein, the term "forming a mixture" refers to the process of bringing into contact at least two distinct species such that they mix together and interact. "Forming a reaction mixture" and "contacting" refer to the process of bringing into contact at least two distinct species such that they mix together and can react, either modifying one of the initial reactants or forming a third, distinct, species, a product. It should be appreciated, however, the resulting reaction product can be produced directly from a reaction between the added reagents or from an intermediate from one or more of the added reagents which can be produced in the reaction mixture. "Conversion" and "converting" refer to a process including one or more steps wherein a species is transformed into a distinct product.

As used herein, the terms "separating," "isolating," and "recovering" refer to the process of removing at least a portion (i.e., a fraction) of a first substance from a mixture containing the first substance, a second substance, and other optional substances. Separation can be conducted such that the separated substance is substantially free of at least one of the other substances present in the original mixture. For example, when the separated first substance is substantially free of the second substance, it is meant that at least about 50% (e.g., 55, 60, 65, 70, 75, 80, 85, 90, 95, or 99% (w/w)) of the second substance is removed from the isolated first substance. A "separated protein fraction" refers to a mixture containing a protein and optional excipients (e.g., buffers, detergents, and the like), wherein the protein molecules in the fraction are substantially identical. By "substantially identical," is it meant that at least about 50% of the protein molecules (e.g., 55, 60, 65, 70, 75, 80, 85, 90, 95, or 99% (w/w)) have the same polypeptide sequence and the same level of modification with a handle moiety or other conjugate group.

As used herein, the term "conversion reagent" refers to a substance capable of reacting with a handle moiety on a protein to form a reactive moiety. Examples of conversion reagents include, but are not limited to, reducing agents and oxidizing agents. The term "conjugation reagent" refers to a substance capable of reacting with a reactive moiety on a protein to form a protein conjugate. Conjugation reagents can contain functional groups including, but not limited to, aminophenols, maleimides, iodoacetamides, and hydroxylamines.

As used herein, the term "oxidizing agent" refers to a reagent which can accept electrons from a substrate compound in an oxidation-reduction reaction. Electrons can be transferred from the substrate compound to the oxidizing agent in a process that includes addition of oxygen to the substrate compound or removal of hydrogen from the substrate compound. Examples of oxidizing agents include, but are not limited to, sodium periodate, cerium ammonium nitrate, and potassium ferricyanide.

The terms "about" and "around," as used herein to modify a numerical value, indicate a close range surrounding that explicit value. If "X" were the value, "about X" or "around X" would indicate a value from 0.8× to 1.2×, preferably a value from 0.9× to 1.1×, and, more preferably, a value from 0.95× to 1.05×. Any reference to "about X" or "around X" specifically indicates at least the values X, 0.95×, 0.96×, 0.97×, 0.98×, 0.99×, 1.01×, 1.02×, 1.03×, 1.04×, and 1.05×. Thus, "about X" and "around X" are intended to teach and provide written description support for a claim limitation of, e.g., "0.98×."

III. Chromatography Assisted Protein Modification

Figure 1B:
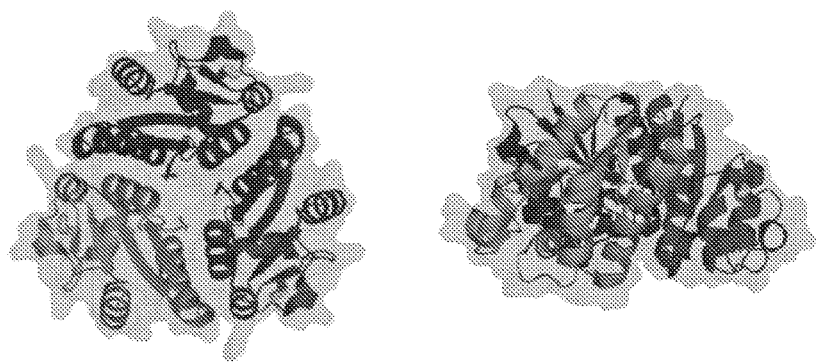
FIG. 1B shows top and side views of the thermostable Mth1491 trimer (PDB ID=1L1S). The protein is modified using the methods of the invention to afford a template for model light-harvesting systems.

Disclosed herein are general methods for creating well-defined protein conjugates through affinity chromatography-assisted bioconjugation reactions (e.g., oxidative coupling and other transformations). The methods include: (i) the modification of a protein with a specific chemical handle, such that proteins with varying number of handle moieties are produced, (ii) purification of modified proteins having a specific level of modification using host guest interactions between the handle moieties and a chromatography matrix, and (iii) subsequent synthetic elaboration of the handle to form the final bioconjugate (FIG. 1A). The first step can be accomplished using most existing chemistries for protein modification. In the second step, modified proteins are separated by a resin-bound affinity group according to their degree of modification and the chemical environment of the handle. This second step can be conducted using a fast protein liquid chromatography (FPLC) format. In the third step, an intrinsic reactivity in the handle is unmasked and the handle is quantitatively modified with a new functional group of choice to afford a well-defined bioconjugate. Use of the method for the construction of donor-acceptor systems with specific chromophore ratios templated by the protein homotrimer Mth1491 (FIG. 1B) is disclosed in greater detail below. These donor-acceptor systems provide for the generation of well-defined light harvesting systems for photophysical studies, which are applicable to improvement of light-driven production processes and development of photovoltaic device components.

Accordingly, a first aspect of the invention provides a method for preparing a protein conjugate having a defined number of conjugate groups. The method includes:
i) forming a mixture containing a macrocyclic matrix material and a plurality of proteins, wherein:
each protein in a first population of proteins in the plurality has a first number of handle moieties,
each protein in a second population of proteins in the plurality has a second number of handle moieties, and
the mixture is formed under conditions sufficient to bind the modified proteins to the macrocyclic matrix material;
ii) eluting the proteins from the macrocyclic matrix material to obtain a first separated protein fraction and a second separated protein fraction, wherein:
substantially all of the proteins in the first separated protein fraction have the first number of handle moieties, and
substantially all of the proteins in the second separated protein fraction have the second number of handle moieties;
iii) contacting the handle moieties with a conversion reagent under conditions sufficient to convert the handle moieties in the first separated protein fraction to reactive moieties; and
iv) contacting the reactive moieties with a conjugation reagent under conditions sufficient to form a plurality of protein conjugates, wherein substantially all of the protein conjugates in the plurality have the same number of conjugate groups; thereby preparing the protein conjugate.

Use of the term "defined," in connection with the number of conjugate groups present in a protein conjugate, means that protein conjugate has a desired number of conjugate groups suitable for particular purpose. In preparing a therapeutic conjugate such as an antibody-drug conjugate, for example, it may be advantageous or necessary to prepare a conjugate having a defined number of therapeutic groups—e.g., only one drug group covalently conjugated to the antibody, or only two drug groups covalently conjugated to the antibody. As another non-limiting example, it may be advantageous or necessary to prepare a fluorophore-protein conjugate having a defined number of fluorescent dye groups—e.g., only one fluorescent dye covalently conjugated to the protein, or only two fluorescent dyes covalently conjugated to the protein—in order to optimize signals in an imaging application or reporter assay. One of skill in the art will appreciate that the "defined" number of conjugate groups will depend on the application for which the protein conjugate is intended to be used. The defined number of groups can be, for example, one conjugate group, two conjugate groups, three conjugate groups, four conjugate groups, five conjugate groups, or more conjugate groups depending on the application.

As described above, a bioconjugation reaction will very often result in a product mixture containing products having different numbers of conjugate groups. In such cases, a certain fraction of the protein in the product mixture can have fewer conjugate groups than the desired, defined number or more conjugate groups than the desired, defined number. In typical bioconjugation reactions, product mixtures can contain unmodified protein or modified proteins with one, two, three, four, five, or more conjugate groups. In the methods of the invention, protein mixtures can contain unmodified protein as well as modified proteins with one, two, three, four, five, or more handle moieties. The distribution of handle moieties in the protein mixture may vary, depending on the particular protein and conjugation reagents used for installing the handle moieties.

As set forth above, the method of the invention includes forming a mixture containing a macrocyclic matrix material and a plurality of proteins, wherein each protein in a first population of proteins in the plurality has a first number of handle moieties, and each protein in a second population of proteins in the plurality has a second number of handle moieties. The protein mixture can have further pluralities having additional numbers of modifications. Each particular plurality will typically represent anywhere from about 1% (w/w) to about 90% (w/w), or more, of the total protein in the protein mixture. It is one object of the invention to separate the proteins having the desired number of handle moieties (i.e., a first plurality) from proteins having more or less than the desired number of handle moieties (i.e., members of the second, third, fourth, or higher-order pluralities). In some embodiments, for example, each protein in the first population of proteins has one handle moiety, and each protein in the second population of proteins has two handle moieties. In some embodiments, each protein in the first population has zero handle moieties, and each protein in the second population has one handle moiety.

The method of the invention further includes eluting the proteins from the macrocyclic matrix material to obtain a first separated protein fraction and a second separated protein fraction, wherein: substantially all of the proteins in the first separated protein fraction have the first number of handle moieties, and substantially all of the proteins in the second separated protein fraction have the second number of handle moieties. In practice, eluting the proteins from the matrix material can include collecting a number of fractions (e.g., 5, 10, 25, or more fractions). Fractions are generally collected in a sequential manner, and proteins having different numbers of handle moieties can elute sequentially (i.e., unmodified proteins having no handle moieties can elute prior to proteins have one handle moiety, which can elute prior to proteins having two handle moieties, etc.). It is an object of the invention to isolate the proteins having the desired number of handle moieties in particular fractions, although one of skill in the art will understand that certain fractions may have fewer or more than the desired handle moieties. Use of the term "substantially," in connection with a particular number of handle moieties per protein in a given fraction, means that at least 50% (w/w) of the proteins in the fraction have that number of handle moieties. When substantially all of the proteins in a first separated protein fraction have a first number handle moieties, it is meant that at least about 50, 55, 60, 65, 70, 75, 80, 85, 90, 95, or 99% (w/w) of the proteins in the first separated protein fraction have the first number of handle moieties (e.g., one handle moiety or two handle moieties). The remaining protein in the original mixture is typically contained within further protein fractions; one or more of these further fractions can contain proteins having further numbers of handle moieties.

A. Handle Moieties for Use in the Invention

Any handle moiety suitable for generation of a reactive moiety and further modification with a conjugation reagent can be used in the methods of the invention. Examples of suitable handle moieties include, but are not limited to, those including an azo group (having a —N=N— moiety; including aromatic azo groups); a disulfide group (having a —S=S— moiety), a hydrazone group (having a —RC=N—N(R)— moiety, wherein each R is H or $C_{1-6}$ alkyl), an imine group (having a —RC=N— moiety, wherein R is H or $C_{1-6}$ alkyl), or a diol group (including vicinal diols having a —R(OH)C=C(OH)R— moiety, wherein R is H or $C_{1-6}$ alkyl). As described in more detail below, the handle moieties are also designed such that they form host guest complexes with the macrocyclic matrix material.

In some embodiments, the invention provides a method for preparing a protein conjugate having a defined number of conjugate groups as described above, wherein the handle moiety includes an azo group. In some such embodiments, the handle moiety includes a structure according to Formula I:

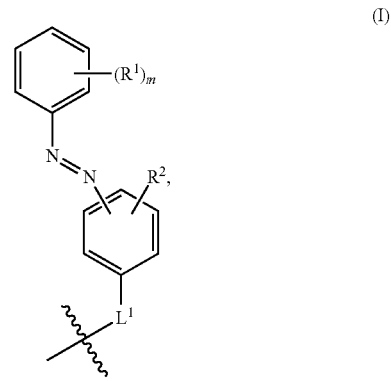

(I)

or a salt thereof, wherein m is an integer ranging from 0 to 5, each $R^1$ is independently selected from —$OR^a$, —$N(R^a)_3$, —$SO_3H$, and —$CO_2H$;

$R^2$ is selected from H and —$OR^a$;

each $R^a$ is independently selected from H and $C_{1-6}$ alkyl; and $L^1$ is a linking moiety.

In some embodiments, the handle moiety includes a structure according to Formula Ia:

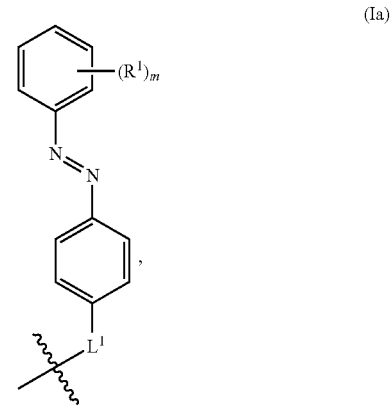

(Ia)

or a salt thereof, wherein m is an integer ranging from 0 to 5, each $R^1$ is independently selected from the group consisting of —$OR^a$, —$N(R^a)_3$, —$SO_3H$, and —$CO_2H$, wherein each $R^a$ is independently selected from H and $C_{1-6}$; and $L^1$ is a linking moiety.

In some embodiments, the handle moiety includes a structure according to Formula Ib or Ic:

(Ib)

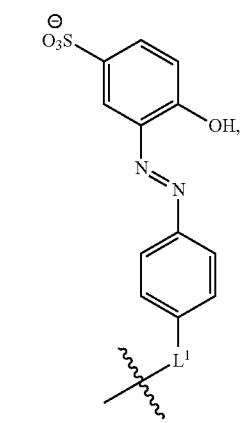

(Ic)

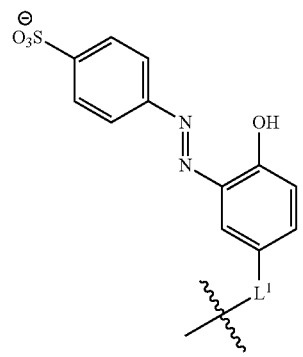

wherein $L^1$ is a linking moiety.

In some embodiments, the linking moiety in the structure of Formula I, Ia, Ib, or Ic includes a structure selected from:

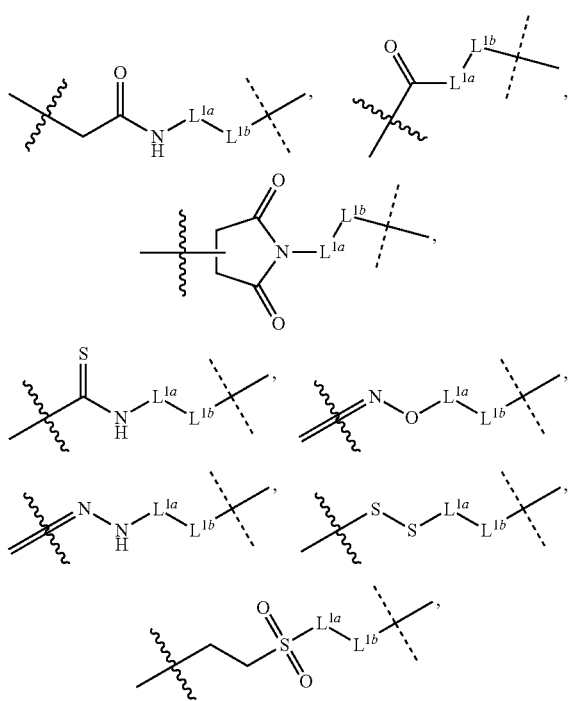

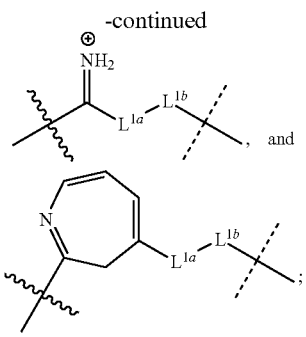

-continued

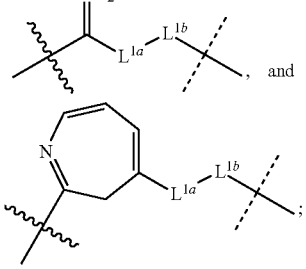

wherein $L^{1a}$ and $L^{1b}$ are independently selected from a bond, a divalent polymer moiety, and linear or branched, saturated or unsaturated $C_{1-30}$ alkyl; wherein one or more carbon atoms in the $C_{1-30}$ alkyl is optionally and independently replaced by O, S, $NR^a$; wherein two or more groupings of adjacent carbon atoms in the $C_{1-30}$ alkyl are optionally and independently replaced by —$NR^a(CO)$— or —$(CO)NR^a$—; and wherein two or more groupings of adjacent carbon atoms in the $C_{1-30}$ alkyl are optionally and independently replaced by a 4- to 8-membered, divalent carbocycle or a 4- to 8-membered, divalent heterocycle having one to four heteroatoms selected from O, S, and N;

each $R^a$ is independently selected from H and $C_{1-6}$ alkyl;

the wavy line represents the point of connection to the protein; and the dashed line represents the point of connection to the structure of Formula I.

One of skill in the art will appreciate that the handle moieties in the proteins can be installed using various chemistries for protein modification, and that the linking moieties described above result from the reaction of protein functional groups (i.e., amino acid side chains), with reagents having reactive linker groups. A wide variety of such reagents are known in the art. Examples of such reagents include, but are not limited to, N-hydroxysuccinimidyl (NHS) esters and N-hydroxysulfosuccinimidyl (sulfo-NHS) esters (amine reactive); carbodiimides (amine and carboxyl reactive); hydroxymethyl phosphines (amine reactive); maleimides (sulfhydryl reactive); aryl azides (primary amine reactive); fluorinated aryl azides (reactive via carbon-hydrogen (C—H) insertion); pentafluorophenyl (PFP) esters (amine reactive); imidoesters (amine reactive); isocyanates (hydroxyl reactive); vinyl sulfones (sulfhydryl, amine, and hydroxyl reactive); pyridyl disulfides (sulfhydryl reactive); and benzophenone derivatives (reactive via C—H bond insertion). Further reagents include but are not limited to those groups and methods described in Hermanson, *Bioconjugate Techniques* 2nd Edition, Academic Press, 2008.

Accordingly, the invention provides embodiments wherein the handle moieties are installed using a reagent selected from:

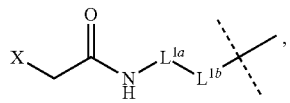

-continued

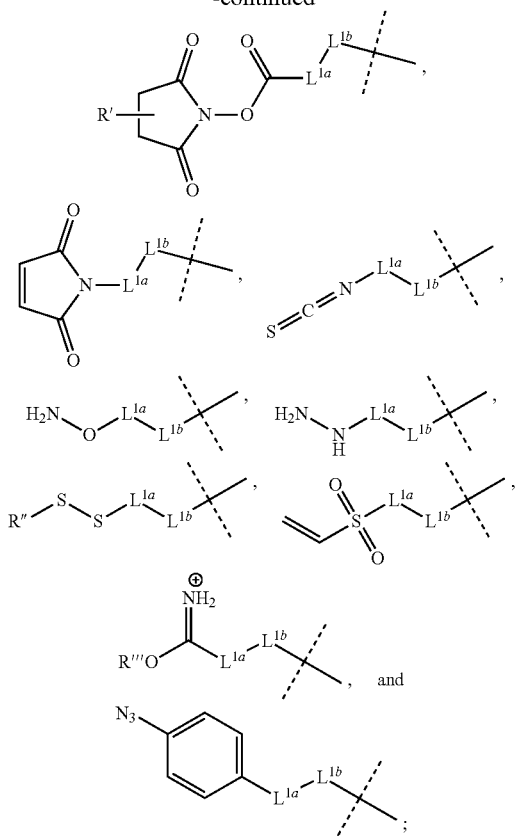

wherein X is halogen (e.g., iodo or chloro); R' is H or sulfo; R" is optionally substituted aryl (e.g., 3-carboxy-4-nitrophenyl) or optionally substituted heteroaryl (e.g., pyridin-2-yl); R''' is optionally substituted alkyl (e.g., methoxy); $L^{1a}$ and $L^{1b}$ are as described above; and the dashed line represents the point of connection to the structure of Formula I, Ia, Ib, or Ic as described above.

Reaction mixtures for installing handle moieties can contain additional reagents of the sort typically used in bioconjugation reactions. For example, in certain embodiments, the reaction mixtures can contain buffers (e.g., 2-(N-morpholino)ethanesulfonic acid (MES), 2-[4-(2-hydroxyethyl)piperazin-1-yl]ethanesulfonic acid (HEPES), 3-morpholinopropane-1-sulfonic acid (MOPS), 2-amino-2-hydroxymethyl-propane-1,3-diol (TRIS), potassium phosphate, sodium phosphate, phosphate-buffered saline, sodium citrate, sodium acetate, and sodium borate), cosolvents (e.g., dimethylsulfoxide, dimethylformamide, ethanol, methanol, tetrahydrofuran, acetone, and acetic acid), salts (e.g., NaCl, KCl, $CaCl_2$, and salts of $Mn^{2+}$ and $Mg^{2+}$), detergents/surfactants (e.g., a non-ionic surfactant such as N,N-bis[3-(D-gluconamido)propyl]cholamide, polyoxyethylene (20) cetyl ether, dimethyldecylphosphine oxide, branched octylphenoxy poly(ethyleneoxy)ethanol, a polyoxyethylene-polyoxypropylene block copolymer, t-octylphenoxypolyethoxyethanol, polyoxyethylene (20) sorbitan monooleate, and the like; an anionic surfactant such as sodium cholate, N-lauroylsarcosine, sodium dodecyl sulfate, and the like; a cationic surfactant such as hexdecyltrimethyl ammonium bromide, trimethyl(tetradecyl) ammonium bromide, and the like; or a zwitterionic surfactant such as an amidosulfobetaine, 3-[(3-cholamidopropyl)dimethyl-ammonio]-1-propanesulfonate, and the like), chelators (e.g., ethylene glycol-bis(2-aminoethylether)-N,N,N',N'-tetraacetic acid (EGTA), 2-({2-[bis(carboxymethyl)amino]ethyl} (carboxymethyl)amino)acetic acid (EDTA), and 1,2-bis(o-aminophenoxy)ethane-N,N,N,N-tetraacetic acid (BAPTA)), and reducing agents (e.g., dithiothreitol (DTT), β-mercaptoethanol (BME), and tris(2-carboxyethyl)phosphine (TCEP)). Buffers, cosolvents, salts, detergents/surfactants, chelators, and reducing agents can be used at any suitable concentration, which can be readily determined by one of skill in the art. In general, buffers, cosolvents, salts, detergents/surfactants, chelators, and reducing agents are included in reaction mixtures at concentrations ranging from about 1 μM to about 1 M. For example, a buffer, a cosolvent, a salt, a detergent/surfactant, a chelator, or a reducing agent can be included in a reaction mixture at a concentration of about 1 μM, or about 10 μM, or about 100 μM, or about 1 mM, or about 10 mM, or about 25 mM, or about 50 mM, or about 100 mM, or about 250 mM, or about 500 mM, or about 1 M.

The reactions are conducted under conditions sufficient to install the handle moiety in the protein conjugate. The reactions can be conducted at any suitable temperature. In general, the reactions are conducted at a temperature of from about 4° C. to about 40° C. The reactions can be conducted, for example, at about 25° C. or about 37° C. The reactions can be conducted at any suitable pH. In general, the reactions are conducted at a pH of from about 4.5 to about 10. The reactions can be conducted, for example, at a pH of from about 5 to about 9. The reactions can be conducted for any suitable length of time. In general, the reaction mixtures are incubated under suitable conditions for anywhere between about 1 minute and several hours. The reactions can be conducted, for example, for about 1 minute, or about 5 minutes, or about 10 minutes, or about 30 minutes, or about 1 hour, or about 2 hours, or about 4 hours, or about 8 hours, or about 12 hours, or about 24 hours, or about 48 hours, or about 72 hours. Other reaction conditions may be employed in the methods of the invention, depending on the identity of the protein in the conjugate and the reagent used for installing the handle moiety.

B. Conversion of Handle Moieties to Reactive Moieties

As described above, the handle moieties in the separated protein fractions are contacted with a conversion reagent to form reactive moieties for further modification. The choice of conversion reagent will depend on the identity of the handle moiety (i.e., whether the handle moiety contains an azo group, a disulfide group, a hydrazone group, an imine group, a diol group, or another functional group). Any conditions suitable for converting the handle moieties to reactive moieties can be used in the methods of the invention. For example, an aromatic azo group can be reduced to form a reactive aniline group; a disulfide group can be reduced to form a reactive thiol group; hydrazone groups and imine groups can be hydrolyzed to form reactive carbonyl groups; and a vicinal diol group can be oxidized to form a reactive aldehyde group.

When the modified proteins have handle moieties containing an azo group (e.g., a structure according to Formula I, as described above), the azo group can be reduced to provide a reactive aniline group for further modification. Accordingly, some embodiments of the invention provide methods wherein the reactive moiety includes a structure according to Formula II:

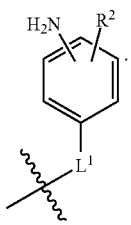

(II)

In some embodiments, the reactive moiety includes a structure according to Formula IIa or Formula IIb:

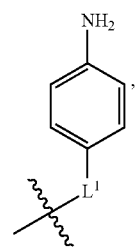

(IIa)

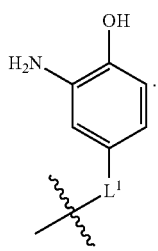

(IIb)

In some embodiments, the reactive moiety includes a structure according to Formula IIa.

Any reducing agent suitable for converting the azo group to an aniline can be used in the method of the invention. Examples of suitable reducing agents include, but are not limited to, sodium dithionite, sodium cyanoborohydride, ascorbic acid, dithiothreitol, tris(2-carboxyethyl)phosphine, and the like. In some embodiments, the reducing agent is selected from sodium dithionite and sodium cyanoborohydride. In some embodiments, the reducing agent is sodium dithionite. In general, at least one equivalent of the reducing agent per handle moiety is used, and—more typically—the reducing agent will be used in excess with respect to the modified proteins and the handle moieties. In certain embodiments, converting an azo handle moiety to an aniline reactive moiety includes combining the modified protein with at least 10 equivalents of sodium dithionine. For example, the modified protein can be combined with 10, 50, 100, or 250 equivalents of sodium dithionite. Reduction of azo handle moieties is typically conducted for anywhere between a few minutes and several hours at temperatures around room temperature (i.e., around 20° C. or 25° C.), although other time periods and temperatures (e.g., 4° C. or 37° C.) can be used depending on the structure of the handle moiety and the particular reducing agent employed.

C. Modification of Reactive Moieties with Conjugation Reagents

Following conversion of the handle moieties, the reactive moieties are contacted with a conjugation reagent under conditions sufficient to form the desired protein conjugates.

Any conditions suitable for converting the reactive moieties to the conjugate groups can be used in the methods of the invention. For example, an aniline reactive group can be modified with an aminophenol; a thiol reactive group can be modified with a maleimide or an iodoacetamide; and an aldehyde reactive group can be modified with a hydroxylamine. Other reagents and modification strategies known in the art, including those described above for installation of handle moieties, can be employed to modify the reactive groups afforded by conversion of the handle moieties.

In some embodiments, the conjugation reagent contains a structure according to Formula III:

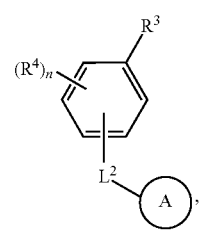

(III)

wherein:

$R^3$ is selected from —$N(R^a)_2$ and —$OR^a$;

$R^4$ is selected from —$OR^a$, $C_{1-6}$ alkyl, —$N(R^a)_2$, —$N_3$, and —$NH(CO)R^a$;

subscript n is an integer ranging from 0 to 3;

each $R^a$ is independently selected from H and $C_{1-6}$ alkyl;

$L^2$ is a linking moiety; and

A is a prosthetic moiety.

In some embodiments, the conjugation reagent contains a structure according to Formula IIIa:

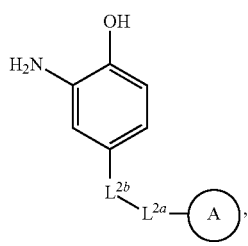

(IIIa)

wherein $L^{2a}$ and $L^{2b}$ are independently selected from a bond, a divalent polymer moiety, and linear or branched, saturated or unsaturated $C_{1-30}$ alkyl; wherein one or more carbon atoms in the $C_{1-30}$ alkyl is optionally and independently replaced by O, S, $NR^a$; wherein two or more groupings of adjacent carbon atoms in the $C_{1-30}$ alkyl are optionally and independently replaced by —$NR^a(CO)$— or —$(CO)NR^a$—; and wherein two or more groupings of adjacent carbon atoms in the $C_{1-30}$ alkyl are optionally and independently replaced by a 4- to 8-membered, divalent carbocycle or a 4- to 8-membered, divalent heterocycle having one to four heteroatoms selected from O, S, and N; and each $R^a$ is independently selected from H and $C_{1-6}$ alkyl.

In some embodiments, the conjugation reagent contains a structure according to Formula IIIb:

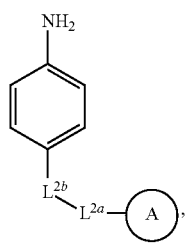

(IIIb)

wherein $L^{2a}$, $L^{2b}$, and A are as described above.

The conjugation agents can include a variety of prosthetic moieties; as such, the methods of the invention are widely applicable to preparation of bioconjugates for use in various applications. In some embodiments, the prosthetic moiety is selected from a chromophore, a fluorophore, a polymer, a peptide, a nucleic acid, a therapeutic agent, and a diagnostic agent.

Drugs that can be installed in the protein conjugates include, but are not limited to, aplidin, azaribine, anastrozole, azacytidine, bleomycin, bortezomib, bryostatin-1, busulfan, calicheamycin, camptothecin, 10-hydroxycamptothecin, carmustine, celebrex, chlorambucil, cisplatin, irinotecan (CPT-11), SN-38, carboplatin, cladribine, cyclophosphamide, cytarabine, dacarbazine, docetaxel, dactinomycin, daunomycin glucuronide, daunorubicin, dexamethasone, diethylstilbestrol, doxorubicin, 2-pyrrolinodoxorubicine (2P-DOX), cyano-morpholino doxorubicin, doxorubicin glucuronide, epirubicin glucuronide, ethinyl estradiol, estramustine, etoposide, etoposide glucuronide, etoposide phosphate, floxuridine (FUdR), 3',5'-O-dioleoyl-FudR (FUdR-dO), fludarabine, flutamide, fluorouracil, fluoxymesterone, gemcitabine, hydroxyprogesterone caproate, hydroxyurea, idarubicin, ifosfamide, L-asparaginase, leucovorin, lomustine, mechlorethamine, medroprogesterone acetate, megestrol acetate, melphalan, mercaptopurine, 6-mercaptopurine, methotrexate, mitoxantrone, mithramycin, mitomycin, mitotane, phenyl butyrate, prednisone, procarbazine, paclitaxel, pentostatin, PSI-341, semustine streptozocin, tamoxifen, taxanes, taxol, testosterone propionate, thalidomide, thioguanine, thiotepa, teniposide, topotecan, uracil mustard, velcade, vinblastine, vinorelbine, vincristine, ricin, abrin, ribonuclease, onconase, rapLR1, DNase I, Staphylococcal enterotoxin-A, pokeweed antiviral protein, gelonin, diphtheria toxin, *Pseudomonas* exotoxin, and *Pseudomonas* endotoxin.

Diagnostic agents that can be installed in the protein conjugates include any diagnostic agent known in the art, as provided, for example, in the following references: Armstrong et al., *Diagnostic Imaging*, 5$^{th}$ Ed., Blackwell Publishing (2004); Torchilin, V. P., Ed., *Targeted Delivery of Imaging Agents*, CRC Press (1995); Vallabhajosula, S., *Molecular Imaging: Radiopharmaceuticals for PET and SPECT*, Springer (2009). A diagnostic agent can be detected by a variety of ways, including as an agent providing and/or enhancing a detectable signal that includes, but is not limited to, gamma-emitting, radioactive, echogenic, optical, fluorescent, absorptive, magnetic or tomography signals. Techniques for imaging the diagnostic agent can include, but are not limited to, single photon emission computed tomography (SPECT), magnetic resonance imaging (MRI), optical imaging, positron emission tomography (PET), computed tomography (CT), x-ray imaging, gamma ray imaging, and the like.

Diagnostic agents can include chelators that bind to metal ions to be used for a variety of diagnostic imaging techniques. Exemplary chelators include, but are not limited to, ethylenediaminetetraacetic acid (EDTA), [4-(1,4,8,11-tetraazacyclotetradec-1-yl) methyl]benzoic acid (CPTA), cyclohexanediaminetetraacetic acid (CDTA), ethylenebis(oxyethylenenitrilo)tetraacetic acid (EGTA), diethylenetriaminepentaacetic acid (DTPA), citric acid, hydroxyethyl ethylenediamine triacetic acid (HEDTA), iminodiacetic acid (IDA), triethylene tetraamine hexaacetic acid (TTHA), 1,4,7,10-tetraazacyclododecane-1,4,7,10-tetra(methylene phosphonic acid) (DOTP), 1,4,8,11-tetraazacyclododecane-1,4,8,11-tetraacetic acid (TETA), 1,4,7,10-tetraazacyclododecane-1,4,7,10-tetraacetic acid (DOTA), and derivatives thereof.

Radioisotopes can be incorporated into certain diagnostic agents described herein and can include radionuclides that emit gamma rays, positrons, beta and alpha particles, and X-rays. Suitable radionuclides include, but are not limited to, $^{225}$Ac, $^{72}$As, $^{211}$At, $^{11}$B, $^{128}$Ba, $^{212}$Bi, $^{75}$Br, $^{77}$Br, $^{14}$C, $^{109}$Cd, $^{62}$Cu, $^{64}$Cu, $^{67}$Cu, $^{18}$F, $^{67}$Ga, $^{68}$Ga, $^{3}$H, $^{123}$I, $^{125}$I, $^{130}$I, $^{131}$I, $^{111}$In, $^{77}$Lu, $^{13}$N, $^{15}$O, $^{32}$P, $^{33}$P, $^{212}$Pb, $^{103}$Pd, $^{186}$Re, $^{188}$Re, $^{47}$Sc, $^{153}$Sm, $^{89}$Sr, $^{99m}$Tc, $^{88}$Y and $^{90}$Y. In certain embodiments, radioactive agents can include $^{111}$In-DTPA, $^{99m}$Tc(CO)$_3$-DTPA, $^{99m}$Tc(CO)$_3$-ENPy2, $^{62/64/67}$Cu-TETA, $^{99m}$Tc(CO)$_3$-IDA, and $^{99m}$Tc(CO)$_3$triamines (cyclic or linear). In other embodiments, the agents can include DOTA and its various analogs with $^{111}$In, $^{177}$Lu, $^{153}$Sm, $^{88/90}$Y, $^{62/64/67}$Cu, or $^{67/68}$Ga.

The diagnostic agents can include optical agents such as fluorescent agents, phosphorescent agents, chemiluminescent agents, and the like. Numerous agents (e.g., dyes, probes, labels, or indicators) are known in the art and can be used in the present invention. (See, e.g., Invitrogen, The Handbook—A Guide to Fluorescent Probes and Labeling Technologies, Tenth Edition (2005)). Fluorescent agents can include a variety of organic and/or inorganic small molecules or a variety of fluorescent proteins and derivatives thereof. For example, fluorescent agents can include, but are not limited to, cyanines, phthalocyanines, porphyrins, indocyanines, rhodamines, phenoxazines, phenylxanthenes, phenothiazines, phenoselenazines, fluoresceins, benzoporphyrins, squaraines, dipyrrolo pyrimidones, tetracenes, quinolines, pyrazines, corrins, croconiums, acridones, phenanthridines, rhodamines, acridines, anthraquinones, chalcogenopyrylium analogues, chlorins, naphthalocyanines, methine dyes, indolenium dyes, azo compounds, azulenes, azaazulenes, triphenyl methane dyes, indoles, benzoindoles, indocarbocyanines, benzoindocarbocyanines, and BODIPY™ derivatives having the general structure of 4,4-difluoro-4-bora-3a,4a-diaza-s-indacene, and/or conjugates and/or derivatives of any of these. Other agents that can be used include, but are not limited to, fluorescein, fluorescein-polyaspartic acid conjugates, fluorescein-polyglutamic acid conjugates, fluorescein-polyarginine conjugates, indocyanine green, indocyanine-dodecaaspartic acid conjugates, indocyanine-polyaspartic acid conjugates, isosulfan blue, indole disulfonates, benzoindole disulfonate, bis(ethylcarboxymethyl)indocyanine, bis(pentylcarboxymethyl)indocyanine, polyhydroxyindole sulfonates, polyhydroxybenzoindole sulfonate, rigid heteroatomic indole sulfonate, indocyaninebispropanoic acid, indocyaninebishexanoic acid, 3,6-dicyano-2,5-[(N,N,N',N'-tetrakis(carboxymethyl)amino]pyrazine, 3,6-[(N,N,N',N'-tetrakis(2-hydroxyethyl)amino]pyrazine-2,5-dicarboxylic acid, 3,6-bis(N-azatedino)pyrazine-2,5-dicarboxylic acid, 3,6-bis(N-morpholino)pyrazine-2,5-dicarboxylic acid, 3,6- bis(N-piperazino)pyrazine-2,5-dicarboxylic acid, 3,6-bis(N-thiomorpholino)pyrazine-2,5-dicarboxylic acid, 3,6-bis(N-thiomorpholino)pyrazine-2,5-dicarboxylic acid S-oxide, 2,5-dicyano-3,6-bis(N-thiomorpholino)pyrazine S,S-dioxide, indocarbocyaninetetrasulfonate, chloroindocarbocyanine, and 3,6-diaminopyrazine-2,5-dicarboxylic acid.

Diagnostic agents can include magnetic resonance (MR) and x-ray contrast agents that are generally well known in the art, including, for example, iodine-based x-ray contrast agents, superparamagnetic iron oxide (SPIO), complexes of gadolinium or manganese, and the like. (See, e.g., Armstrong et al., *Diagnostic Imaging*, 5$^{th}$ Ed., Blackwell Publishing (2004)). In some embodiments, a diagnostic agent can include a magnetic resonance (MR) imaging agent. Exemplary magnetic resonance agents include, but are not limited to, paramagnetic agents, superparamagnetic agents, and the like. Exemplary paramagnetic agents can include, but are not limited to, gadopentetic acid, gadoteric acid, gadodiamide, gadolinium, gadoteridol, mangafodipir, gadoversetamide, ferric ammonium citrate, gadobenic acid, gadobutrol, or gadoxetic acid. Superparamagnetic agents can include, but are not limited, to superparamagnetic iron oxide and ferristene. In certain embodiments, the diagnostic agents can include x-ray contrast agents as provided, for example, in the following references: H. S Thomsen, R. N. Muller and R. F. Mattrey, Eds., *Trends in Contrast Media*, (Berlin: Springer-Verlag, 1999); P. Dawson, D. Cosgrove and R. Grainger, Eds., *Textbook of Contrast Media* (ISIS Medical Media 1999); Torchilin, V. P., *Curr. Pharm. Biotech.* 1:183-215 (2000); Bogdanov, A. A. et al., *Adv. Drug Del. Rev.* 37:279-293 (1999); Sachse, A. et al., *Investigative Radiology* 32(1):44-50 (1997). Examples of x-ray contrast agents include, without limitation, iopamidol, iomeprol, iohexol, iopentol, iopromide, iosimide, ioversol, iotrolan, iotasul, iodixanol, iodecimol, ioglucamide, ioglunide, iogulamide, iosarcol, ioxilan, iopamiron, metrizamide, iobitridol and iosimenol.

Targeting agents can also be installed in the protein conjugates. Generally, the targeting agents will be able to associate with a target of interest, such as a target associated with an organ, tissues, cell, extracellular matrix, or intracellular region. In certain embodiments, a target can be associated with a particular disease state, such as a cancerous condition. In some embodiments, the targeting component can be specific to only one target, such as a receptor. Suitable targets include, but are not limited to, a nucleic acid, such as a DNA, RNA, or modified derivatives thereof. Suitable targets can also include proteins, such as an extracellular protein, a receptor, a cell surface receptor, a tumor-marker, a transmembrane protein, an enzyme, or an antibody. Suitable targets can include a carbohydrate, such as a monosaccharide, disaccharide, or polysaccharide that can be, for example, present on the surface of a cell.

In certain embodiments, a targeting agent can include a target ligand (e.g., an RGD-containing peptide), a small molecule mimic of a target ligand (e.g., a peptide mimetic ligand), or an antibody or antibody fragment specific for a particular target. In some embodiments, a targeting agent can further include folic acid derivatives, B-12 derivatives, integrin RGD peptides, NGR derivatives, somatostatin derivatives or peptides that bind to the somatostatin receptor, e.g., octreotide and octreotate, and the like. The targeting agents can also include an aptamer. Aptamers can be designed to associate with or bind to a target of interest. Aptamers can consist of, for example, DNA, RNA, and/or peptides, and certain aspects of aptamers are well known in the art. (See. e.g., Klussman, S., Ed., The Aptamer Handbook, Wiley-VCH (2006); Nissenbaum, E. T., *Trends in Biotech.* 26(8): 442-449 (2008)).

Polymers can also be installed in the protein conjugates. Suitable polymers include natural polymers, semisynthetic polymers, and synthetic polymers. Suitable synthetic polymers include, but are not limited to, polymers or copolymers derived from polydioxane, polyphosphazene, polysulphone resins, poly(acrylic acid), poly(acrylic acid) butyl ester, poly(ethylene glycol), poly(propylene), polyurethane resins, poly(methacrylic acid), poly(methacrylic acid)-methyl ester, poly(methacrylic acid)-n butyl ester, poly(methacrylic acid)-t butyl ester, polytetrafluoroethylene, polyperfluoropropylene, poly N-vinyl carbazole, poly(methyl isopropenyl ketone), poly alphamethyl styrene, polyvinylacetate, poly (oxymethylene), poly(ethylene-co-vinyl acetate), a polyurethane, a poly(vinyl alcohol), and polyethylene terephthalate; ethylene vinyl alcohol copolymer (commonly known by the generic name EVOH or by the trade name EVAL); polybutylmethacrylate; poly(hydroxyvalerate); poly(L-lactic acid) or poly(L-lactide); poly(e-caprolactone); poly(lactide-co-glycolide); poly(hydroxybutyrate); poly(hydroxybutyrate-co-valerate); polydioxanone; polyorthoester; polyanhydride; poly(glycolic acid) (PGA); poly(D,L-lactide) (PDLL); poly (L-Lactide)(PLL); copolymers of PGA, poly(D,L-lactic acid) (PDLA), and/or poly(lactic acid) (PLA); poly(glycolic acid-co-trimethylene carbonate); polyphosphoester; poly-phosphoester urethane; poly(amino acids); cyanoacrylates; poly(trimethylene carbonate); poly(iminocarbonate); copoly (ether-esters) (e.g., poly(ethylene oxide) (PEO)/PLA); polyalkylene oxalates; polyphosphazenes; polyurethanes; silicones; polyesters; polyolefins; polyisobutylene and ethylene-alphaolefin copolymers; acrylic polymers and copolymers; vinyl halide polymers and copolymers, such as polyvinyl chloride; polyvinyl ethers, such as polyvinyl methyl ether; polyvinylidene halides, such as polyvinylidene fluoride and polyvinylidene chloride; polyacrylonitrile; polyvinyl ketones; polyvinyl aromatics, such as polystyrene; polyvinyl esters, such as polyvinyl acetate; copolymers of vinyl monomers with each other and olefins, such as ethylene-methyl methacrylate copolymers, acrylonitrile-styrene copolymers, ABS resins, and ethylene-vinyl acetate copolymers; polyamides, such as Nylon 66 and polycaprolactam; alkyd resins; polycarbonates; polyoxymethylenes; polyimides; polyethers; epoxy resins; polyurethanes; rayon; rayon-triacetate; cellulose; cellulose acetate; cellulose butyrate; cellulose acetate butyrate; cellophane; cellulose nitrate; cellulose propionate; cellulose ethers; amorphous Teflon; and carboxymethyl cellulose.

Suitable hydrophobic polymers include poly(L-lactide), poly(glycolide), poly(e-caprolactone), copolymers of lactide and/or glycolide or/and poly(e-caprolactone), hydrophobic peptides or a combination of hydrophobic peptides, polyurethanes. Any hydrophobic polymer that can form a micelle in water is suitable for use as a hydrophobic polymer. Suitable hydrophobic polymers include, e.g., poly(glycolide) or poly(glycolic acid); poly(e-caprolactone); poly(D, L-lactide); poly(L-Lactide); copolymers of these and other polyesters; polyamides; polyanhydrides; polyurethanes; poly(ortho esters); poly(iminocarbonates). In some embodiments, the hydrophobic polymer of the nanoparticle (or microparticle) is poly-L-lactide. Suitable hydrophilic polymers include, but are not limited to, poly(ethylene glycol); poly(vinyl alcohol); polyethers; poly(methacrylic acid); poly(acrylic acid); poly(hydroxyethylmethacrylate) (pHEMA); hyaluronic acid; and hyaluronate.

When conjugation reagents according to Formula III are used, the contacting step is conducted in the presence of an oxidizing agent. Any oxidizing agent suitable for forming the bioconjugates with reagents according to Formula III can be used in the methods of the invention. Examples of suitable oxidizing agents include, but are not limited to, sodium periodate, silver trifluoroacetate, cerium ammonium nitrate, copper sulfate, and potassium ferricyanide. In some embodiments, the oxidizing agent is selected from sodium periodate, cerium ammonium nitrate, and potassium ferricyanide. In some such embodiments, the oxidizing agent is potassium ferricyanide.

As for the reducing agents described above, the oxidizing agent will typically be used in excess with respect to the modified proteins and the reactive aniline moieties. In certain embodiments, converting an aniline reactive moiety to the oxidized bioconjugate includes combining the modified protein with at least 10 equivalents of the oxidizing agent (e.g., potassium ferricyanide). For example, the modified protein can be combined with 10, 50, 100, or 250 equivalents of potassium ferricyanide. The oxidative coupling step is typically conducted for anywhere between a few minutes and several hours at temperatures around room temperature (i.e., around 20° C. or 25° C.), although other time periods and temperatures (e.g., 4° C. or 37° C.) can be used depending on the structure of the reactive aniline moiety, the structure of the conjugation reagent according to Formula III, and the particular oxidizing agent employed.

In some embodiments where conjugation reagents according to Formula III are used, the protein conjugate contains a structure according to Formula IV:

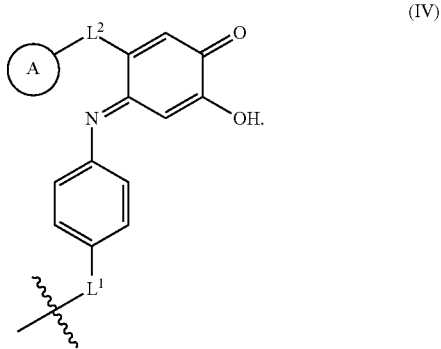

(IV)

In some embodiments where conjugation reagents according to Formula III are used, the protein conjugate contains a structure according to Formula V:

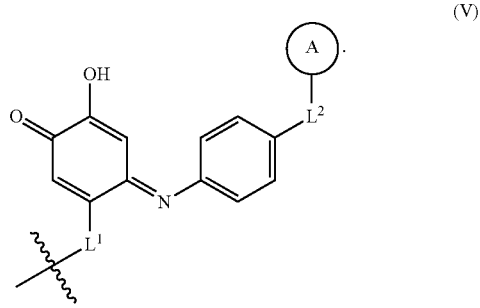

(V)

D. Matrix Materials and Affinity Chromatography

As described above, the method of the invention includes forming a mixture comprising modified proteins and a macrocyclic matrix material, and the mixture is formed under conditions sufficient to bind the modified proteins to the macrocyclic matrix material. In general, the macrocyclic matrix material contains a plurality of macrocyclic host moieties and solid-phase support material. Any support material and host moiety suitable for forming host guest complexes with the modified proteins can be used in the methods of the invention.

Macrocyclic host guest complexes have been studied in various contexts, and binding constants and other thermodynamic properties for numerous host guest systems have been determined. For example, binding constants for cyclodextrin complexes with several hundred ligands in different solution conditions have been reported (see, e.g., Rekharsky and Inoue, Chem. Rev. 98 (5), 1998, 1875-1918). Binding constants for the cyclodextrin complexes range over four to five orders of magnitude. This dynamic range provides an opportunity for development of systems having tunable thermodynamics using different ligands. In general, dissociation constants ($K_a$) for host guest complexes formed by macrocyclic host moieties in the matrix and the handle moieties in the modified proteins will range from about $10$ $M^{-1}$ to about $10^5$ $M^{-1}$. In some embodiments, the dissociation constant $K_a$ for the host guest complex ranges from about $10^3$ $M^{-1}$ to about $10^4$ $M^{-1}$. In the case of azo handle moieties and β-cyclodextrins, binding constants can be determined in a buffer (e.g., 10 mM pH 6.5 phosphate buffer) by monitoring absorbance at 375 nm as described herein. Under these conditions, useful host guest complexes have exhibited binding constants ranging from about $10^3$ $M^{-1}$ to about $10^4$ $M^{-1}$ (e.g., $10^{3.47}$ $M^{-1}$).

Examples of macrocyclic moieties that can be used in the methods of the invention include, but are not limited to cyclodextrins, cucurbiturils, calixarenes, cyclophanes, resorcinarenes, and calixpyridines. Calixarenes, for example, are macrocycles formed by the condensation of phenolic and heterocyclic units and aldehydes or derivatives thereof, characterized by a concave headgroup (often containing peripheral heteroatoms or heteroatom-containing functional groups), and optional tailgroup substituents such as hydrocarbon chains, aromatic rings, polyether chains, or combinations thereof. Examples include resorcinol (1,3 hydroxybenzene)-derived calixarenes (resorcinarenes and cavitands), pyridine-derived calixarenes (pyridene-arenes), and pyrrole-derived calixarenes (calix-pyrroles). Exemplary calixarenes include resorcinol-derived calixarenes (resorcinarenes) with various functional groups attached either to the macrocylic headgroup or the tailgroups (e.g., terminal olefins, amines, thiols, alcohols, carboxylates, and other functional groups or derivatives thereof). Functionalized calixarenes, resorcinarenes, and calixpyridines (as described, for example, in U.S. Pat. Nos. 5,218,060; 5,688,998; 6,262,257; 6,899,947; and 7,396,895) can be used in the methods of the invention. Cyclophanes are macrocyclic groups having one or more (e.g., two or more) aromatic rings (e.g., benzene rings), and at least one aliphatic bridge between two adjacent or non-adjacent positions of the aromatic ring(s). Functionalized cyclophanes (as described, for example, in U.S. Pat. Nos. 5,147,882 and 8,809,313) can be used in the methods of the invention.

In some embodiments, the macrocyclic matrix material includes a plurality of macrocyclic moieties independently selected from a cyclodextrin group, a cucurbituril group, a calixarene group, a cyclophane group, a resorcinarene group, and a calixpyridine group. In some embodiments, the macrocylic moieties are cyclodextrin moieties or cucurbituril moieties, as show below. Linking groups can be attached to the macrocyclic moieties as described in more detail below. As non-limiting examples, cyclodextrin moieties can be covalently linked to solid support materials via cyclodextrin hydroxyl groups while cucurbituril moieties can be covalently linked to solid support materials via cucurbituril carbonyl groups. Alternatively, the macrocyclic moieties can be physically entrapped in (or otherwise non-covalently associated with) the solid support materials.

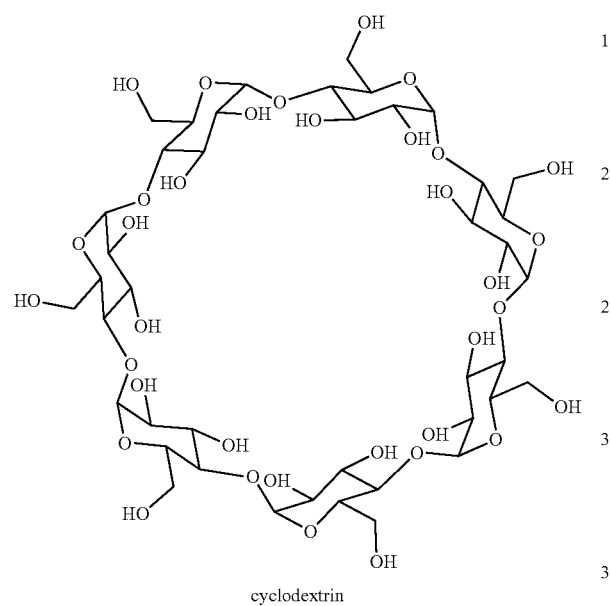

cyclodextrin

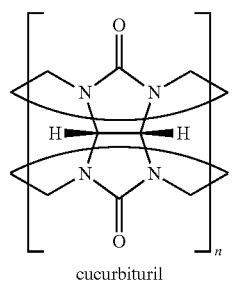

cucurbituril

Accordingly, some embodiments of the invention provide methods for preparing defined protein conjugates as defined above, wherein the macrocyclic matrix material includes a plurality of cyclodextrin moieties. α-Cyclodextrins (having six glucose units), β-cyclodextrins (having seven glucose units) and γ-cyclodextrins (having eight glucose units), and combinations thereof can be used in the matrix materials. In certain embodiments, the cyclodextrin moieties are β-cyclodextrin moieties. In some such embodiments, the cyclodextrin moiety includes a structure according to Formula VI:

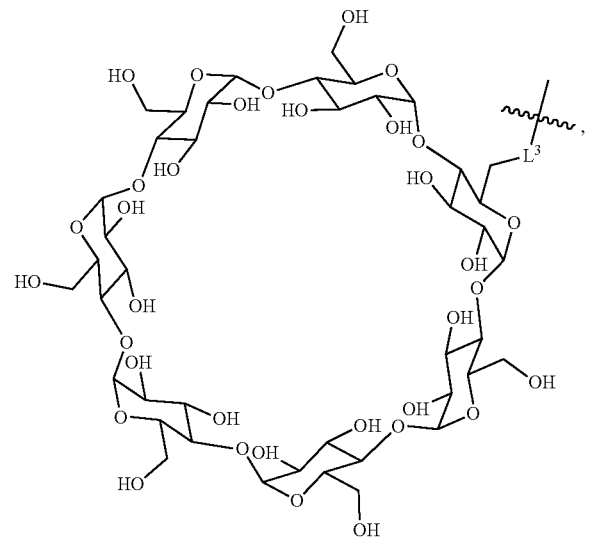

(VI)

wherein $L^3$ is a linking moiety, and
the wavy line represents the connection point to the matrix material.

A number of linking moieties can be used for linking the cyclodextrin to the matrix material. In general, the linking moiety connects two groups and has a backbone. In some cases, the backbone of the linker is 100 atoms or less in length, such as 50 atoms or less, or 20 atoms or less in length. In other cases, the backbone of the linker is 100 atoms or greater in length. A linker or linkage can be a covalent bond that connects two groups or a chain of between 1 and 100 atoms in length, such as between 1 and 50 atoms in length or 1 and 20 atoms in length, for example of about 1, 2, 3, 4, 5, 6, 8, 10, 12, 14, 16, 18 or 20 carbon atoms in length, where the linker can be linear, branched, cyclic, or a single atom. In certain cases, one, two, three, four or five or more carbon atoms of a linker backbone can be optionally replaced with a sulfur, nitrogen or oxygen heteroatom. The bonds between backbone atoms can be saturated or unsaturated; typically, not more than one, two, or three unsaturated bonds will be present in a linker backbone. The linker can include one or more substituent groups (e.g., an alkyl group, an aryl group, or an alkenyl group). A linker can include, without limitation, oligo(ethylene glycol); ethers; thioethers; tertiary amines; and alkyls, which can be straight or branched (e.g., methyl, ethyl, n-propyl, isopropyl, n-butyl, n-pentyl, tert-butyl, and the like. The linker backbone can include a cyclic group, for example, an aryl group, a heterocyclic group, or a cycloalkyl group, where 2 or more atoms, e.g., 2, 3 or 4 atoms, of the cyclic group are included in the backbone. A linker can be peptidic or non-peptidic. A linker can be cleavable or non-cleavable. Further linkers include but are not limited to those described in Hermanson, *Bioconjugate Techniques* 2nd Edition, Academic Press, 2008.

In some embodiments the linking moiety in structures according to Formula VI includes the grouping -$L^{3a}$-$L^{3b}$-, wherein $L^{3a}$ and $L^{3b}$ are independently selected from a bond, a divalent polymer moiety, and linear or branched, saturated or unsaturated $C_{1-30}$ alkyl; wherein one or more carbon atoms in the $C_{1-30}$ alkyl is optionally and independently replaced by O, S, $NR^a$; wherein two or more groupings of adjacent carbon atoms in the $C_{1-30}$ alkyl are optionally and independently replaced by —$NR^a(CO)$— or —$(CO)NR^a$—; and wherein two or more groupings of adjacent carbon atoms in the $C_{1-30}$ alkyl are optionally and independently replaced by a 4- to 8-membered, divalent carbocycle or a 4- to 8-membered, divalent heterocycle having one to four heteroatoms selected from O, S, and N; and each $R^a$ is independently selected from H and $C_{1-6}$ alkyl.

In some embodiments, the linker contains a divalent polymer moiety, such as a divalent poly(ethylene glycol) moiety or a divalent poly(propylene glycol) moiety. In some embodiments, three adjacent carbon atoms in the $C_{1-30}$ alkyl are replaced by a divalent divalent heterocycle such as a divalent triazole. In some embodiments, at least one grouping of adjacent carbon atoms in the linker are replaced by —$NR^a(CO)$— or —$(CO)NR^a$— to form an amide linkage, such as:

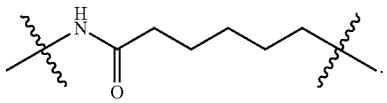 [SMILES: *CCCCCC(=O)N*]

In some embodiments, the cyclodextrin moiety contains a structure according to Formula VIa:

U.S. Pat. Nos. 5,645,717 and 6,423,666. Support materials for macrocylic host moieties further include organic monolith materials (e.g., polymeric monoliths as described in U.S. Pat. No. 7,431,888) and inorganic monolith materials (e.g., silica monoliths as described in U.S. Pat. No. 6,210,570).

Accordingly, some embodiments of the invention provide methods as described above, wherein the macrocyclic matrix material includes a support selected from a crosslinked polysaccharide, a porous silica gel, a mineral oxide hydrogel composite, a silica hydrogel composite, a bis-acrylamide copolymer, an acrylamide-poly(ethylene glycol) copolymer, a monolithic support, and combinations thereof. In some such embodiments, the macrocyclic matrix material includes crosslinked agarose, crosslinked dextran, or a combination thereof. In some embodiments, the macrocyclic matrix material includes a non-ionizable cross-linked agarose resin (e.g., Sepharose CL-4B).

The macrocyclic matrix material can contain any amount of the macrocyclic host moiety suitable for separating modified proteins. In general, the concentration of the macrocyclic host moiety in the matrix will range from about 1 μM to about 10 mM. For example, the concentration of the host moiety in the matrix can range from about 1 μM to about 10 μM, or from about 10 μM to about 100 μM, or from about 100 μM to about 1 mM, or from about 1 mM to about 10 mM. The concentration of the host moiety in the matrix can (VIa)

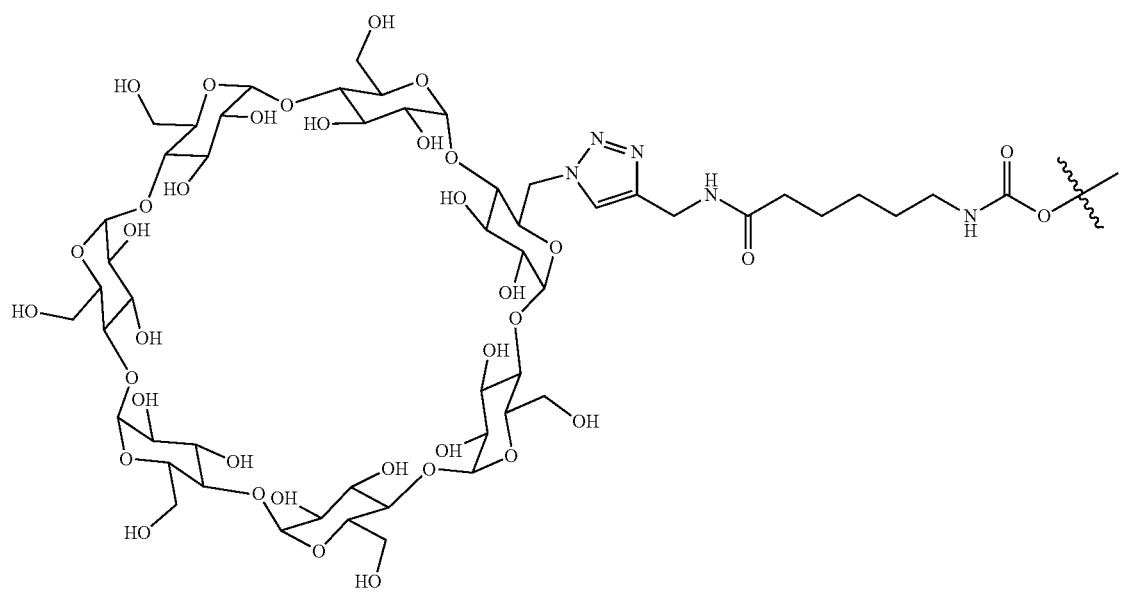

A number of support materials can be used for the macrocyclic host moieties in the methods of the invention. Examples of such support materials include cross-linked polysaccharide resins such as cross-linked dextran beads (e.g., Sephadex, Sephacryl) and cross-linked agarose beads (e.g., Sepharose). These and other polysaccharide resins are described, for example, in U.S. Pat. Nos. 4,094,833 and 4,665,164. Suitable support materials also include silica-based materials, including porous silica gel and silica hydrogel composite materials. Silica gel hydrogel composites are described, for example, in U.S. Pat. Nos. 5,268,097 and 5,445,732. Bis-acrylamide copolymers can also be used as support materials for macrocylic host moieties in the methods of the invention, examples of which are described in range from about 1 μM to about 100 μM, or from about 20 μM to about 80 μM, or from about 40 μM to about 60 M. The concentration of the host moiety in the matrix can range from about 100 μM to about 5 mM, or from about 250 μM to about 4.75 mM, or from about 500 μM to about 4.5 mM, or from about 750 μM to about 4.25 mM, or from about 1 mM to about 4 mM, or from about 1.25 to about mM 3.75 mM, or from about 1.5 mM to about 3.5 mM, or from about 1.75 mM to about 3.25 mM, or from about 2 mM to about 3 mM, or from about 2.25 mM to about 2.75 mM. The concentration of macrocyclic moiety in the matrix can be 1, 2, 3, 4, 5, 6, 7, 8, 9, or 10 mM. Some embodiments of the invention provides methods for preparing protein conjugates having a defined number of conjugate groups as described above, wherein the concentration of the macrocyclic moieties in the macrocyclic matrix material is around 1 mM.

Typically, the separation steps in the methods of the invention will be conducted using conventional equipment and instrumentation for column chromatography. Such instrumentation is described, for example, in U.S. Pat. Nos. 8,986,543; 7,208,087; and 4,563,275. Typically, around 1 gram of the macrocyclic matrix material will be used for separation mixtures of modified protein in amounts ranging from micrograms to milligrams. For example, a chromatography column can be loaded with 1 μg-100 mg protein per gram of the macrocyclic matrix material. The loading capacity of the matrix will depend on factors such as the identity of the protein in the mixture, the level of modification, and the identity of the handle moiety. After loading, the protein can be eluted from the macrocyclic matrix material by passing an aqueous buffer (or another fluid mobile phase) through the column. Any suitable flow-rate for separating the modified proteins can be used, and flow-rates ranging from 0.1-5 mL/min can be employed depending on factors such as the quantity of protein and the dimensions of the column and ancillary equipment. Any buffer compatible with the protein and the macrocyclic matrix material can be used in the methods of the invention. Examples of suitable buffers include 2-(N-morpholino)ethanesulfonic acid (MES), 2-[4-(2-hydroxyethyl)piperazin-1-yl]ethanesulfonic acid (HEPES), 3-morpholinopropane-1-sulfonic acid (MOPS), 2-amino-2-hydroxymethyl-propane-1,3-diol (TRIS), potassium phosphate, sodium phosphate, phosphate-buffered saline, sodium citrate, sodium acetate, and sodium borate. Such buffers will typically be used at concentrations ranging from around 1 mM to about 250 mM, and the pH of the buffers will typically range between around 5.5 and 8. One of skill in the art will appreciate that the concentration and/or pH of the buffer can be adjusted depending on the properties of the protein being separated. The buffer used in the separation step can also include cosolvents, detergents/surfactants, chelators, and reducing agents, as described above.

Typically, the buffer used in the separation step will also include an elution compound that promotes unbinding of the modified protein from the matrix material. For example, the elution compound can be a salt (e.g., NaCl, KCl, CaCl$_2$, MgSO$_4$, (NH$_4$)$_2$SO$_4$) or a competitive guest substance that binds to the matrix or modified protein (e.g., adamantane carboxylic acid, soluble cyclodextrin). The buffer used in the separation step can contain β-cyclodextrin in solution at a concentration ranging from around 100 μM to around 100 mM. In some embodiments, the buffer used in the separation step contains β-cyclodextrin in solution at a concentration of 10 mM. In some embodiments, the buffer used in the separation step contains pH 6.5 phosphate buffer and 10 mM β-cyclodextrin. The separation steps will typically be conducted at or below room temperature. For example, the separation can be conducted at around 25° C., or around 20° C., or around 8° C., or around 4° C.

Accordingly, some embodiments of the invention provide methods for preparing a protein conjugate having a defined number of conjugate groups as described above, wherein forming the mixture and eluting the proteins include introducing the plurality of proteins into a column containing the macrocyclic matrix material and passing a buffer solution through the column.

E. Proteins for Forming Defined Bioconjugates

Any protein that is compatible with the bioconjugation methods disclosed herein can be modified according to the invention. Non-limiting examples of proteins suitable for us in the methods of the invention include structural proteins (e.g., actin, actinin, aggrecan, biglycan, cadherin, collagen, decorin, elastin, fibrinogen/fibrin, fibronectin, heparan, keratin, laminin, mucin, myelin associated glycoprotein, myelin basic protein, myosin, spectrin, tropomyosin, troponin, tubulin, vimentin, vitronectin), transport proteins (e.g., a transmembrane pump, channel, or transporter), targeting proteins (e.g., an antibody or antibody fragment), hormone proteins (e.g., insulin, luteinizing hormone, platelet-derived growth factor), and enzymes (e.g., proteases, nucleases, kinases, phosphatases, phosphodiesterases, nucleotide cyclases). In some embodiments, the protein is selected from a structural protein, a transport protein, a targeting protein, a hormone protein, and an enzyme. In some embodiments, the protein is an enzyme.

In some embodiments, the invention provides a method for preparing a protein conjugate having a defined number of conjugate groups as described above, wherein the method includes:

i) forming a mixture containing a macrocyclic matrix material and a plurality of proteins, wherein:
  each protein in a first population of proteins in the plurality has a first number of handle moieties,
  each protein in a second population of proteins in the plurality has a second number of handle moieties,
  each of the handle moieties has a structure according to Formula Ib:

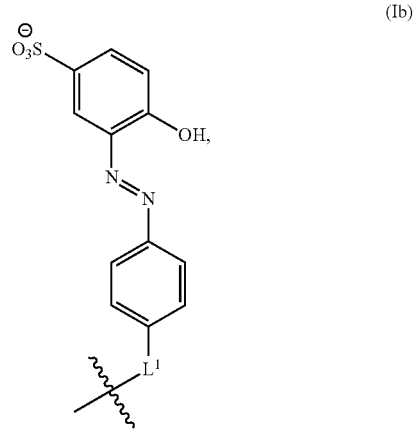

(Ib)

wherein L$^1$ is a linking moiety as described above,
the macrocyclic matrix material includes a crosslinked agarose support and a plurality of cyclodextrin moieties having a structure according to Formula VIa:

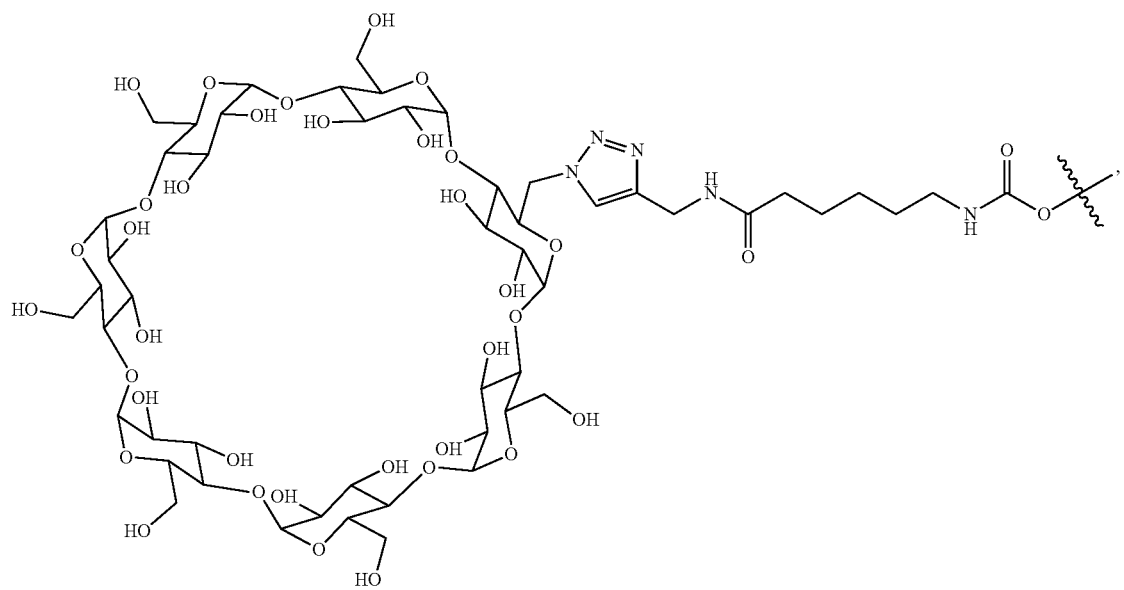

(VIa)

and the mixture is formed under conditions sufficient to bind the modified proteins to the macrocyclic matrix material, ii) eluting the proteins from the macrocyclic matrix material to obtain a first separated protein fraction and a second separated protein fraction, wherein:

substantially all (i.e., at least 50, 55, 60, 65, 70, 75, 80, 85, 90, 95, or 99% (w/w)) of the proteins in the first separated protein fraction have the first number of handle moieties, and substantially all (i.e., at least 50, 55, 60, 65, 70, 75, 80, 85, 90, 95, or 99% (w/w)) of the proteins in the second separated protein fraction have the second number of handle moieties;

iii) contacting the handle moieties with sodium dithionite under conditions sufficient to convert the handle moieties in the first separated protein fraction to reactive moieties having a structure according to Formula IIa:

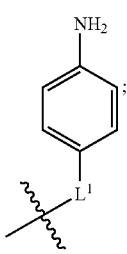

(IIa)

and iv) contacting the reactive moieties with a conjugation reagent having a structure according to Formula IIIa:

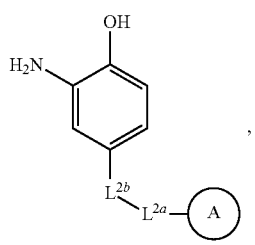

(IIIa)

wherein $L^{2a}$, $L^{2b}$, and A are as described above, in the presence of potassium ferricyanide under conditions sufficient to form a plurality of protein conjugates containing conjugate groups having a structure according to Formula IV:

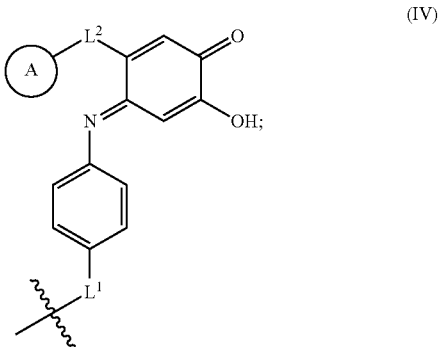

(IV)

wherein substantially all (i.e., at least 50, 55, 60, 65, 70, 75, 80, 85, 90, 95, or 99% (w/w)) of the protein conjugates in the plurality have the same number of conjugate groups; thereby preparing the protein conjugate.

IV. Methods for Protein Recovery and Recycling

Figure 16:
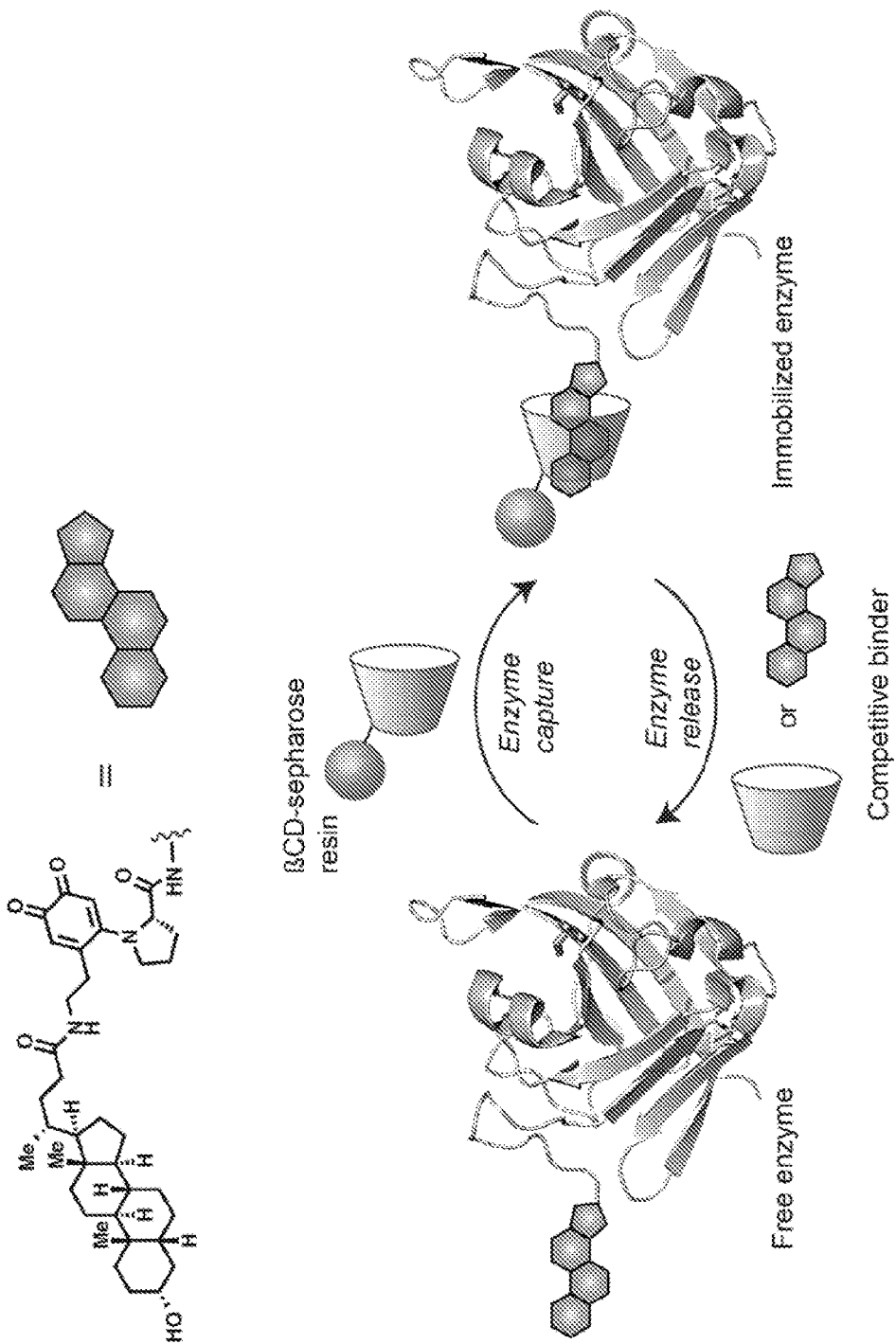
FIG. 16 shows a scheme for enzyme recycling according to the methods of the invention. An enzyme modified with lithocholic acid selectively binds β-cyclodextrin-functionalized resin and is released by addition of excess β-cyclodextrin or lithocholic acid.

Given the high costs of many enzymes used in laboratory and industrial endeavors, there has been substantial effort to reduce the overall amount of enzymes required in biochemical transformations by recycling enzymes after use. A number of strategies have been developed for recycling of enzymes (e.g., by attaching them to insoluble particles or surfaces). Such immobilized enzymes can perform better or worse than free enzymes depending on the particular enzyme used and reaction conditions employed. Disclosed herein is an alternative method of recovering enzymes and other proteins from complex mixtures (e.g., enzyme reaction mixtures). The method is based on affinity interactions, wherein the protein is modified with a small molecule handle that minimally affects the properties of the protein. The method proceeds as illustrated in FIG. 16, where the enzyme is modified with a small molecule handle so as to minimally affect its diffusional freedom. After a reaction is complete, addition of beads bearing a binding partner of the affinity group on the enzyme allows for removal of the enzyme from solution. Because many enzymes are used in the context of heterogeneous mixtures, the beads can be magnetized to enable their separation from other insoluble components of the mixture. The enzyme-bead complexes can then be isolated and the enzyme liberated for future use.

Accordingly, another aspect of the invention provides a method for conducting an enzymatic reaction. The method includes:
a) forming a reaction mixture containing an enzyme and an enzyme substrate, wherein the enzyme has a prosthetic guest moiety, under conditions sufficient to convert the enzyme substrate to a product;
b) adding a matrix material containing a macrocyclic host moiety to the reaction mixture under conditions sufficient to form an enzyme-matrix host-guest complex; and
c) recovering the enzyme-matrix host-guest complex from the reaction mixture;
thereby conducting the enzymatic reaction.

In some embodiments, the method further includes eluting the enzyme from the enzyme-matrix host-guest complex and reusing the enzyme.

In a related aspect, the invention provides a method for isolating a protein. The method includes:
i) forming a mixture containing a matrix material and a protein conjugate, wherein:
the matrix material contains a macrocyclic host moiety,
the protein conjugate has a prosthetic guest moiety, and
the mixture is formed under conditions sufficient to form a protein-matrix host-guest complex; and
ii) recovering the protein-matrix host-guest complex from the mixture;
thereby isolating the protein.

A. Guest Moieties for Protein Recovery Methods

Thermodynamic properties of macrocyclic host guest complexes are discussed above with respect to chromatography methods, and these principals apply to the protein recovery methods disclosed herein. Examples of prosthetic guest moieties include, but are not limited to, bile acids (as shown below, wherein $R^5$ is H or —$CH_3$ and $R^6$ is H or —OH) adamantanes, stilbenes (including cis-stilbenes and trans-stilbenes), azobenzenes, ferrocenes, p-xylylenediammoniums (as shown below, wherein each $R^8$ is independently H or $C_{1-4}$ alkyl), pyridiniums (as shown below, wherein $R^8$ is H or $C_{1-4}$ alkyl), bi-pyridiniums (including 4,4'-bipyridiniums, as shown below wherein each $R^8$ is independently H or $C_{1-4}$ alkyl, and 2,2'-bipyridiniums), and triazoles (including 1,2,3-triazoles and 1,2,4-triazoles). Linking groups can be attached to the prosthetic guest moieties as described in more detail below. As non-limiting examples, linking groups for modification of proteins can be appended to a bile acid or adamantane carboxylic acid via amide bond formation at the carboxylate group, and linking groups for modification of proteins can be appended to a stilbene or azobenzene via nucleophilic aromatic substitution. Bile acids, adamantanes, stilbenes, azobenzenes, ferrocenes, p-xylylenediammoniums, pyridiniums, bi-pyridiniums, and triazoles, as shown below, can be further substituted with one or more (e.g., 1-3 or 1-6) $R^9$ moieties, which can be independently selected from halo, hydroxy, amino, alkylamino, amido, acyl, nitro, cyano, and alkoxy.

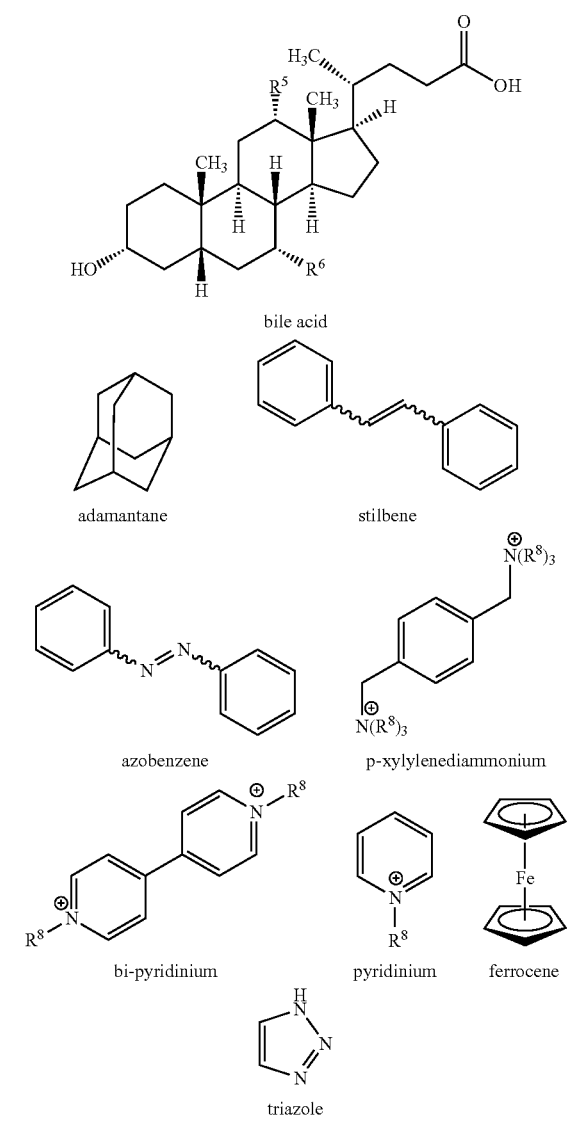

In some embodiments, the prosthetic guest moiety includes a bile acid group, an adamantane group, a stilbene group, an azobenzene group, a ferrocene group, a p-xylylenediammonium group, a pyridinium group, a bi-pyridinium group, a triazole group, or a combination thereof. In some embodiments, the prosthetic guest moiety includes a bile acid group, an adamantane group, or a stilbene group. In some embodiments, the prosthetic guest moiety includes a bile acid group.

In general, dissociation constants ($K_a$) for host guest complexes formed by the macrocyclic host moieties and protein conjugates in the protein recovery method will range from about 10 $M^{-1}$ to about $10^{10}$ $M^{-1}$. In some embodiments, the dissociation constant $K_a$ for the host guest complex ranges from about $10^3$ $M^{-1}$ to about $10^7$ $M^{-1}$. In some embodiments, the dissociation constant $K_a$ for the host guest complex ranges from about $10^5$ $M^{-1}$ to about $10^7$ $M^{-1}$. In some embodiments, the dissociation constant $K_a$ for the host guest complex is about $10^6$ $M^{-1}$. In the case of stilbene guest moieties and β-cyclodextrins, binding constants can be determined in a buffer (e.g., 25 mM pH 8.0 phosphate buffer) by monitoring absorbance between 240 nm and 365. Under these conditions, useful host guest/guest complexes have exhibited binding constants ranging from about $10^6$ $M^{-1}$ to about $10^7$ $M^{-1}$ (e.g., $10^{6.6}$ $M^{-1}$).

In some embodiments, the prosthetic guest moiety includes a bile acid group, an adamantane group, a stilbene group, an azobenzene group, a ferrocene group, a p-xylylenediammonium group, a pyridinium group, a bi-pyridinium group, a triazole group, or a combination thereof. In some embodiments, the prosthetic guest moiety includes a bile acid group, an adamantane group, or a stilbene group.

In some embodiments, the prosthetic guest moiety includes a structure according to Formula VII:

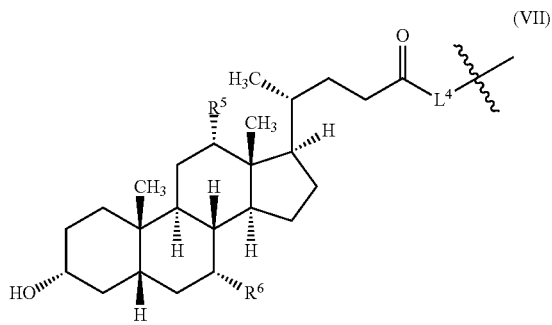

(VII)

wherein:
$R^5$ is selected from H and —CH$_3$,
$R^6$ is selected from H and —OH, and
$L^4$ is a linking moiety.

In some embodiments, the linking moiety includes a structure selected from:

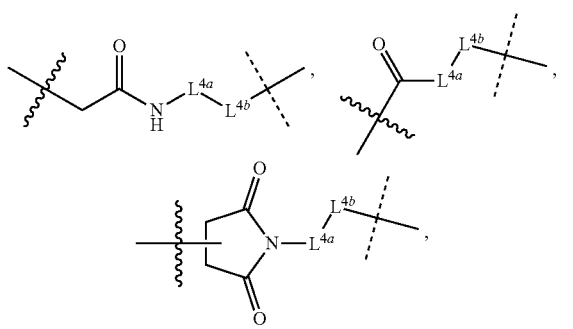

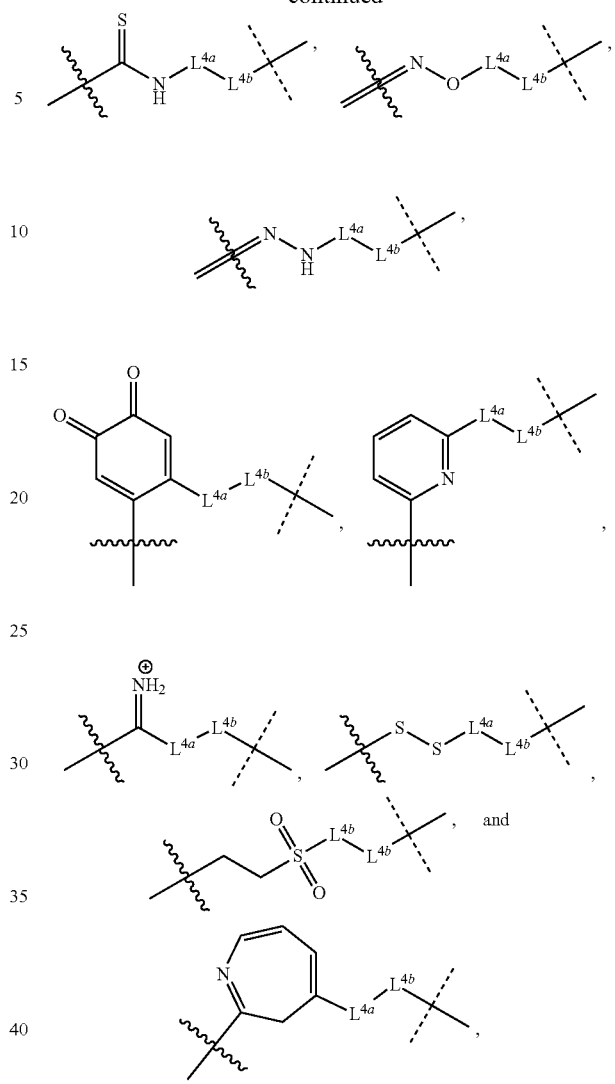

wherein:
$L^{4a}$ and $L^{4b}$ are independently selected from a bond, a divalent polymer moiety, and linear or branched, saturated or unsaturated $C_{1-30}$ alkyl; wherein one or more carbon atoms in the $C_{1-30}$ alkyl is optionally and independently replaced by O, S, NR$^a$; wherein two or more groupings of adjacent carbon atoms in the $C_{1-30}$ alkyl are optionally and independently replaced by —NR$^a$(CO)— or —(CO)NR$^a$—; and wherein two or more groupings of adjacent carbon atoms in the $C_{1-30}$ alkyl are optionally and independently replaced by a 4- to 8-membered, divalent carbocycle or a 4- to 8-membered, divalent heterocycle having one to four heteroatoms selected from O, S, and N;

each R$^a$ is independently selected from H and $C_{1-6}$ alkyl;

the wavy line represents the point of connection to the protein; and the dashed line represents the point of connection to the structure of Formula VII.

In some embodiments, the prosthetic guest moiety includes a structure according to Formula VIIa:

(VIIa)

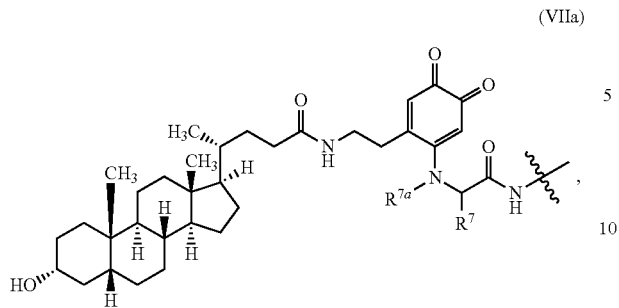

wherein $R^7$ is an amino acid sidechain and $R^{7a}$ is H, or $R^7$ and $R^{7a}$ are taken together to form a proline sidechain, and the wavy line represents the point of connection to the protein.

In structures according to Formula VIIa, the grouping VIIa' can be formed via reaction of a protein N-terminus with an aminophenol compound as described herein.

(VIIa')

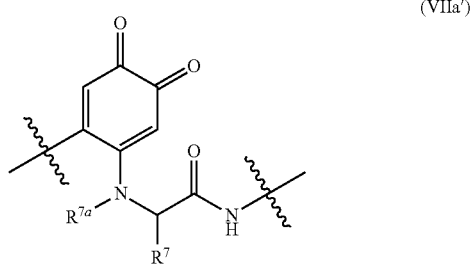

In some embodiments, the prosthetic guest moiety includes a structure according to Formula VIIb:

(VIIb)

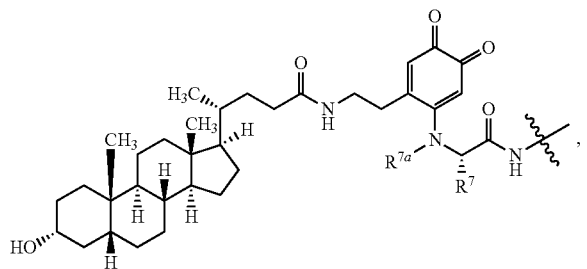

wherein $R^7$ is an amino acid sidechain and $R^{7a}$ is H, or $R^7$ and $R^{7a}$ are taken together to form a proline sidechain, and the wavy line represents the point of connection to the protein.

In some embodiments, the prosthetic guest moiety includes a structure according to Formula VIIc:

(VIIc)

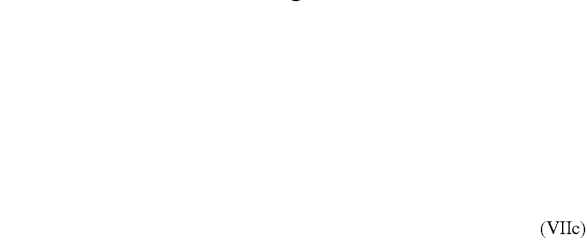

wherein the wavy line represents the point of connection to the protein.

In some embodiments, the prosthetic guest moiety includes a structure according to Formula VIId:

(VIId)

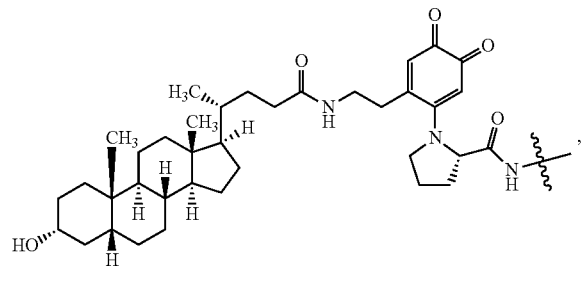

wherein $R^7$ is an amino acid sidechain, and the wavy line represents the point of connection to the protein.

In structures according to Formula VIId, the grouping VIId' can be formed via reaction of a protein N-terminus with a pyridine carboxaldehyde compound as described herein.

(VIId')

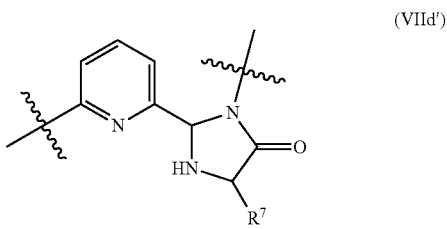

In some embodiments, the prosthetic guest moiety includes a structure according to Formula VIIe:

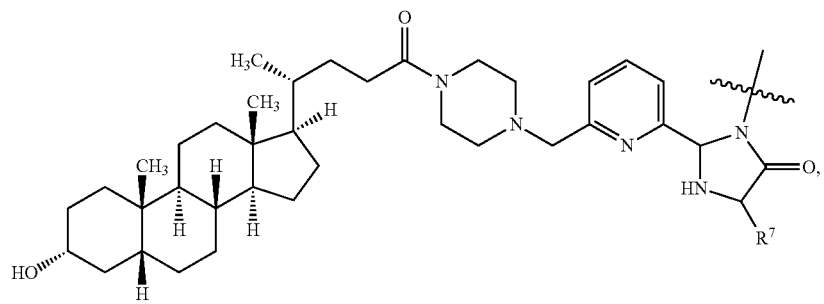

(VIIe)

wherein R[7] is an amino acid sidechain, and
the wavy line represents the point of connection to the protein.

In some embodiments, the prosthetic guest moiety includes an adamantane group according to the formula:

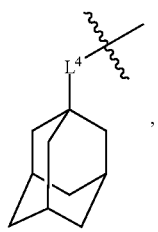

wherein L[4] is a linking moiety as described above and the wavy line represents the point of connection to the protein.

In some embodiments, the prosthetic guest moiety includes a stillbene group according to the formula:

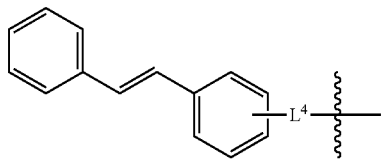

or the formula:

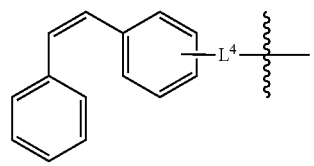

wherein L[4] is a linking moiety as described above; the wavy line represents the point of connection to the protein; and the stilbene moiety is optionally substituted with 1-4 substituents selected from the group consisting of —OR[a], —N(R[a])₃, —SO₃H, and —CO₂H or salts thereof, wherein each R[a] is independently selected from H and C$_{1-6}$ alkyl.

B. Matrix Materials and Protein Recovery

Any support material and host moiety suitable for forming host guest complexes with the modified proteins can be used in the protein recovery methods, including any of the matrix materials discussed above. In some embodiments, the macrocyclic host moiety includes a cyclodextrin group, a cucurbituril group, a calixarene group, a cyclophane group, a resorcinarene group, or a calixpyridine group, as described above. In some embodiments, the macrocyclic host moiety includes a β-cyclodextrin group. In some embodiments, the macrocyclic host moiety includes a structure according to Formula VIII:

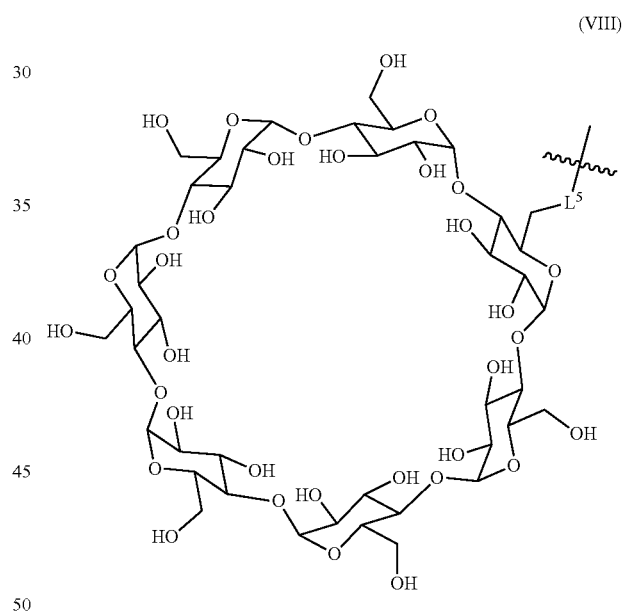

(VIII)

wherein L[5] is a linking moiety, and
and the wavy line represents the connection point to the matrix material.

In some embodiments, the linking moiety includes a grouping -L[5a]-L[5b]-, wherein L[5a] and L[5b] are independently selected from a bond, a divalent polymer moiety, and linear or branched, saturated or unsaturated C$_{1-30}$ alkyl; wherein one or more carbon atoms in the C$_{1-30}$ alkyl is optionally and independently replaced by O, S, NR[a]; wherein two or more groupings of adjacent carbon atoms in the C$_{1-30}$ alkyl are optionally and independently replaced by —NR[a](CO)— or —(CO)NR[a]—; and wherein two or more groupings of adjacent carbon atoms in the C$_{1-30}$ alkyl are optionally and independently replaced by a 4- to 8-membered, divalent carbocycle or a 4- to 8-membered, divalent heterocycle having one to four heteroatoms selected from O, S, and N.

In some embodiments, the macrocyclic host moiety includes a structure according to Formula VIIIa:

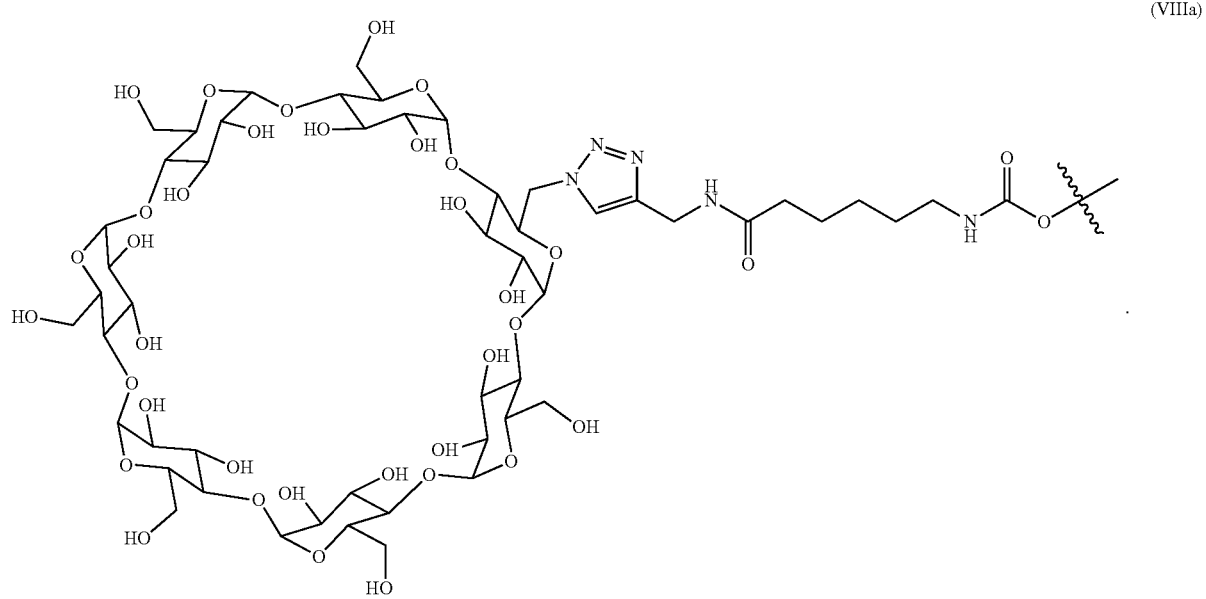 [SMILES: *OC(=O)NCCCCCC(=O)NCc1cn(CC2OC3OC4C(CO)OC(OC5C(CO)OC(OC6C(CO)OC(OC7C(CO)OC(OC8C(CO)OC(OC9C(CO)OC(OC2C(O)C3O)C(O)C9O)C(O)C8O)C(O)C7O)C(O)C6O)C(O)C5O)C(O)C4O)nn1]

(VIIIa)

In some embodiments, the matrix material includes a support selected from a crosslinked polysaccharide, a porous silica gel, a mineral oxide hydrogel composite, a silica hydrogel composite, a bis-acrylamide copolymer, an acrylamide-poly(ethylene glycol) copolymer, and combinations thereof. In some embodiments, the support includes crosslinked agarose, crosslinked dextran, or a combination thereof. In some embodiments, the concentration of the macrocyclic host moiety in the matrix material is around 1 mM.

The separation steps in the protein recovery methods is straightforward. Mixtures containing the modified enzyme (or other protein) can contain buffers, cosolvents, detergents/surfactants, chelators, and/or reducing agents, as described above. Typically, around 1 gram of the macrocyclic matrix material will be used for recovering a modified enzyme or other modified protein in amounts ranging from micrograms to milligrams. For example, the methods can be used to recover 1 μg-100 mg protein per gram of the macrocyclic matrix material. Any buffer compatible with the protein and the macrocyclic matrix material can be used in the methods of the invention. Examples of suitable buffers include 2-(N-morpholino)ethanesulfonic acid (MES), 2-[4-(2-hydroxyethyl)piperazin-1-yl]ethanesulfonic acid (HEPES), 3-morpholinopropane-1-sulfonic acid (MOPS), 2-amino-2-hydroxymethyl-propane-1,3-diol (TRIS), potassium phosphate, sodium phosphate, phosphate-buffered saline, sodium citrate, sodium acetate, and sodium borate. Such buffers will typically be used at concentrations ranging from around 1 mM to about 250 mM, and the pH of the buffers will typically range between around 5.5 and 8. One of skill in the art will appreciate that the concentration and/or pH of the buffer can be adjusted depending on the properties of the protein being recovered.

Isolation of the host guest complexes containing enzyme or other protein from protein mixtures can be conducted via established techniques such as centrifugation, filtration, the use of magnets, or combinations of such techniques. After isolation of the matrix material, the enzyme or other protein can be eluted from the macrocyclic matrix material by incubating an aqueous buffer (or another fluid) with the matrix material. As described above in the context of affinity chromatography, the buffer will typically include an elution compound that promotes unbinding of the modified protein from the matrix material. For example, the elution compound can be a salt (e.g., NaCl, KCl, $CaCl_2$, $MgSO_4$, $(NH_4)_2SO_4$) or a competitive guest substance that binds to the matrix or modified protein (e.g., adamantane carboxylic acid, soluble cyclodextrin). The buffer used in the elution step can contain β-cyclodextrin in solution at a concentration ranging from around 100 μM to around 100 mM. In some embodiments, the buffer used in the elution step contains β-cyclodextrin in solution at a concentration of 10 mM. Binding and elution separation steps will typically be conducted at or below room temperature. For example, the separation can be conducted at around 25° C., or around 20° C., or around 8° C., or around 4° C.

Accordingly, some embodiments of the invention provide methods wherein recovering the host-guest complex includes centrifuging the mixture, filtering the mixture, or centrifuging and filtering the mixture. In some embodiments, the method further includes eluting the protein from protein-matrix host-guest complex after recovering the protein-matrix host-guest complex. Proteins recovered from reaction mixtures are suitable for recycling (i.e., re-use) in additional enzymatic reactions. Enzymes can be used and recycled twice, three times, four times, five times, or more.

Non-limiting examples of proteins suitable for use in the protein recovery methods include structural proteins (e.g., actin, actinin, aggrecan, biglycan, cadherin, collagen, decorin, elastin, fibrinogen/fibrin, fibronectin, heparan, keratin, laminin, mucin, myelin associated glycoprotein, myelin basic protein, myosin, spectrin, tropomyosin, troponin, tubulin, vimentin, vitronectin), transport proteins (e.g., a transmembrane pump, channel, or transporter), targeting proteins (e.g., an antibody or antibody fragment), hormone proteins (e.g., insulin, luteinizing hormone, plate-derived growth factor), and enzymes (e.g., proteases, nucleases, kinases, phosphatases, phosphodiesterases, nucleotide cyclases). In some embodiments, the protein is selected from a structural protein, a transport protein, a targeting protein, a hormone protein, and an enzyme. In some embodiments, the protein is an enzyme.

In some embodiments, the invention provides a method for conducting an enzymatic reaction as described above, wherein the method includes:

a) forming a reaction mixture containing an enzyme and an enzyme substrate under conditions sufficient to convert the enzyme substrate to a product, wherein the enzyme includes a prosthetic guest moiety according to any one of Formula VIIa, Formula VIIb, Formula VIIc, Formula VIId, and Formula VIIe

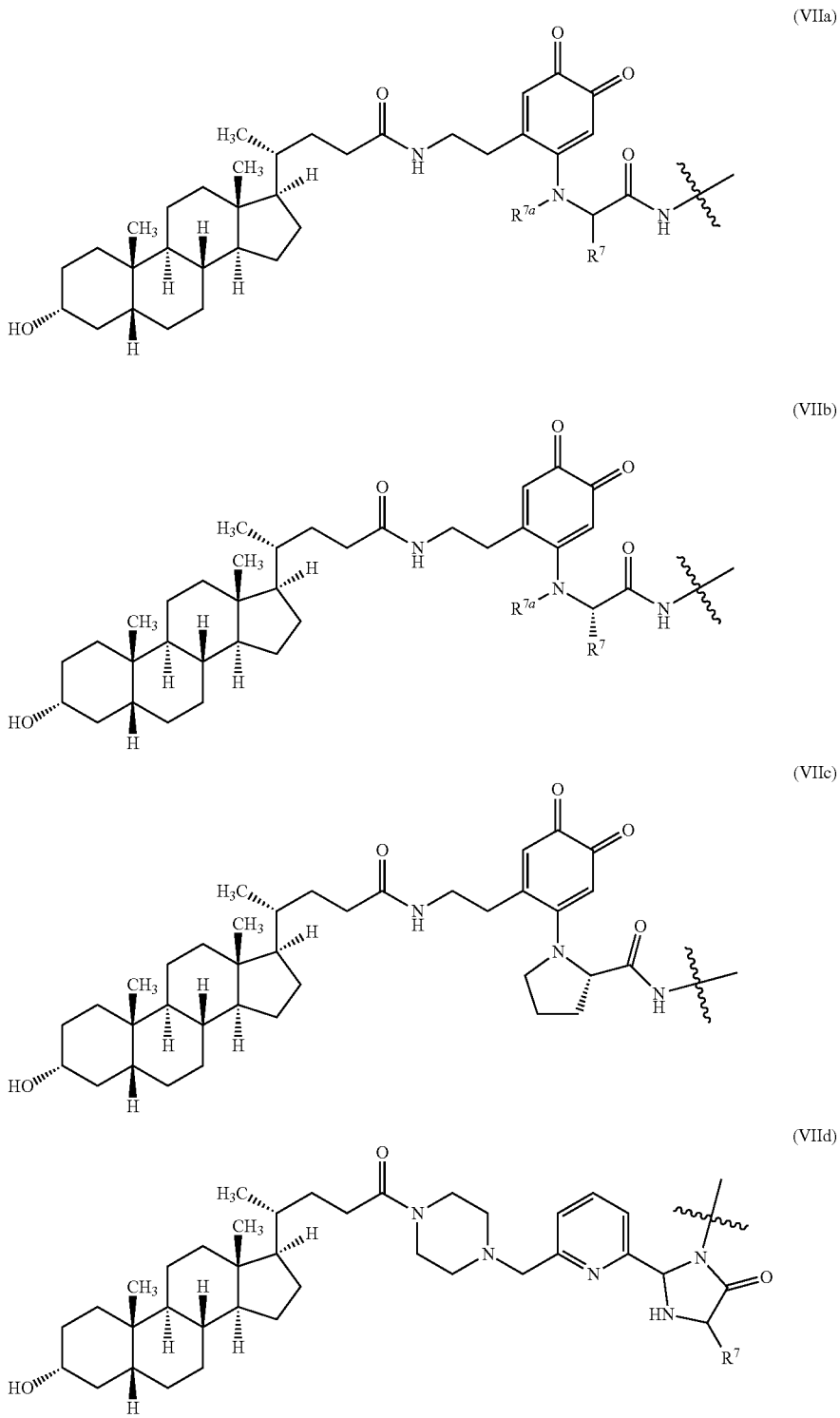

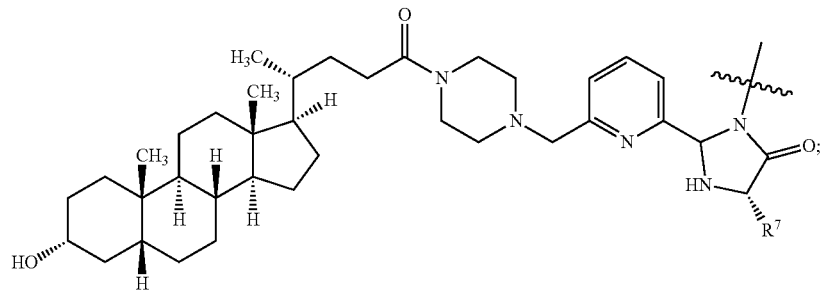
(VIIe)

b) adding a matrix material to the reaction mixture under conditions sufficient to form an enzyme-matrix host-guest complex,
wherein the macrocyclic matrix material includes a cross-linked agarose support and a plurality of cyclodextrin moieties having a structure according to Formula VIIIa:

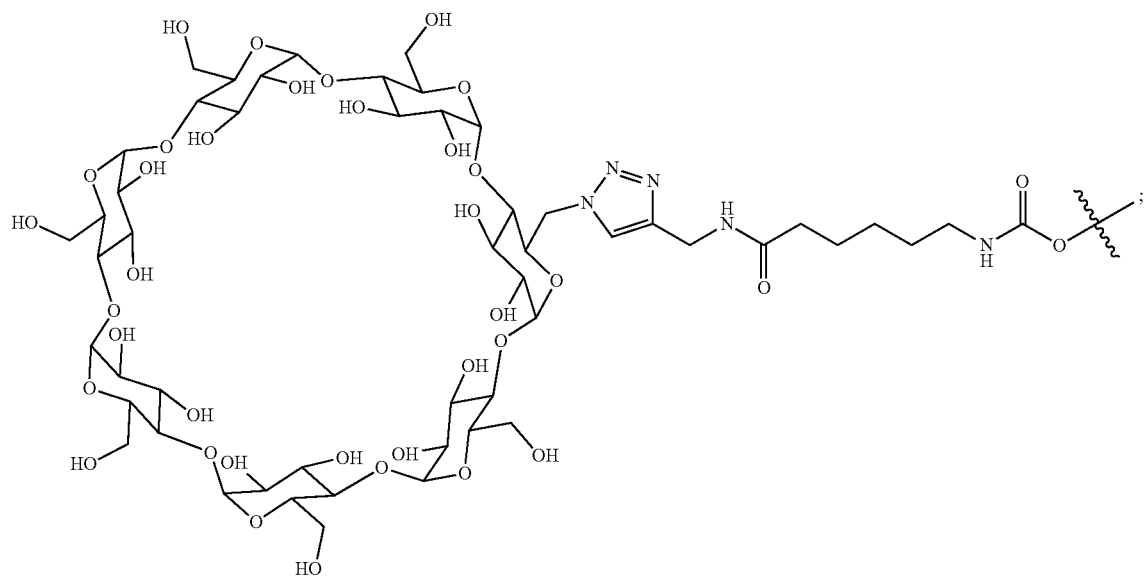
(VIIIa)

and
c) recovering the enzyme-matrix host-guest complex from the reaction mixture;
thereby conducting the enzymatic reaction. In some embodiments, the method further includes reusing the enzyme in subsequent enzymatic reaction steps. In some such embodiments, the method includes eluting the enzyme from the enzyme-matrix host-guest complex and reusing the enzyme in subsequent enzymatic reaction steps.

In some embodiments, the invention provides a method for isolating a protein as described above, wherein the method includes:
i) forming a mixture containing a matrix material and a protein conjugate under conditions sufficient to form a protein-matrix host-guest complex,
wherein the matrix material includes a crosslinked agarose support and a plurality of cyclodextrin moieties having a structure according to Formula VIIIa:

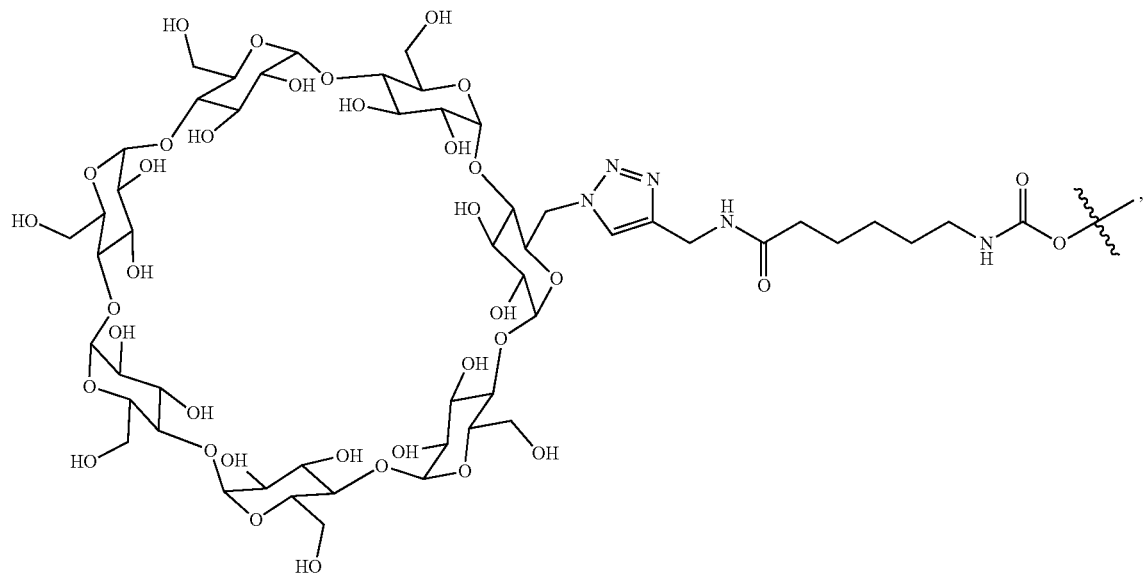
(VIIIa)
and the protein conjugate includes a prosthetic guest moiety according to any one of Formula VIIa, Formula VIIb, Formula VIIc, Formula VIId, and Formula VIIe
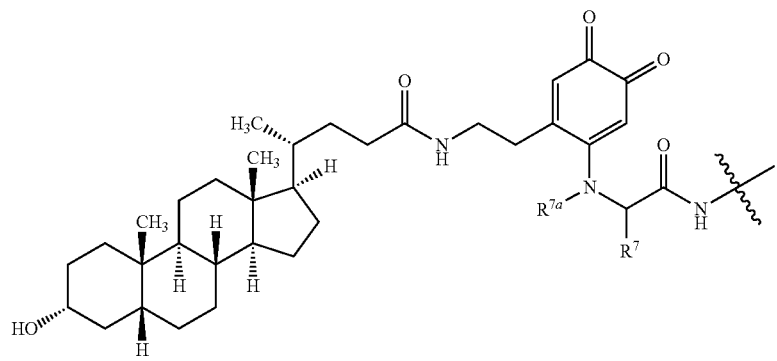
(VIIa)
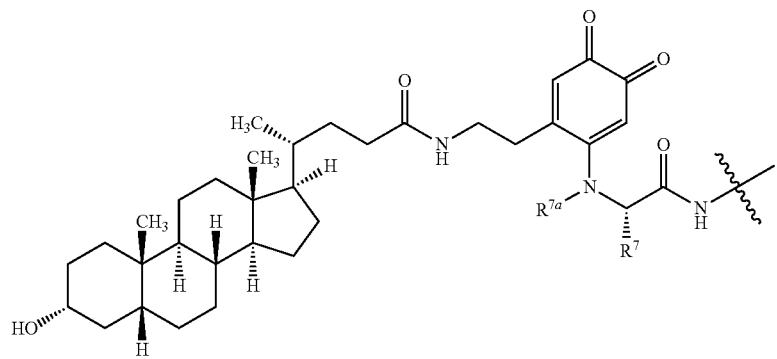
(VIIb)

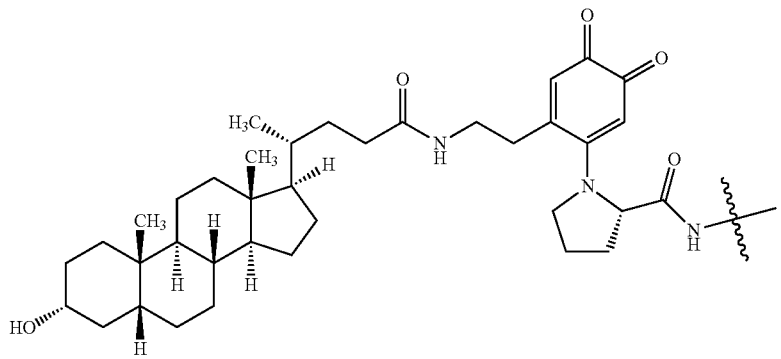

(VIIc)

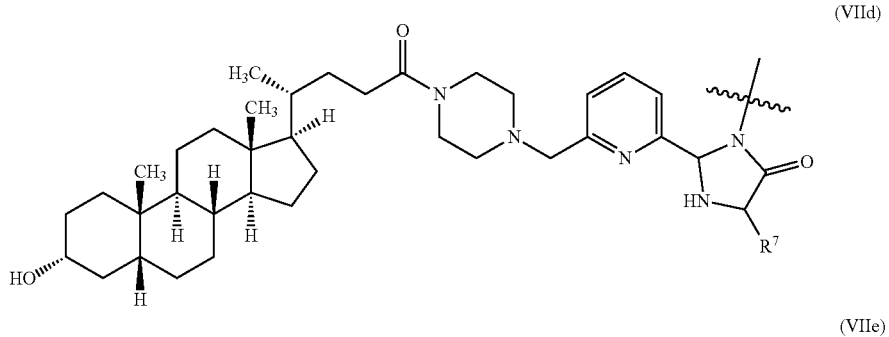

(VIId)

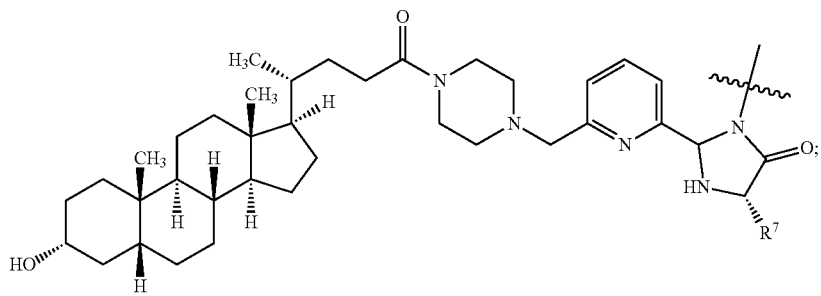

(VIIe)

and ii) recovering the protein-matrix host-guest complex from the mixture;

thereby isolating the protein.

V. Examples

Unless otherwise noted, the chemicals and solvents used were of analytical grade and were used as received from commercial sources. Purications by flash chromatography were performed using EM silica gel 60 (230-400 mesh). Chromatography solvents were used without distillation. All organic solvents were removed under reduced pressure using a rotary evaporator. Water (dd-H2O) used as a reaction solvent was deionized using a Barnstead NANOpure purication system. Centrifugations were performed with an Eppendorf Mini Spin Plus (Eppendorf, Hauppauge, N.Y.).

NMR.

$^1$H and $^{13}$C spectra were recorded with a Bruker AVB-400 (400 MHz, 100 MHz) or a Bruker AV-600 (600 MHz, 150 MHz). 1H NMR chemical shifts are reported as in units of parts per million (ppm) relative to residual CH3OH (δ 3.31, pentet) or DMF (δ 8.03, singlet). Multiplicities are reported as follows: s (singlet), d (doublet), t (triplet), dd (doublet of doublets) or m (multiplet). Coupling constants are reported as a J value in Hertz (Hz). The number of protons (n) for a given resonance is indicated as nH and is based on spectral integration values. 13C NMR chemical shifts are reported as in units of parts per million (ppm) relative to DMF-$d_7$ (δ 163.15, triplet) or MeOH-$d_4$ (δ 49.15, septet).

Mass Spectrometry.

Matrix-assisted laser desorption/ionization time-of-flight mass spectrometry (MALDI-TOF MS) was performed on a Voyager-DE system (PerSeptive Biosystems, USA). Small molecule samples were co-crystallized with -cyano-4-hydroxycinnamic acid in 1:1 acetonitrile (MeCN) to H2O with 0.1% trifluoroacetic acid (TFA). Cyclodextrins were co-crystallized with 2,5-dihydroxybenzoic acid in 1:1 MeCN to H2O with 0.1% TFA. Protein bioconjugates were analyzed using an Agilent 1200 series liquid chromatograph (Agilent Technologies, USA) that was connected in-line with an Agilent 6224 Time-of-Flight (TOF) LC/MS system equipped with an electrospray ion source. Extracted mass spectra were plotted using chartograph.com/ms.

High Performance Liquid Chromatography.

HPLC was performed on Agilent 1100 Series HPLC Systems (Agilent Technologies, USA). Sample analysis for all HPLC experiments was achieved with an in-line diode array detector (DAD) and in-line fluorescence detector (FLD). Analytical reverse-phase HPLC of small molecules was accomplished using a C18 stationary phase and a H2O/MeCN with 0.1% TFA gradient mobile phase.

Fast Protein Liquid Chromatography.

FPLC was performed on an Akta Pure M (GE Healthcare, USA) at 8° C. Sample analysis was performed with an in-line UV monitor and an in-line conductance monitor. All injections were performed manually with a 1 mL syringe fit to the top of the column.

UV-Visible Spectrometry.

UV-visible spectrometry was performed using quartz cuvettes with a Varian Cary 50 spectrophotometer (Agilent, USA). Small-scale UV-visible spectrometry was performed using a Nanodrop 1000 (Thermo Scientific, USA). Absorbance measurements of samples in plates were obtained with a SpectraMaxM2 (Molecular Devices, Sunnyvale, Calif.).

Fluorescence.

Fluorescence measurements were obtained on a Fluoromax-4 spectrofluorometer equipped with automatic polarizers and a Peltier temperature controller (ISA Instruments, USA). Slit widths were set to 1.0 nm for excitation and 0.2 nm for emission. Fluorescence emission was monitored with a 0.2 s integration time. For three-dimensional excitation/emission measurements, the excitation wavelength was scanned from 200-600 nm in 4 nm increments and the fluorescence emission was monitored from 290-600 nm in 2 nm increments.

Example 1. Design and Synthesis of the Affinity Handles for Chromatography

Synthesis of Azo 1.

Figure 10:
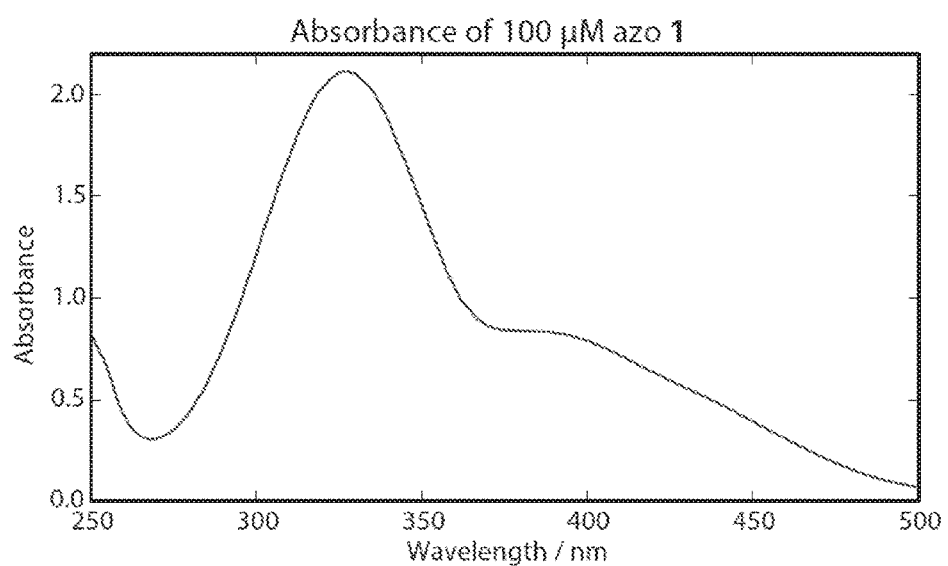
FIG. 10 shows the absorbance spectrum of azo 1.

Sulfanilic acid (1.7 g, 9.83 mmol, 1 eq.) was added to 150 mL of concentrated aqueous HCl in a 250 mL Erlenmeyer ask at 0° C. To this solution was added 0.75 g (10.87 mmol, 1.1 eq.) of sodium nitrite in 10 mL of water, and the reaction was stirred for 30 min. This solution was added dropwise over 1 h to a solution of vigorously stirred 3-(4-hydroxyphenyl)propionic acid (1.8 g, 10.87 mmol, 1.1 eq.) and sodium carbonate (105 g, 1 mol) in 250 mL of 4:1 water:methanol at 0° C. During the addition, the reaction bubbled vigorously and turned bright reddish orange. After the addition was complete, the reaction was stirred for an additional hour at room temperature. The reaction was acidified with concentrated aqueous HCl, at which point the product precipitated as a fine reddish brown solid that was collected via filtration with a 0.2 μm Teflon filter. The resulting material was recrystallized from 3:1 ethanol:water to afford 2.5 g (73%) of material. An absorbance spectrum is shown in FIG. 10. $^1$H NMR (400 MHz, DMF-$d_7$) δ 12.43 (s, 1H), 11.67 (s, 1H), 7.97 (d, J=1.5 Hz, 4H), 7.79 (d, J=2.2 Hz, 1H), 7.40 (dd, J=8.5, 2.2 Hz, 1H), 7.02 (d, J=8.4 Hz, 1H), 2.95 (t, J=7.6 Hz, 2H), 2.69 (t, J=7.5 Hz, 2H). $^{13}$C NMR (100 MHz, DMF-$d_7$) δ 174.80, 153.70, 152.92, 152.22, 139.03, 135.11, 133.95, 128.07, 126.92, 122.99, 119.16, 36.46, 30.66. HRMS (ESI) calculated for $C_{15}H_{13}N_2O_6S^-$ ([M-Na]$^-$) 349.0500, found 349.0496.

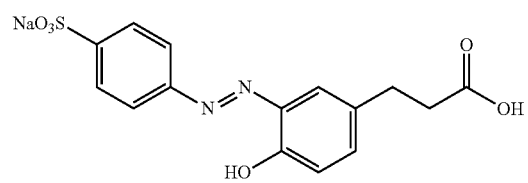

Synthesis of Azo 2.

Figure 11:
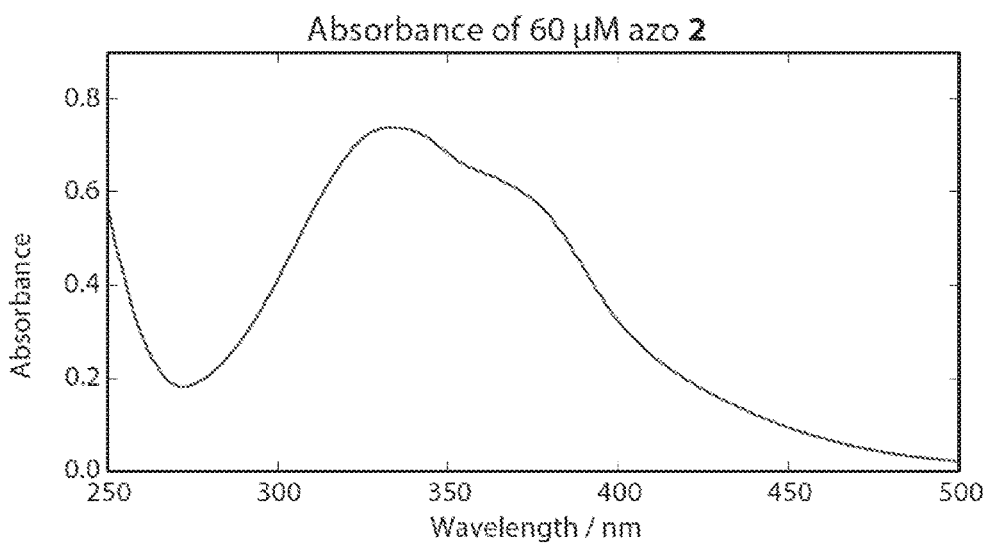
FIG. 11 shows the absorbance spectrum of azo 2.

To 29 mL of 1 M aqueous HCl was added 3-(4-aminophenyl)propionic acid (1 g, 6.06 mmol, 1 eq.), and the solution was stirred until all solids had dissolved. This solution was cooled to 0° C., and 0.42 g (6.06 mmol, 1 eq.) of sodium nitrite in 5 mL of water was added dropwise. After 30 min, this solution was added dropwise to sodium 4-hydroxybezenesulfonate dihydrate (1.41 g, 6.06 mmol, 1 eq.) and sodium carbonate (6.03 g, 57.4 mmol) in 14.4 mL of water at 0° C. After the addition was complete, the reaction was allowed to warm to room temperature and was stirred for an additional hour. During this time the reaction mixture turned dark red/black. The solvent was removed under reduced pressure, and the crude reaction mixture was dissolved in methanol and filtered through Celite. This procedure was repeated a second time, at which point the product mixture was adsorbed to 20 mL of silica gel and purified via silica gel chromatography with a gradient of 0-70% methanol in dichloromethane to give 1 g (44%) of material. A portion of this was purified by reverse-phase chromatography with a gradient of 5-95% acetonitrile in water with 0.1% TFA over 1 h. An absorbance spectrum is shown in FIG. 11. This portion was used for binding studies and characterization. $^1$H NMR (400 MHz, DMF-$d_7$) δ 8.25 (d, J=2.2 Hz, 1H), 7.98 (d, J=8.35 Hz, 2H), 7.84 (dd, J=8.6, 2.2 Hz, 1H), 7.52 (d, J=8.35 Hz, 2H), 7.10 (d, J=8.5 Hz, 1H), 3.02 (t, J=7.5 Hz, 2H), 2.72 (t, J=7.5 Hz, 2H). $^{13}$C NMR (100 MHz, DMF-$d_7$) δ 174.56, 156.23, 151.10, 146.47, 140.57, 138.16, 131.91, 130.44, 123.79, 123.14, 118.69, 35.93, 31.55. MALDI-TOF MS calculated for $C_{15}H_{13}N_2O_6S^-$ ([M-Na]$^-$) 349.05, found 349.21.

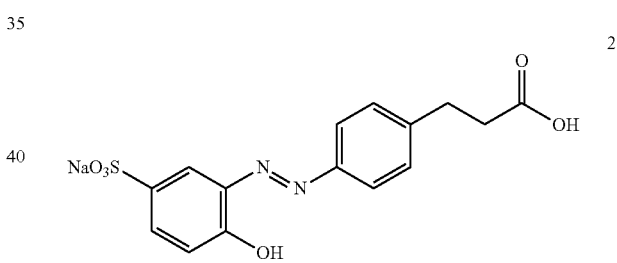

Synthesis of Azo 1 Maleimide (3).

Azo 1 (70 mg, 0.2 mmol, 1 eq.) and N-hydroxysuccinimide (46.0 mg, 0.4 mmol, 2 eq.) were dissolved in 1 mL of DMF. N,N'-Diisopropylcarbodiimide (50.4 mg, 0.4 mmol, 2 eq.) was added and the reaction was stirred for 72 h. To this solution, 2-maleimido-ethylamine (28.0 mg, 0.2 mmol, 1 eq.) was added, and the reaction was stirred for 5 h. The solvent was removed under reduced pressure, and the solid taken up in 5 mL of methanol and adsorbed to 1 mL of silica gel. The product was purified using silica gel chromatography with a gradient of 5 to 20% methanol in dichloromethane with 0.1% acetic acid to afford 17 mg of material (18%). $^1$H NMR (600 MHz, DMF-$d_7$) δ 11.63 (s, 1H), 8.07 (t, J=6.2 Hz, 1H), 8.02-7.91 (m, 4H), 7.71 (d, J=2.2 Hz, 1H), 7.33 (dd, J=8.5, 2.3 Hz, 1H), 7.02 (m, 3H), 3.56 (d, J=5.9 Hz, 2H), 3.35 (q, J=6.0 Hz, 2H), 2.90 (t, J=7.8 Hz, 2H), 2.45 (t, J=7.8 Hz, 2H). $^{13}$C NMR (150 MHz, DMF-$d_7$) δ 172.96, 172.22, 153.69, 152.45, 152.36, 139.08, 135.58, 135.06, 134.31, 128.09, 126.62, 123.00, 119.14, 38.55, 38.48, 38.31, 31.36. HRMS (ESI) calculated for $C_{21}H_{19}N_4O_7S^-$ ([M-Na]$^-$) 471.0980, found 471.0970.

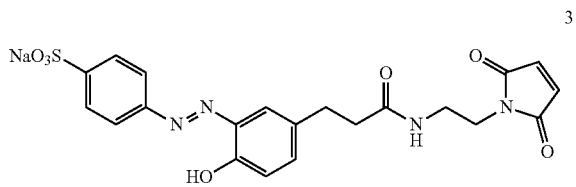

3

Synthesis of Azo 2 NHS-Ester (4).

Flash column chromatography-purified azo 2 (180 mg, 0.484 mmol, 1 eq.) and N-hydroxysuccinimide (66.8 mg, 0.581 mmol, 1.2 eq.) were dissolved in 0.5 mL of DMF. N,N-diisopropylcarbodiimide (73.3 µL 0.581 mmol, 1.2 eq.) was added and the reaction was stirred for 15 h. The solvent was removed under reduced pressure, and the product was taken up in methanol and adsorbed to 1 mL of silica gel. The product was purified via silica gel chromatography with a gradient of 0 to 50% methanol in dichloromethane with 0.1% acetic acid to afford 60 mg of material (26%). $^1$H NMR (400 MHz, DMF-d$_7$) δ 11.74 (s, 1H), 8.25 (d, J=1.7 Hz, 1H), 7.99 (d, J=8.3 Hz, 2H), 7.83 (dd, J=8.6, 2.1 Hz, 1H), 7.60 (d, J=8.3 Hz, 2H), 7.07 (d, J=8.5 Hz, 1H), 3.52 (s, 2H), 3.15 (s, 4H), 2.94 (s, 4H). $^{13}$C NMR (100 MHz, DMF-d$_7$) δ 170.46, 168.81, 155.14, 150.64, 143.98, 140.96, 137.40, 131.47, 129.90, 123.06, 122.75, 117.69, 31.88, 30.30, 25.87. HRMS (ESI) calculated for $C_{19}H_{16}N_3O_8S^-$ ([M-Na]$^-$) 446.0664, found 446.0658.

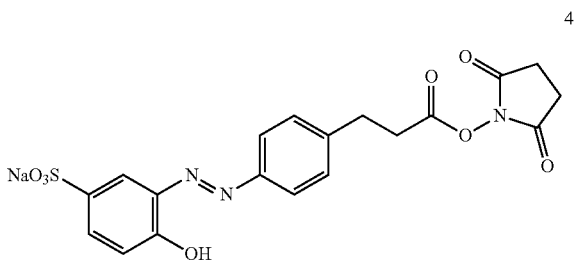

4

Synthesis of Azo 2 Boc-Amine (S3).

Compound 4 (60 mg, 0.128 mmol, 1 eq.), N-Boc-ethylenediamine (20.5 mg, 0.128 mmol, 1 eq.), and triethylamine (15.5 mg, 0.154 mmol, 1.2 eq.) were added to 1 mL of DMF and stirred at room temperature for 30 min. The solvent was removed, and the product was purified via silica gel chromatography with a gradient of 0 to 50% methanol in dicholormethane with 0.1% acetic acid. Trace amounts of N-Boc-ethylenediamine remained, so the product mixture was added to 3 mL of Amberlite IR-120 Na form resin in 5 mL of water and turned end-over-end on a laboratory rotisserie for 30 min. After removal of the resin, the solvent was removed under reduced pressure to afford 58 mg of material (86%). $^1$H NMR (400 MHz, MeOH-d$_4$) δ 8.26 (d, J=2.3 Hz, 1H), 7.82 (d, J=2.3 Hz, 1H), 7.78 (d, J=8.5 Hz, 2H), 7.38 (d, J=8.3 Hz, 2H), 7.09 (d, J=8.7 Hz, 1H), 3.20 (t, J=6.1 Hz, 2H), 3.08 (t, J=5.6 Hz, 2H), 2.97 (t, J=7.4 Hz, 2H), 2.73 (s, 2H), 2.55 (t, J=7.5 Hz, 2H), 1.36 (s, 9H). $^{13}$C NMR (100 MHz, MeOH-d$_4$) δ 178.55, 175.70, 154.23, 145.36, 136.24, 130.34, 129.46, 127.15, 122.44, 118.07, 99.98, 79.72, 39.10, 37.02, 31.26, 27.52, 25.03, 22.13. MALDI-TOF MS calculated for $C_{22}H_{27}N_4O_7S^-$ ([M-Na]$^-$) 491.16, found 491.40.

The Boc group was removed by addition of 0.5 mL of triuoroacetic acid to the compound, followed by removal of the volatile components under reduced pressure.

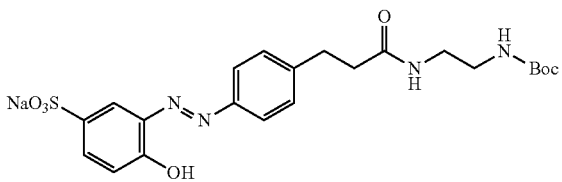

S3

Synthesis of Azo 2 Boc-Alkoxyamine (S4).

To 0.85 mL of dichloromethane was added N-hydroxysuccinimide (19.5 mg, 0.17 mmol, 1.44 eq.) and (Boc-aminooxy)acetic acid (27.1 mg, 0.142 mmol, 1.2 eq.). After sonication to mostly dissolve the N-hydroxysuccinimide, N,N-dicycohexylcarbodiimide (35 mg, 0.17 mmol, 1.44 eq.) was added, and the reaction was stirred at room temperature for 15 min. The reaction mixture was cooled to 0° C., filtered through Celite, and added to S3 (58 mg, 0.118 mmol, 1 eq.) and triethylamine (23.8 mg, 0.236 mmol, 2 eq.) in 0.85 mL of DMF. The reaction was stirred for 30 min, at which point the solvent was removed, and the crude product was adsorbed to 1 mL of silica gel. The product was purified using silica gel chromatography with a gradient of 0 to 50% methanol in dichloromethane with 0.1% acetic acid to afford 41.3 mg of material (60%). $^1$H NMR (400 MHz, MeOH-d$_4$) δ 8.30 (d, J=2.3 Hz, 1H), 7.81 (m, J=5.3, 2.4 Hz, 3H), 7.40 (d, J=8.0 Hz, 2H), 7.08 (d, J=8.6 Hz, 1H), 4.26 (s, 2H), 3.32 (s, 4H), 3.18 (q, J=7.3 Hz, 8H), 3.00 (t, J=7.7 Hz, 2H), 2.57 (t, J=7.7 Hz, 2H), 1.43 (s, 9H), 1.30 (t, J=7.3 Hz, 12H). Excess triethylamine was observed and could not be separated from the compound. $^{13}$C NMR (100 MHz, MeOH-d$_4$) δ 174.40, 170.65, 158.36, 154.36, 149.31, 145.41, 136.70, 136.32, 130.32, 129.36, 127.05, 122.41, 117.91, 82.27, 74.97, 46.54, 38.42, 37.05, 31.23, 27.19, 24.80, 7.97. HRMS (ESI) calculated for $C_{24}H_{30}N_5O_9S^-$ ([M-Triethylammonium]$^-$) 564.1770, found 564.1761.

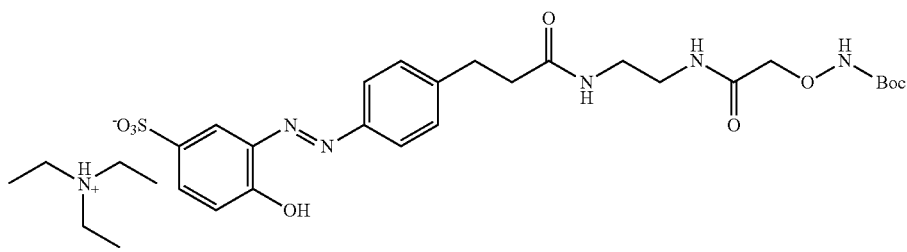

S4

The Boc group was removed by addition of 0.5 mL of triuoroacetic acid to the compound, followed by removal under reduced pressure to afford compound 5.

Synthesis of Azo 2 Maleimide (6).

Flash column chromatography-purified azo 2 (27.3 mg, 0.073 mmol, 1 eq.) and N-hydroxysuccinimide (10.1 mg, 0.088 mmol, 1.2 eq.) were dissolved in 0.5 mL of DMF. N,N-Diisopropylcarbodiimide (13.6 μl, 0.088 mmol, 1.2 eq.) was added and the reaction was stirred for 15 h. To this solution, 2-maleimido-ethylamine (17.6 mg, 0.073 mmol, 1 eq.) was added, and the reaction was stirred for 30 min. The solvent was removed under reduced pressure, and the solid was taken up in 5 mL of methanol and adsorbed to 1 mL of silica gel. The product was purified using silica gel chromatography with a gradient of 0 to 50% methanol in dichloromethane with 0.1% acetic acid to afford 2.5 mg of material (7%). $^1$H NMR (600 MHz, DMF-$d_7$) δ 8.25 (d, J=2.2 Hz, 1H), 8.08 (t, J=5.8 Hz, 2H), 7.96 (d, J=8.3 Hz, 2H), 7.81 (dd, J=8.5, 2.2 Hz, 1H), 7.45 (d, J=8.4 Hz, 2H), 7.05 (d, J=8.5 Hz, 1H), 7.02 (s, 2H), 3.58 (t, J=5.8 Hz, 2H), 3.36 (q, J=5.9 Hz, 2H), 2.97 (t, J=7.8 Hz, 2H), 2.48 (t, J=7.9 Hz, 2H). $^{13}$C NMR (150 MHz, DMF-$d_7$) δ 172.79, 172.25, 155.49, 151.06, 146.85, 142.49, 138.06, 135.61, 132.19, 130.42, 124.14, 123.75, 118.28, 38.50, 38.35, 38.05, 32.18. MALDI-TOF MS calculated for $C_{21}H_{19}N_4O_7S^-$ ([M-Na]$^-$) 471.10, found 471.37.

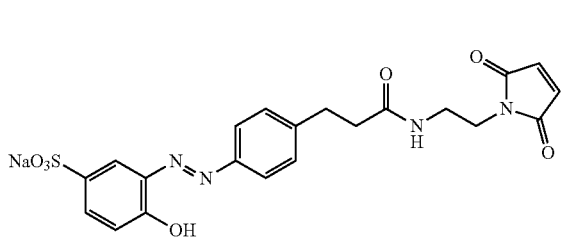

6

Results and Discussion.

The affinity component of this technique was based on a host-guest interaction formed between β-cyclodextrin and the handle. A well characterized cyclic polymer of glucose, β-cyclodextrin has moderate water solubility, is inexpensive, and forms host guest complexes with stability constants ranging from 1 to $10^7$ M$^{-1}$. In previous work, β-cyclodextrin has been found not to bind the native functional groups of most proteins with any appreciable affinity. This characteristic makes it well-suited for bioconjugate chromatography because any binding interactions would depend predominantly on the introduced functional group and potentially its environment.

To determine useful parameters for designing this system, we constructed a computational model using non-linear plate theory as first described by Martin and Synge. The adsorption isotherm used in this model accounts for the effect of binding constant and valency on elution time. Its most notable shortcoming is that it does not account for cooperitivity between binding sites or consider the effects of the local protein environment on binding. However, these features can be incorporated empirically by varying the binding constants.

Figure 2A:
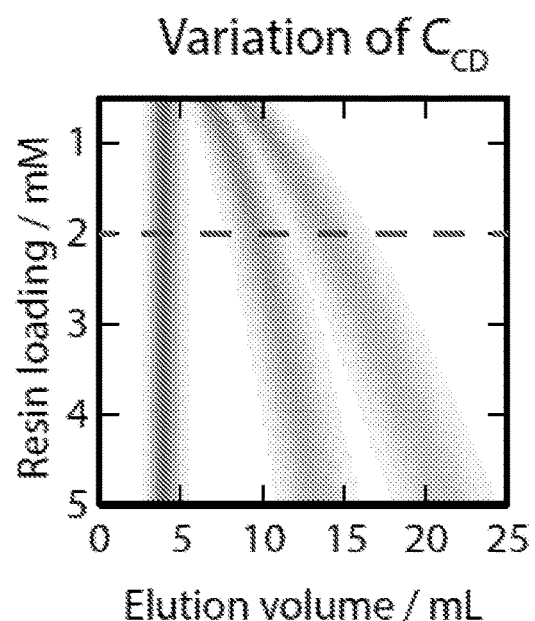
FIG. 2A shows heatmaps depicting simulated elution profiles as a function of resin loading. The left profile, the center profile, and the right profile represent unmodified, singly modified, and doubly modified proteins, respectively. The column volume was 4 mL with 50 theoretical plates, and a linear gradient of 0-10 mM β-cyclodextrin was applied from 0 to 25 mL. The dashed line represents the resin loading value for Resin B, as described herein.

We used this model to determine useful parameters for separating proteins modified with zero, one, and two handles. Based on the frequency distribution of binding constants between β-cyclodextrin and its ligands, we assumed that we could find a handle with an association constant ($K_a$) of about $10^{3.5}$ M$^{-1}$. Using this binding constant as a starting point, we performed a series of simulations in which the loading of β-cyclodextrin on the column (CCD) was varied from 1 to 5 mM. The mobile phase consisted of a linear gradient of 0 to 10 mM free β-cyclodextrin as a competitive binder. The resulting elution profiles were plotted as a two-dimensional heatmap (FIG. 2A). These results indicated that a resin loading of at least 1 mM β-cyclodextrin effects separation between proteins with zero, one, and two affinity handles.

Figure 2B:
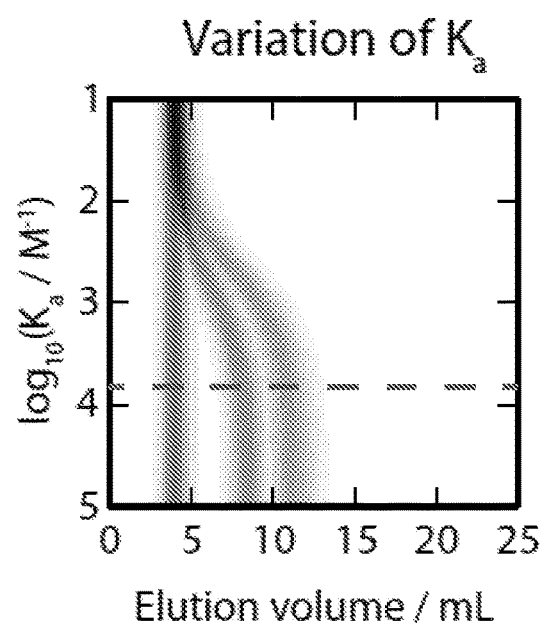
FIG. 2B shows heatmaps depicting simulated elution profiles as a function of binding constant. The left profile, the center profile, and the right profile represent unmodified, singly modified, and doubly modified proteins, respectively. The column volume was 4 mL with 50 theoretical plates, and a linear gradient of 0-10 mM β-cyclodextrin was applied from 0 to 25 mL. The dashed line represents the binding constant value for Resin B, as described herein.

Having determined 1 mM of β-cyclodextrin as a lower target for CCD, we performed the same analysis, but instead varying Ka (FIG. 2B). These results indicated the separation of proteins with differing levels of modification is possible above a $K_a$ of $10^{3.25}$M$^{-1}$, after which point stronger binding does not appear to result in better separation.

In addition to using this model to design this chromatography system, we also used it to determine optimal elution gradients for mixtures of modified proteins. The model was implemented as an IPython notebook in Python and a second implementation in JavaScript is available from the inventors.

The primary design consideration for the handle was the potential for modification using oxidative coupling. In its most common form, oxidative coupling occurs between anilines and o-aminophenols in less than two minutes. This chemistry is particularly well-suited to the construction of well-defined bioconjugates because it usually reaches quantitative conversion and has been used successfully for demanding couplings. Moreover, when ferricyanide is used as an oxidant, this reaction displays excellent functional group tolerance and can be used with a variety of protein substrates.

Figure 3:
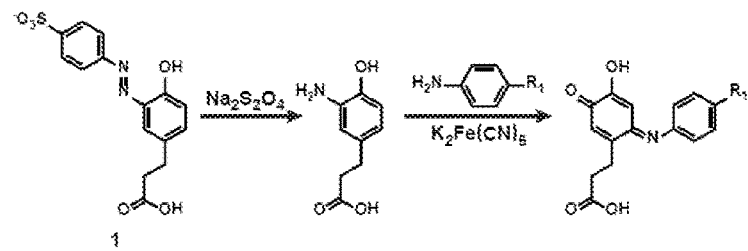
FIG. 3 shows azo handles for cyclodextrin binding. Both 1 and 2 bind to β-cyclodextrin with binding constants that are sufficient for purification purposes. Their cleavage under mild reducing conditions affords anilines as oxidative coupling partners. These groups can be coupled to many desired moieties through highly efficient chemistry.
Figure 3:
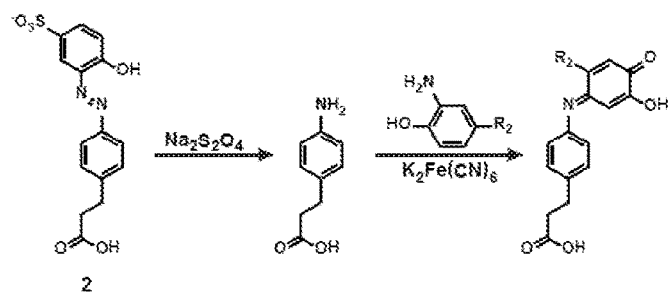

In addition to its oxidative coupling functionality, the handle needed to bind to β-cyclodextrin with a $K_a$ of $10^3$-$10^4$ M$^{-1}$ and to be water-soluble and compatible with protein modification. We identified azo compounds as a promising class of handles. Not only is the binding of azo dyes to β-cyclodextrin well characterized, but azo dyes with o-hydroxy groups can be cleaved under mild reducing conditions to afford anilines and o-aminophenols. Azo compounds 1 and 2 were identified as potential affinity handles (FIG. 3) and were synthesized in one step each from commercially available materials. Their measured binding constants of $10^{3.35}$ M$^{-1}$ and $10^{3.47}$ M$^{-1}$, respectively, and their water solubility at concentrations above 1 mM suggested that both would work readily as affinity handles.

Given the relative ease of synthesis of azo 1, we synthesized it first and used it as a tool compound to aid with the design of an appropriate resin. Later it became apparent that placing the o-aminophenol coupling partner on the protein could lead to a small amount of cross reactivity between the oxidized o-aminophenol and neighboring residues. As a result, azo 2 was used for all subsequent experiments.

Example 2. Design and Synthesis of Cyclodextrin Resin for Affinity Chromatography 6-O-p-Toluenesulfonyl-β-cyclodextrin (S1) was prepared on a 50 g scale as described by Byun et al. (*Org. Syn.* 2000, 77, 225).

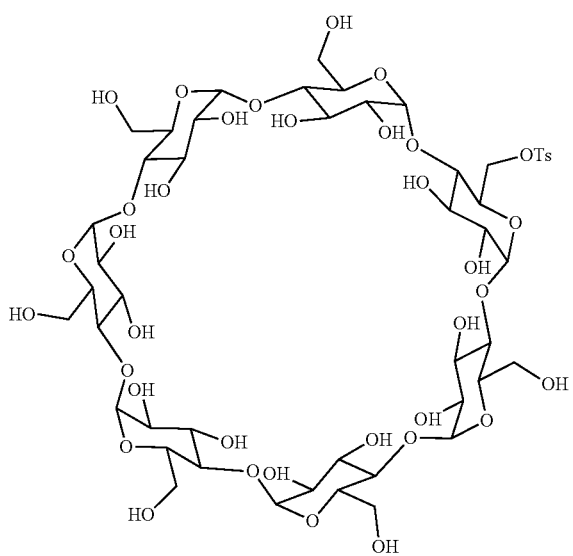

S1

Synthesis of 6-azido-β-cyclodextrin (S2).

This procedure was adapted from Nielsen et al. (*Biomacromolecules*, 2010, 11, 1710-1715). Cyclodextrin S1 (7.2 g, 5.6 mmol, 1 eq.) was dissolved in 49 mL of DMF in a 250 mL round bottom flask. To this solution was added sodium azide (6.3 g, 97 mmol, 17.3 eq.). The reaction was stirred at 75° C. under $N_2$ for 18 h. The reaction was cooled to room temperature, filtered through celite, and poured into 800 mL of vigorously stirred acetone. The white precipitate was collected with a Büchner funnel. To remove excess sodium azide, the crude product was dissolved in 60-70 mL of water at 80° C., cooled on ice to room temperature, and again poured into 800 mL of vigorously stirred acetone to precipitate the product. After filtration, this procedure was repeated an additional three times, at which point it was determined that the amount of sodium azide in the product was less than 0.3% by mass. (Christova-Bagdassarian, et al. *Univ. Chem. Technol. Metall.* 2007, 42, 311-314) A total of 6.4 g of material was recovered (>90%).

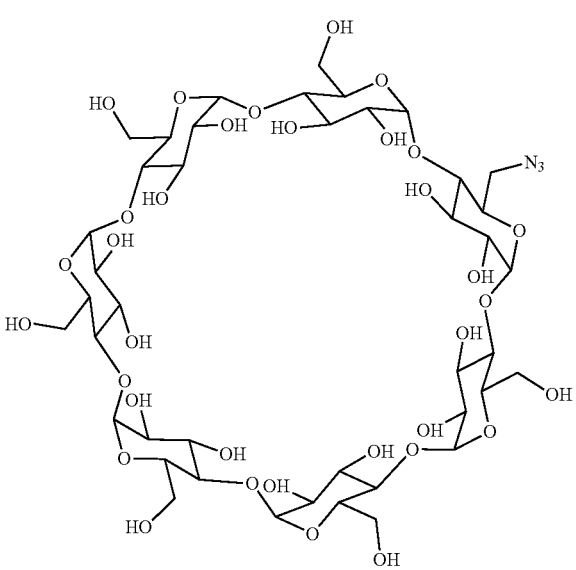

S2

Carboxy Sepharose CL-4B (S7).

Settled sepharose CL-4B (8 mL) was rinsed successively with 10 mL each of with water, 3:1 water:dioxane, 1:3 water dioxane, and dioxane. Depending on the desired level of modification, 100-700 mg of 1,1'-carbonyldiimidazole in 4 mL of dioxane was added to this resin. This suspension was rotated end-over-end on a laboratory rotisserie for 15 min, at which point it was rinsed with 10 mL each of dioxane, 1:3 water dioxane, 3:1 water:dioxane, and water. Once the resin had fully drained, 1.3 g of aminocaproic acid was added in 10 mL of water adjusted to pH 10 with 1 M NaOH, and the resin was turned end-over-end on a laboratory rotisserie for 15 h. The resin was washed repeatedly with 0.1 M pH 4 sodium acetate buffer containing 0.5 M sodium chloride and 0.1 M pH 8 TRIS buffer containing 0.5 M sodium chloride, in alternation. The resin was finally washed with several portions of water.

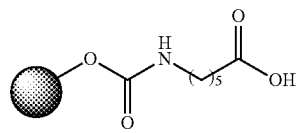

S7

Alkyne-Terminated Resin (S8).

After the carboxylic acid content of the resin S7 was determined, it was rinsed thoroughly with water and allowed to drain completely. To this resin was added propargyl amine (0.46 g, 5 mmol) in 5 mL of water and N-(3-dimethylaminopropyl)-N-ethylcarbodiimide hydrochloride (0.766 g, 4 mmol) in 5 mL of water, both pH adjusted to 4.5 using HCl. After mixing, the pH of the reaction mixture was checked and adjusted again to pH 4.5, if necessary. The reaction rotated end-over-end on a laboratory rotisserie for 1 h, at which point the pH was again adjusted to 4.5 using NaOH. After 18 h, the resin was washed repeatedly with 0.1 M sodium acetate buffer containing 0.5 M sodium chloride buffer, pH 4, and 0.1 M TRIS buffer containing 0.5 M sodium chloride, pH 8, in alternation. The resin was finally washed with several portions of water.

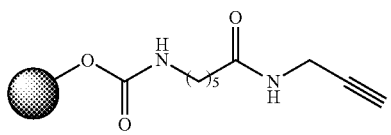

S8

β-Cyclodextrin-Terminated Resin (S9).

This procedure has been adapted from Punna et al. (*Bioconjugate Chem.* 2005, 16, 1536-1541) Resin S8 was rinsed successively with 10 mL each of water, 3:1 water:DMF, 1:3 water:DMF, and DMF. To the drained resin was added 2,6-lutidine (64.3 mg, 0.6 mmol) in 0.5 mL DMF, 2,2'-bipyridine (93.7 mg, 0.6 mmol) in 1 mL DMF, 6-azido-β-cyclodextrin (348 mg, 0.3 mmol) in 1.5 mL of DMF, copper(I) bromide (43 mg, 0.3 mmol) in 1 mL of DMF, and sodium ascorbate (119 mg, 0.6 mmol) in 1 mL of water. This reaction mixture was turned end-over-end on a laboratory rotisserie for 15 h. The resin was rinsed with 10 mL each of DMF, 1:3 water:DMF, 3:1 water:DMF, and water, followed by repeated washings with 0.1 M pH 4 sodium acetate buffer containing 0.5 M sodium chloride and 0.1 M pH 8 TRIS buffer containing 0.5 M sodium chloride, in alternation. The resin was finally washed with several portions of water.

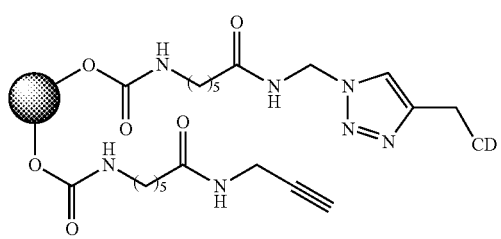

S9

Determination of in-Solution Binding Constants.

Figure 12:
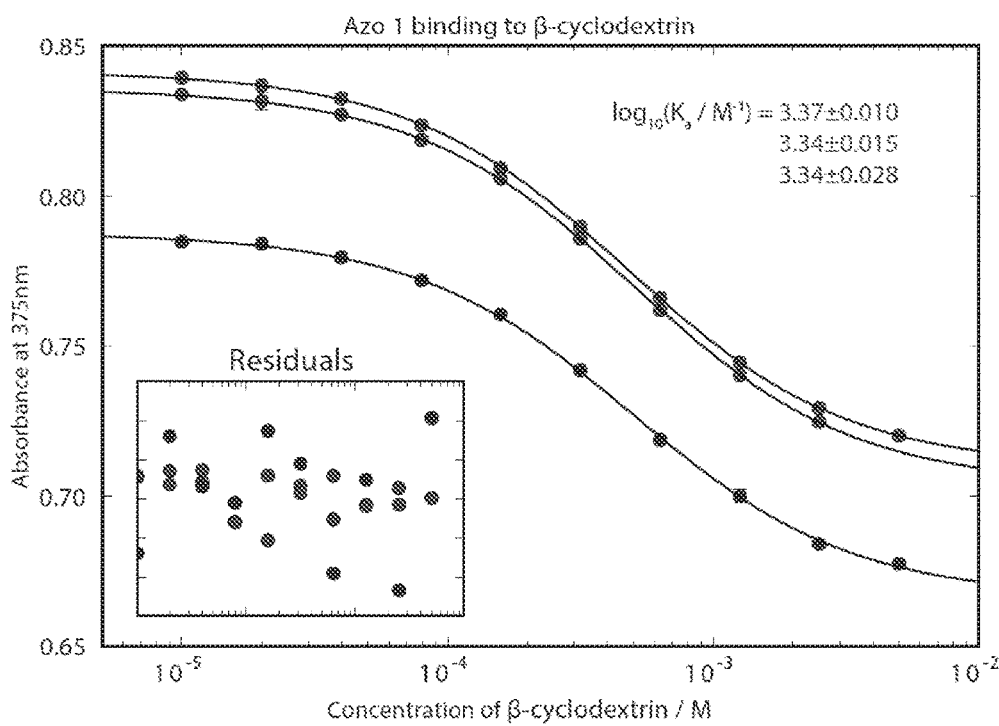
FIG. 12 shows the binding of azo 1 to β-cyclodextrin.
Figure 13:
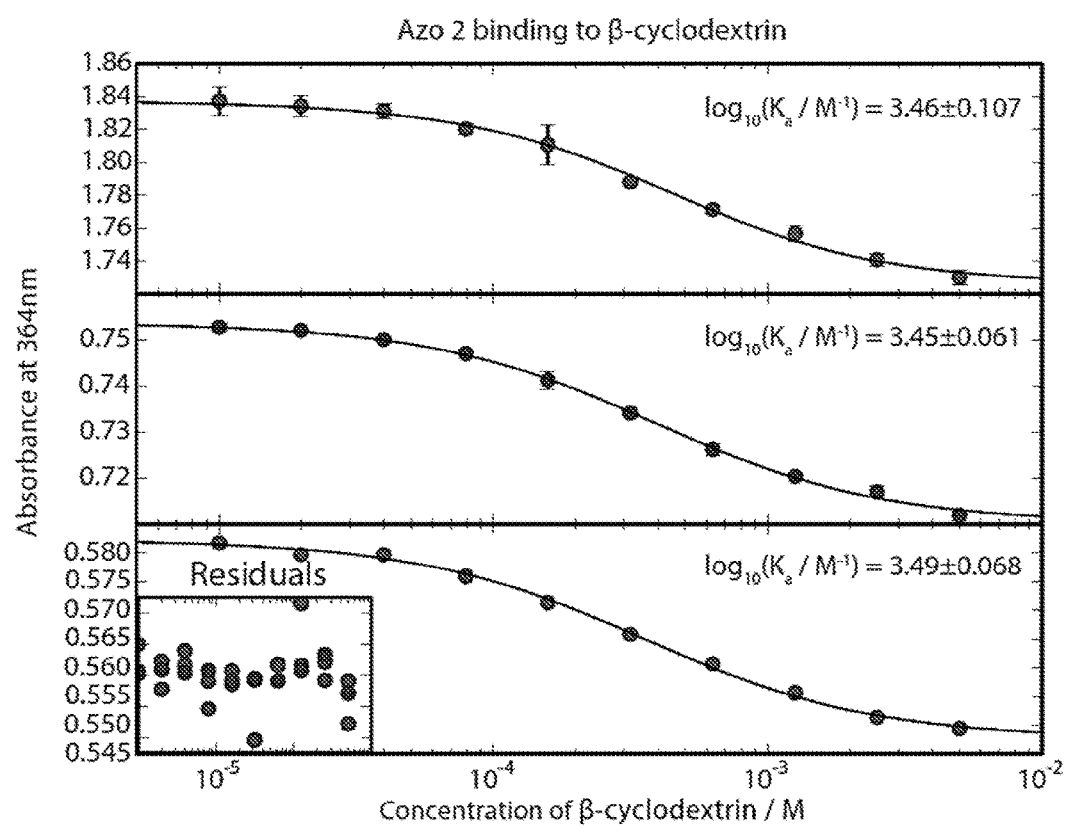
FIG. 13 shows the binding of azo 2 to β-cyclodextrin.

A solution of 100 μM azo 1 or 2 was prepared in 10 mM pH 6.5 phosphate buffer (henceforth called azo buffer). A 10 mM solution of β-cyclodextrin was then prepared by dissolving β-cyclodextrin in the previously prepared azo buffer (henceforth called CD buffer). The CD buffer was then titrated into 0.75 mL of the azo buffer, and the absorbance of the solution was measured three times after each addition. After the titration, the absorbance values at 375 nm were plotted, and a single-site binding model was fit to the data using the nonlinear curve fitting package in SciPy.

$$A_{375} = \varepsilon_{azo} \frac{F_{azo} - F_{CD} - K_d + \sqrt{(F_{azo} + F_{CD} + K_d)^2 + 4F_{azo}K_d}}{2} + \varepsilon_{CD\text{-}azo} \frac{F_{azo} + F_{CD} + K_d - \sqrt{(F_{azo} + F_{CD} + K_d)^2 - 4F_{azo}F_{CD}}}{2} \quad (1)$$

where $F_{CD}$ is the total concentration of β-cyclodextrin in units of M, $F_{azo}$ is the total concentration of azo in units of M, $K_d$ is the dissociation constant in units of M, $\varepsilon_{azo}$ is the 1 cm molar extinction coefficient for the uncomplexed azo dye in units of $M^{-1}$, and $\varepsilon_{CD\text{-}azo}$ is the 1 cm molar extinction coefficient for the complexed azo dye, also in units of $M^{-1}$. This procedure was performed three times each for azo 1 and for azo 2 and the results are shown in FIG. 12 and FIG. 13.

Determination of Carboxylic Acid Concentration on Resins.

Resin S8 or S9 (0.5 mL, settled) was measured into a 3 mL fritted column and washed thoroughly with 1 mM HCl until the pH of the eluate was 3 as determined by pH paper. This resin was then washed three times each with 1 mL of 1 mM HCl with 100 μM phenolphthalein. After it had completely drained, the resin was transferred to a 4 mL scintillation vial with an additional 0.5 mL of 1 mM HCl with 100 μM phenolphthalein, such that the vial contained 0.5 mL of resin in a total volume of 1 mL. A solution of 100 mM NaOH was then added until the resin suspension displayed the first hint of a persistent pink color. This process was repeated for a control sample of unmodified sepharose CL-4B, and the amount of excess 100 mM NaOH required to neutralize the modified resin was used to calculate its concentration of carboxylic acid.

Determination of Resin Loading and Binding Constant.

Figure 14:
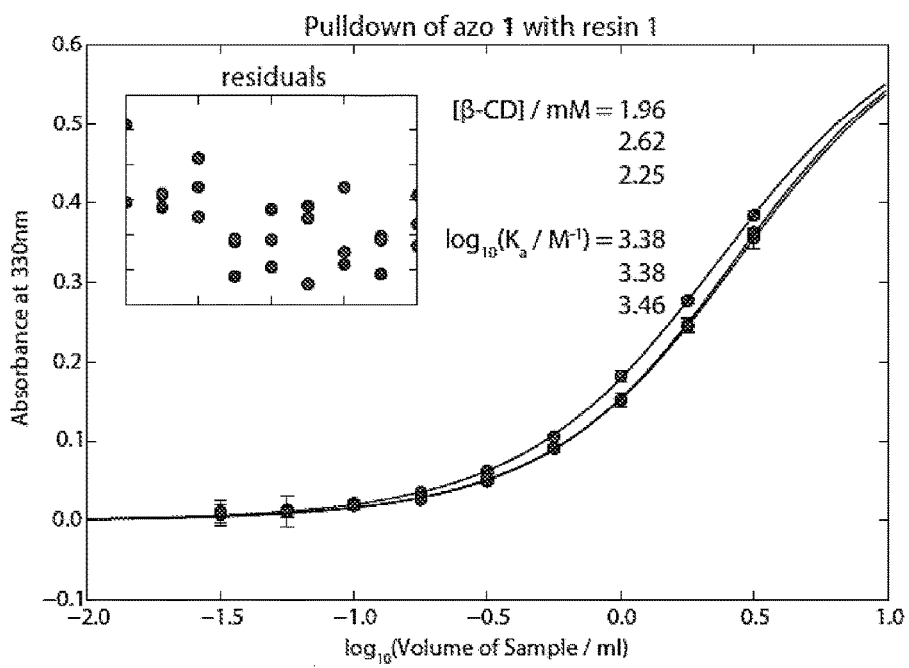
FIG. 14 shows the results of pulldown experiments with azo 1 and resins 1-3.
Figure 14:
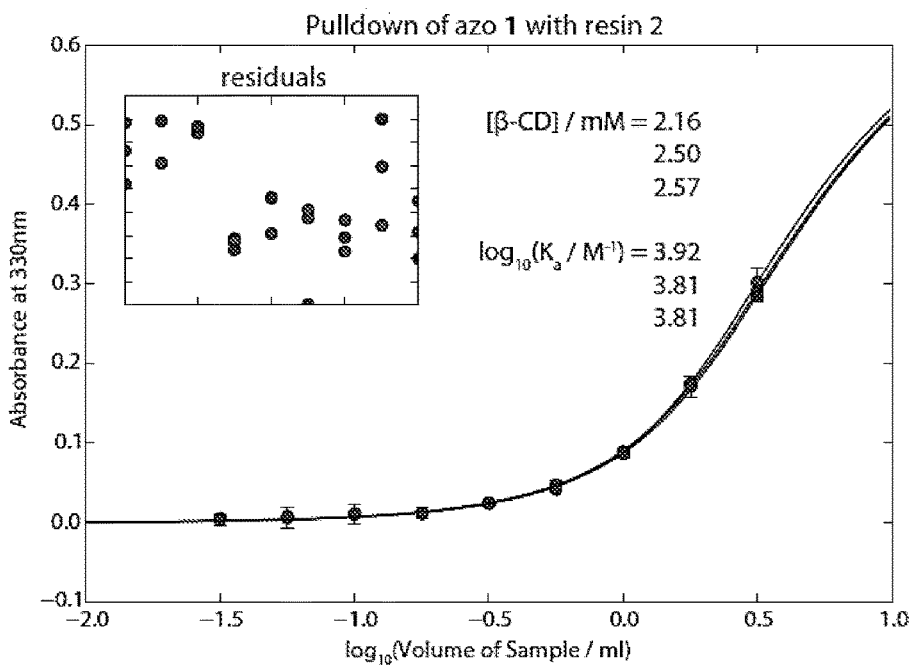

Resin S9 (0.5 mL, settled) was measured into a 3 mL fritted column. This resin was washed thoroughly with 10 mM pH 6.5 phosphate buffer and transferred into a 20 mL scintillation vial with an additional 0.5 mL of buffer, such that the vial contained 0.5 mL of resin in 1 mL total volume. A solution of 550 M azo 1 in 10 mM pH 6.5 phosphate buffer was then titrated into this resin, and the absorbance of the supernatant was measured three times after every addition. A 1:1 binding model was then fit to the data, and the binding constant and resin loading were determined. Because binding constant and resin loading are correlated variables during the fitting, this titration was performed three times for every resin, and the reported value is the average of the three trials. Results are shown in FIG. 14.

Figure 4:
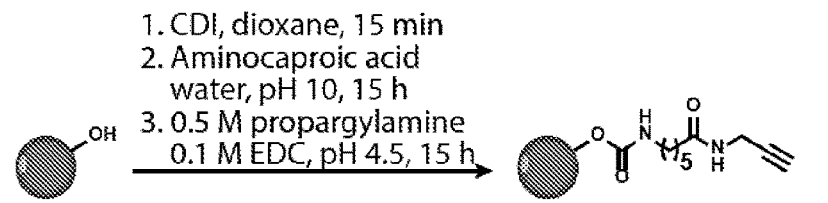
FIG. 4 shows the functionalization of 90 μM sepharose CL-4B with β-cyclodextrin. Sepharose CL-4B was first functionalized with CDI and reacted with aminocaproic acid to afford a resin functionalized with 5 to 30 mM of carboxylic acid. This acid was then coupled to propargyl amine. Onto this resin was added β-cyclodextrin using CuAAC to give the final material. Because the concentration of attached β-cyclodextrin never exceeded 2 mM, all resins contain an excess of alkyne-terminated linker on their surfaces.
Figure 4:
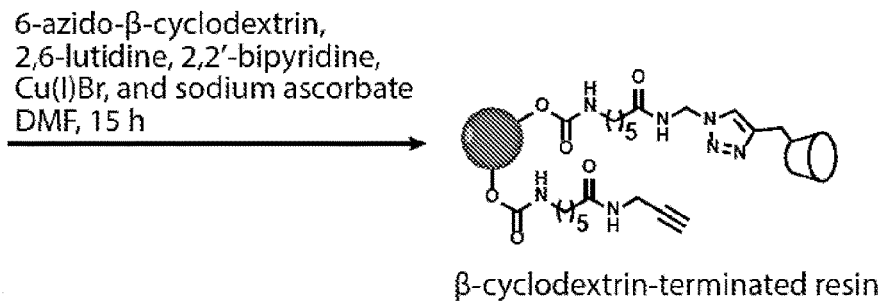

The resin component of this system was designed to display at least 1 mM of β-cyclodextrin and to interact minimally with unmodified proteins. Early work indicated that the ion-exchange character of ECH sepharose 4B and NHS-sepharose 4B, which contain secondary amines and isourea groups, respectively, impeded the elution of negatively charged proteins. Moreover, uncharged epoxy-activated sepharose 4B did not couple sufficient β-cyclodextrin to effect separation. As a result, we turned to sepharose CL-4B, which contains no ionizable groups and can be efficiently activated with 1,1'-carbonyldiimidazole (FIG. 4). Activated sepharose CL-4B was coupled with aminocaproic acid to yield a water-stable resin with between 5 and 30 mM of carboxylic acid functionality. To this resin was coupled propargylamine using EDC. Azido β-cyclodextrin was then installed using the copper(I)-catalyzed akyne-azide cycloaddition to afford the final separation support.

TABLE 1

Resins with varying $C_{linker}$

| | $C_{linker}$/mM | $C_{CD}$/mM | $\log_{10}(K_a/M^{-1})$ |
|---|---|---|---|
| A | 9 | 2.3 ± 1 | 3.4 ± 0.1 |
| B | 17 | 2.4 ± 0.5 | 3.9 ± 0.2 |
| C | 32 | 1.8 ± 0.9 | 3.9 ± 0.3 |

We explored the importance of linker concentration ($C_{linker}$) by synthesizing a series of resins with varying $C_{linker}$ (Table 1). For each resin, $C_{CD}$ and the $K_a$ to azo 1 were measured by performing pulldowns of azo 1. All resins had β-cyclodextrin loadings of 2 mM within error, and it is presumed that sterics limited further modification. It was noted that the $K_a$ increased with increasing $C_{linker}$. These results suggested that azo 1 may favorably interact with some part of the linker between the β-cyclodextrin and the resin to increase the overall binding constant.

Figure 5A:
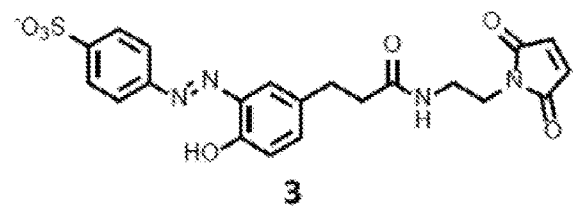
FIG. 5A shows the structure of azo-maleimide reagent 3.
Figure 5B:
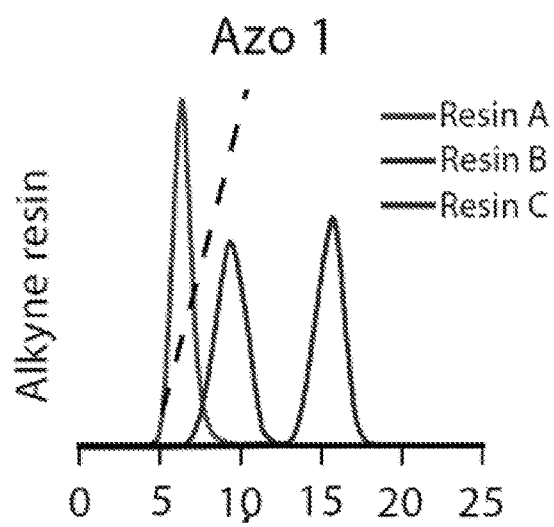
FIG. 5B shows that azo 1 elutes more slowly from alkyne-terminated resins with higher degrees of alkyne substitution. The dashed line represents a gradient of 0 mM to 10 mM β-cyclodextrin that was applied during the separation.
Figure 5C:
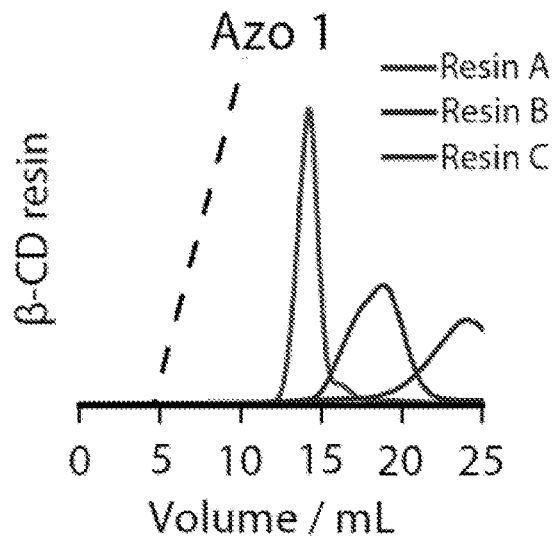
FIG. 5C shows that the attachment of β-cyclodextrin to the resin increases the binding further. The dashed line represents a gradient of 0 mM to 10 mM β-cyclodextrin that was applied during the separation.

To verify this hypothesis, the elution of azo 1 from these resins was characterized before and after their modification with β-cyclodextrin (FIG. 5B and FIG. 5C). Azo 1 eluted more slowly from resins with higher $C_{linker}$, suggesting that this handle did indeed have some affinity for the linker itself (FIG. 5B). Modification with β-cyclodextrin created an additional favorable interaction and increased retention times (FIG. 5C).

To characterize the interaction of these resins with modified protein, the thermostable homotrimer Mth1491 originally identified in *Methanobacterium* thermoautotrophicum was obtained via expression in *E. coli*. To introduce sites for chemical modification, cysteine residues were added to position 92 on each monomer. Optimization studies showed that this site could be modified selectively over the two endogenous cysteines in positions 70 and 72. For use in initial chromatographic separations, Mth1491 was modified to about 30% with azo maleimide 3.

Figure 5D:
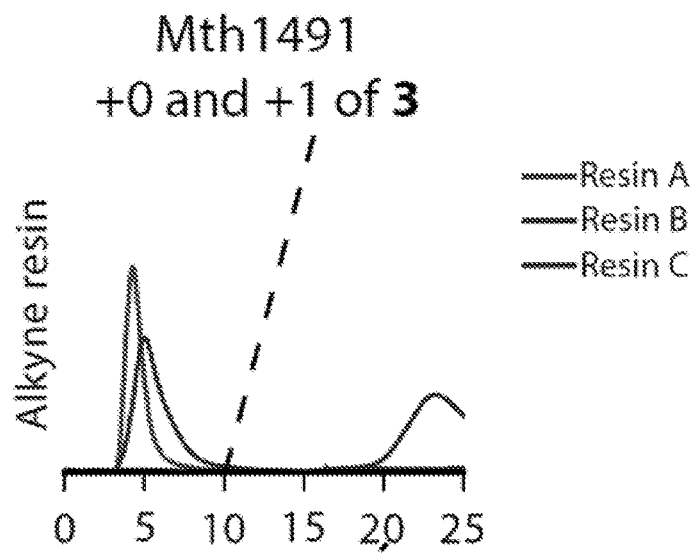
FIG. 5D shows that Mth1491 interacts nonspecifically with resins that have high alkyne substitution levels. The dashed line represents a gradient of 0 mM to 10 mM β-cyclodextrin that was applied during the separation.
Figure 5E:
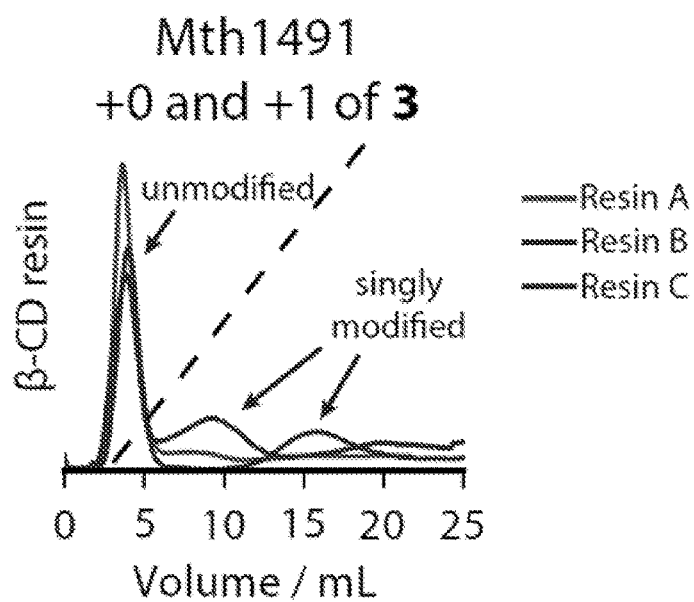
FIG. 5E shows that the attachment of β-cyclodextrin masks these nonspecific interactions and provides separation between unmodified and singly modified proteins. The dashed line represents a gradient of 0 mM to 10 mM β-cyclodextrin that was applied during the separation.

Elution of this protein mixture from the alkyne-terminated resins revealed affinity interactions between the linker and both the azo 1 handle and the protein (FIG. 5D). While resin B slightly separated unmodified and singly modified protein, the higher linker concentration of resin C resulted in the retention of all protein species. However, modification with β-cyclodextrin masked this indiscriminate binding to unmodified protein (FIG. 5E). β-cyclodextrin-terminated resins B and C showed negligible affinity for unmodified protein, yet they both bound the azo 1 handle and separated unmodified and singly modified protein. The strength of this binding interaction appeared to be a function of Clinker, such that the degree of separation between unmodified and singly modified protein could be tuned.

It was determined that the $C_{linker}$ of resin B was useful for separating proteins without excessive retention times. In the experiments described below, a resin with a $C_{linker}$ of 15 mM is discussed.

Example 3. Purification of Proteins Modified with Azo Affinity Handles

General Procedure for Protein Transamination.

To a solution of protein in 10 mM pH 6.5 phosphate buffer was added an equal volume of a 200 μM solution of pyridoxal-5'-phosphate (PLP). This solution was incubated at 37° C. for 1 h. Excess PLP was removed by repeated centrifugal filtration with a 10 kDa molecular weight cutoff (MWCO) membrane and 50 mM pH 5.5 phosphate buffer.

General Procedure for Oxime Formation.

Transaminated protein in 50 mM pH 5.5 phosphate buffer was added to an equal volume of 44 mM deprotected S4 in 50 mM pH 5.5 phosphate buffer. After mixing, the reaction was rotated end-over-end on a laboratory rotisserie at room temperature for 3 d. Excess alkoxyamine was removed by repeated centrifugal filtration against a 10 kDa MWCO membrane.

General Procedure for NHS-Ester Coupling.

To a solution of protein in 25 mM pH 8 phosphate buffer was added 0.5-8 equivalents of 4 in DMSO. After mixing, the reaction stood at room temperature for 1-3 h, at which point excess reagent was removed by repeated centrifugal filtration against a 10 kDa MWCO membrane.

Column Affinity Chromatography.

Resin was packed into a 25 cm by 0.5 cm inner diameter HPLC column. Resin was first suspended in 20% ethanol in water, and this slurry was poured into a column with a packing adaptor fitted to the top. This suspension was then packed by owing 20% ethanol through the column at 0.4 mL/min until the resin had settled. This procedure was repeated until the column was full of packed resin, and then two additional column volumes were owed through the column to ensure that it was packed.

All chromatography was performed using 20 mM pH 6.5 phosphate buffer and 30 mM pH 6.5 phosphate buffer with 10 mM β-cyclodextrin as the eluent. Columns were washed at 0.3 mL/min, and all chromatography was performed at 0.2 mL/min at 8° C.

Results and Discussion.

Figure 6A:
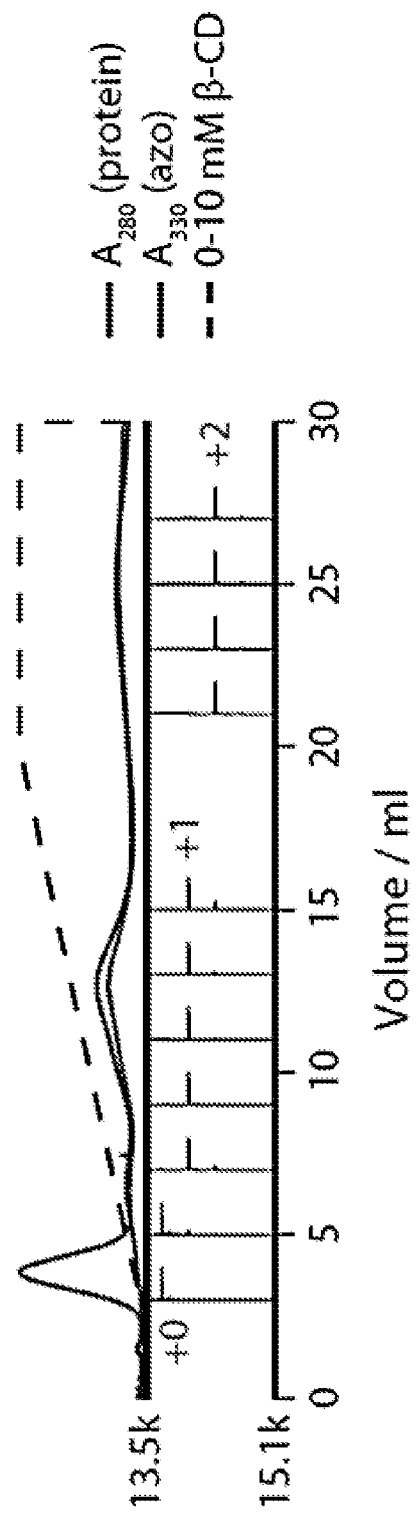
FIG. 6A shows the purification of RNAse A modified with NHS-ester 3 according to the methods of the invention. Reconstructed ESI-TOF mass spectra of selected fractions, rotated 90° clockwise, are shown below the chromatogram.
Figure 6B:
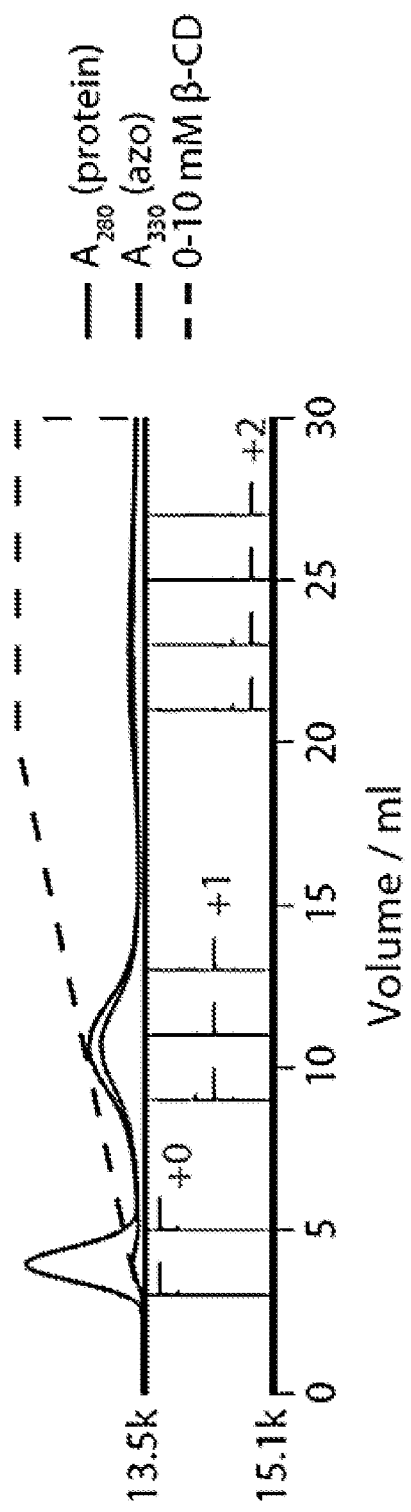
FIG. 6B shows the purification of transaminated RNAse A modified with the alkoxyamine 4 according to the methods of the invention. Reconstructed ESI-TOF mass spectra of selected fractions, rotated 90° clockwise, are shown below the chromatogram.

With the optimal resin in hand, we explored the applicability of this technique by using it to purify several proteins modified with azo 2 handles. We first modified RNAse A, a 13.7 KDa protein with 10 lysines, with azo NHS-ester 4. Purification of the modified proteins resulted in many peaks, with unmodified, singly modified, and doubly modified proteins almost completely resolving (FIG. 6A). At least three overlapping peaks corresponded to singly modified protein; this separation must result from differing chemical environments around the handles on different lysines, such that some are able to interact more favorably with the resin than others. To confirm that the overlapping peaks seen in FIG. 6A are not the result of poor column packing or some other chromatographic anomaly, we also transaminated and N-terminally modified RNAse A with azo alkoxyamine 5 (FIG. 6B). As expected, purification of this protein sample resulted in only one major peak that corresponded to singly modified protein. A minor peak corresponding to doubly modified protein likely corresponded to additional adducts as discussed elsewhere, but the low abundance of this species prevented further characterization. 8 Nonetheless, these results highlight the value of this technique for obtaining pure bioconjugates.

Figure 6C:
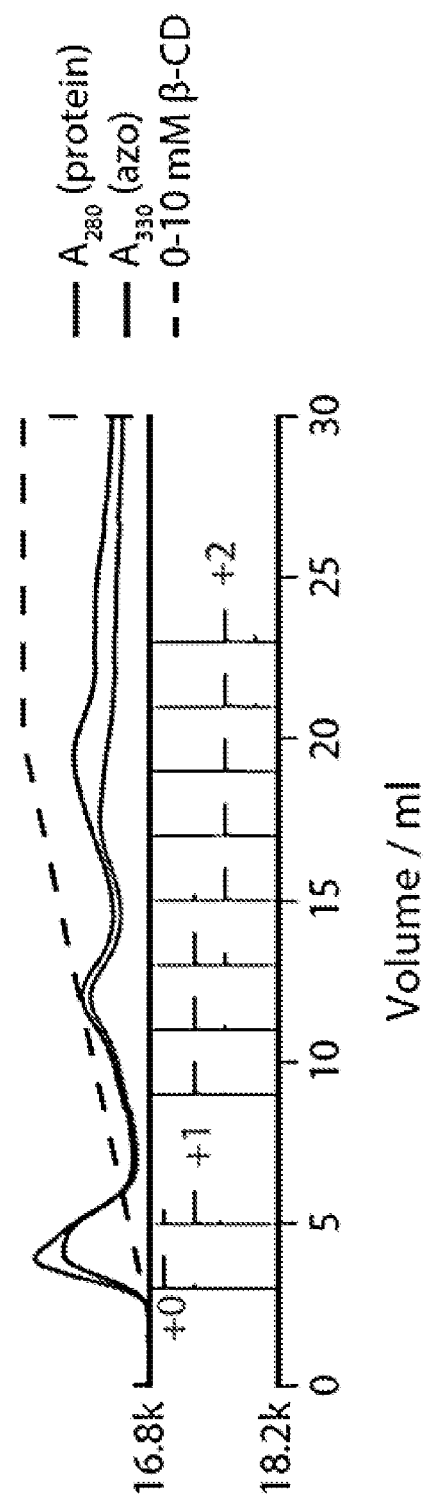
FIG. 6C shows the purification of myoglobin modified with NHS-ester 3 according to the methods of the invention. Reconstructed ESI-TOF mass spectra of selected fractions, rotated 90° clockwise, are shown below the chromatogram.
Figure 6D:
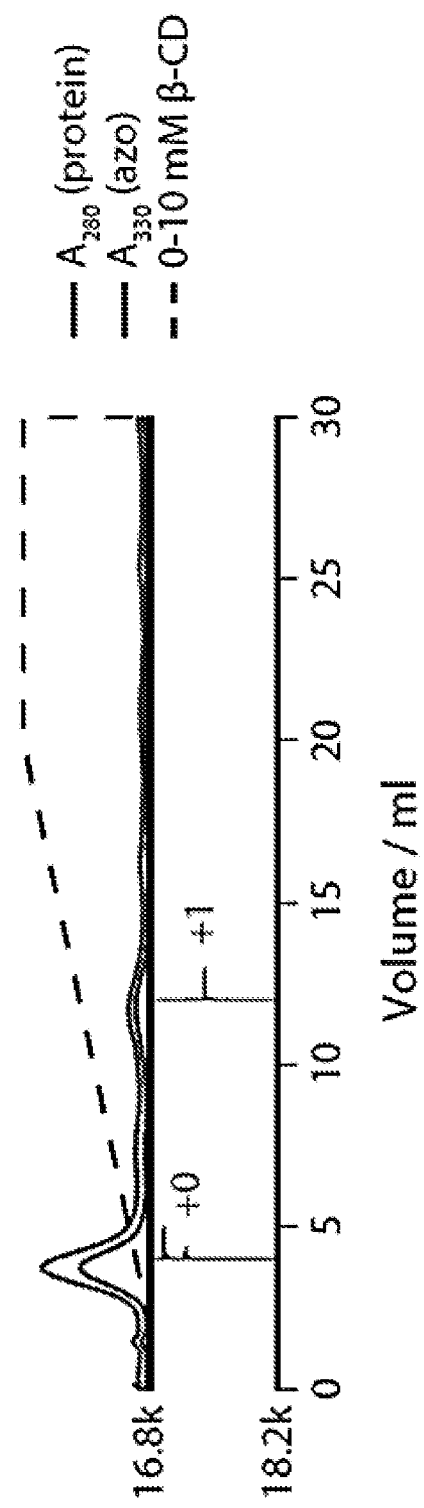
FIG. 6D shows the purification of transaminated myoglobin modified with alkoxyamine 4 according to the methods of the invention. Reconstructed ESI-TOF mass spectra of selected fractions, rotated 90° clockwise, are shown below the chromatogram.

These experiments were repeated with myoglobin to confirm that the trend held (FIG. 6C, FIG. 6D). Again the nonselective modification of lysines with an azo NHS-ester 4 resulted in multiple peaks corresponding to the same modification level. N-terminally modified protein exhibited only two peaks corresponding to zero and one modification.

Figure 6E:
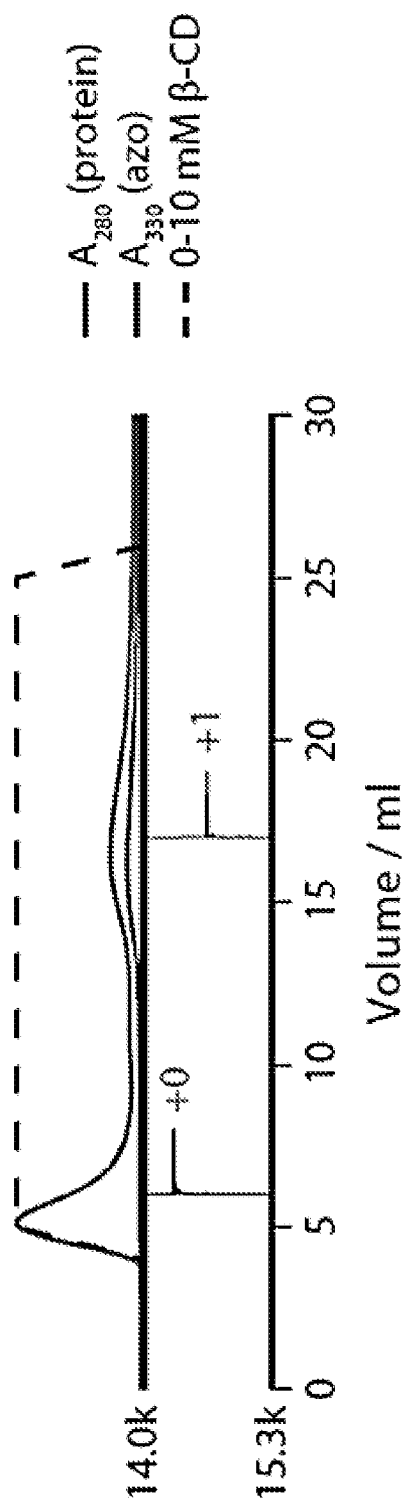
FIG. 6E shows the purification of lysozyme modified with NHS-ester 3 according to the methods of the invention. Reconstructed ESI-TOF mass spectra of selected fractions, rotated 90° clockwise, are shown below the chromatogram.

In contrast to RNAse A and myoglobin, lysozyme has fewer (6) solvent-accessible lysine residues. Purification of lysozyme modified with azo NHS-ester 4 resulted in one distinct peak corresponding to singly modified protein (FIG. 6E). It is presumed that this feature resulted from one particularly reactive lysine, or from multiple lysines having similar chemical environments.

Figure 6F:
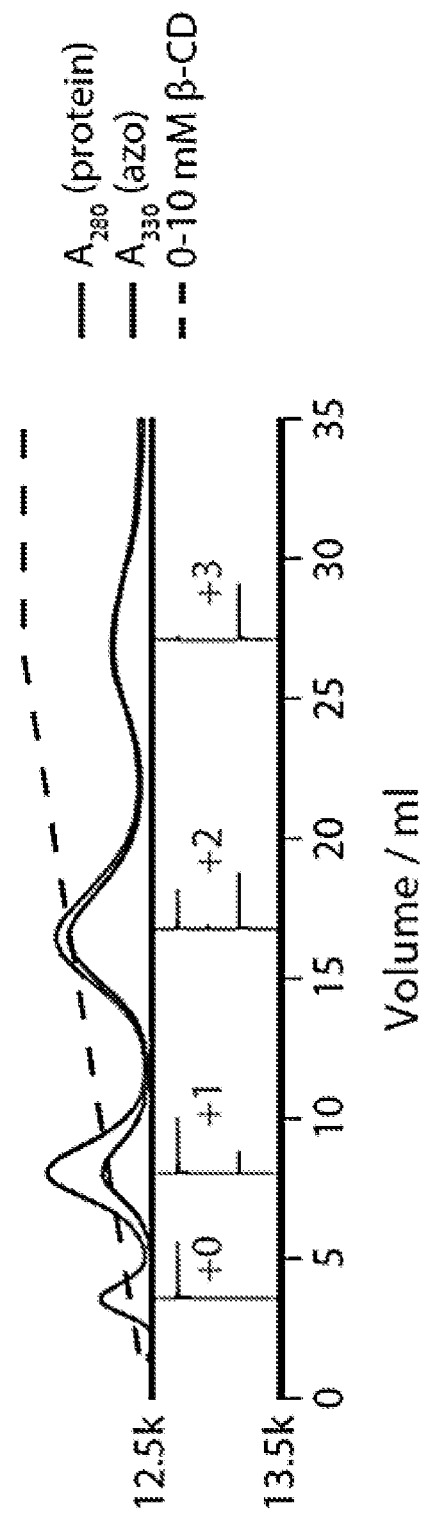
FIG. 6F shows the purification of the Mth1491 trimer modified with maleimide 5 according to the methods of the invention. Reconstructed ESI-TOF mass spectra of selected fractions, rotated 90° clockwise, are shown below the chromatogram.
Figure 6G:
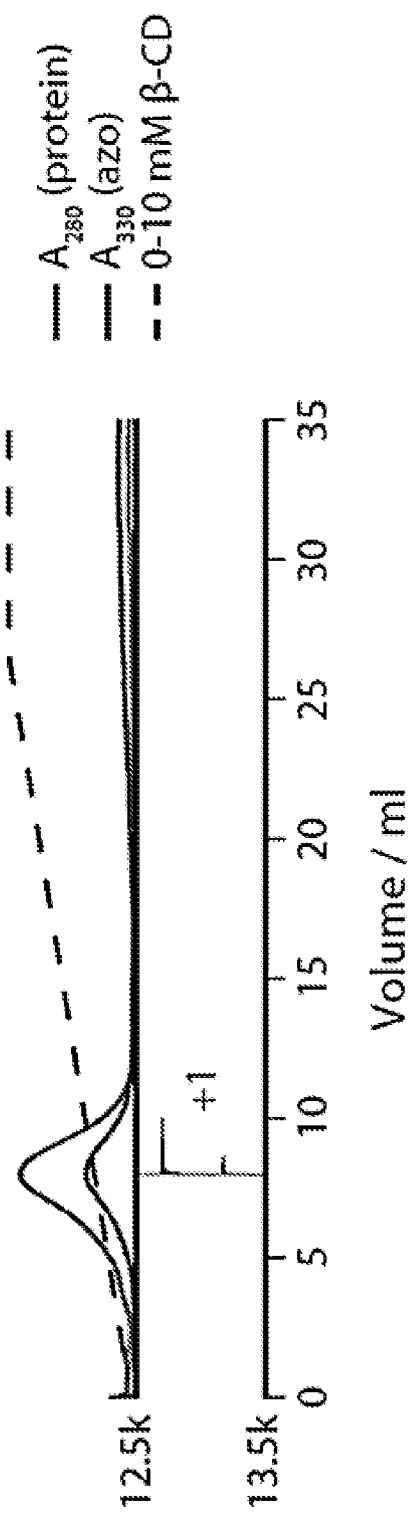
FIG. 6G shows the purification and re-analysis of the isolated singly-modified Mth1491 species according to the methods of the invention. Reconstructed ESI-TOF mass spectra of selected fractions, rotated 90° clockwise, are shown below the chromatogram.
Figure 6H:
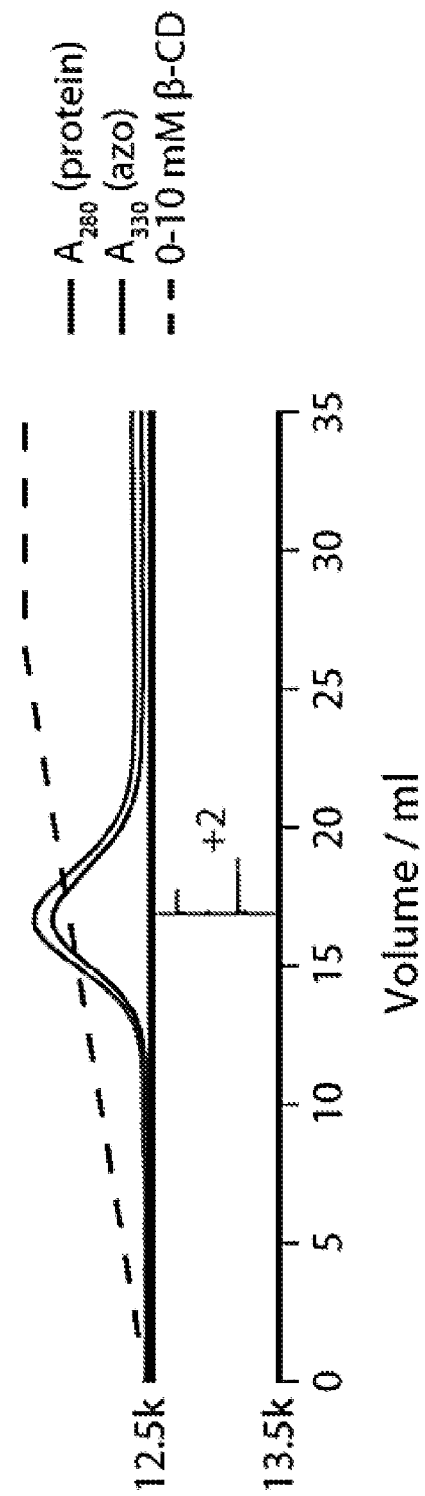
FIG. 6H shows the purification and re-analysis of the isolated doubly-modified Mth1491 species. Reconstructed ESI-TOF mass spectra of selected fractions, rotated 90° clockwise, are shown below the chromatogram.
Figure 6I:
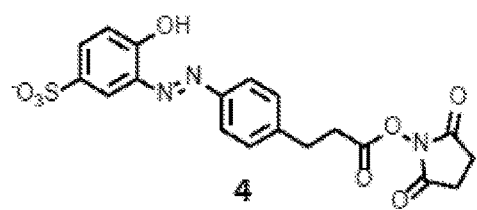
FIG. 6I shows the structures of azo reagents used in the methods of the invention.
Figure 6I:
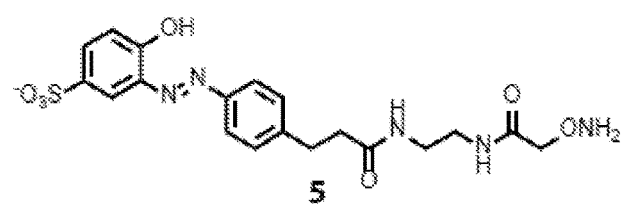
Figure 6I:
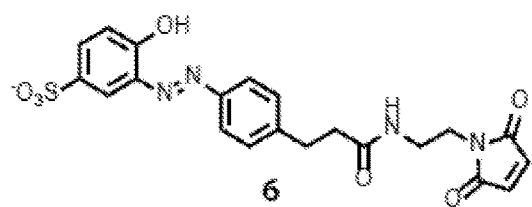

We were particularly interested in applying this methodology to Mth1491 because of its trimeric structure. Unlike monomeric proteins, Mth1491 has three solvent-exposed cysteines in identical chemical environments. After modification, this protein should have only four distinct modification states: unmodified, singly modified, doubly modified, and triply modified. Purification of Mth1491 modified with azo maleimide 6 to about 50% completion resulted in four distinct peaks corresponding to the four modification states (FIG. 6F). Because the trimer disassembled during mass spectrometry analysis, the LCMS traces showed mixtures of unmodified and singly modified monomer that corresponded to the expected ratios within 5%. We also repurified the singly and doubly modified peaks (FIG. 6G, FIG. 6H). The resulting chromatograms confirmed that these peaks corresponded to distinct modification states of the protein, and that the protein stayed folded and assembled during purification, handling, and storage.

Example 4. Construction of a Monodisperse Scaffold for Light Harvesting

Expression and Purification of Mth1491-V92C.

Mth1491-V92C was expressed and purified according to a modified literature procedure (Christendat, et al. *Protein Sci.* 2002, 11, 1409-1414). BL21(GoldλDE3) cells were transformed with a pJexpress404 plasmid containing the ampicillin-resistant gene ampR and the Mth1491-V92C gene with an N-terminal $His_6$-tag followed by a thrombin cleavage site, and the ampicillin resistance gene ampR (DNA2.0 Inc., CA). Colonies were selected for inoculation of lysogeny broth cultures. When cultures reached mid-log phase as determined by O.D. 600, expression was induced by addition of IPTG to a final concentration of 10 μM. Cultures were grown 14-18 h at 37° C., and cells were isolated by centrifugation.

Cells were resuspended in 30 mL of buffer (50 mM $NaH_2PO_4$, pH 8.0; 300 mM NaCl; 10 mM imidazole) containing 10 μg/mL RNase A and 5 μg/mL DNase 1. Cells were lysed by sonication (Branson Ultrasonics) and cleared by centrifugation. The $His_6$-tagged Mth1491-V92C protein was purified from the cleared lysate by affinity chromatography with Ni-NTA agarose.

The purified protein was buffer-exchanged into cleavage buffer (50 mM Tris-HCl, pH 8.0; 10 mM CaCl$_2$) and incubated with thrombin-agarose for 24 h at 4° C. Mth1491-V92C was isolated from the cleaved His6-tag using Amicon Ultra centrifugal filters (10,000 MWCO), to give 20-40 mg of protein per liter of culture. Isolated protein was exchanged into 25 mM phosphate buffer, pH 6.5 and stored at 4° C.

Synthesis of o-nitrotyramine (S5).

This procedure was adapted from Waser and Sommer (*Helv. Chim. Acta* 1923, 6, 54-61). Tyramine (0.57 g, 4.16 mmol, 1 eq.) in 4 mL of water in a 20 mL scintillation vial was cooled to 0° C. with an ice bath. Nitric acid (2 ml) was added dropwise, and the solution turned reddish brown immediately. After the addition, the reaction was warmed to room temperature and stirred for 10 min. The reaction mixture then stood uncovered at room temperature overnight, at which point the yellow precipitate was 10 collected with a Büchner funnel. This crude product was recrystallized from 3-5 mL of boiling water to afford 0.25 g of papery yellow material (34%).

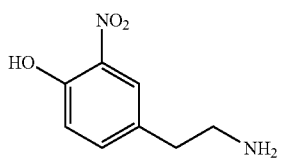

S5

Synthesis of Oregon Green 514 o-Nitrophenol (S6).

Oregon green 514 NHS-ester (2.46 mg, 0.004 mmol, 1 eq.) was dissolved in 1 mL of DMF. Compound S5 (1.31 mg, 0.0097 mmol, 2.4 eq.) and triethylamine (8.15 mg, 0.081 mmol, 20 eq.) were added and the reaction was turned end-over-end for 30 min on a laboratory rotisserie. The solvent was removed under reduced pressure, and the crude product mixture was dissolved in 250° L of methanol. After filtration through a 0.2 μm filter, the o-nitrophenol product was purified via HPLC using an Alltech Econosil C18 10 μm column with a gradient of 5-95% acetonitrile in water with 0.1% TFA over 1 h. The solvent was removed under reduced pressure, and the dye was stored as a 5 mM solution in 50 μL of DMSO.

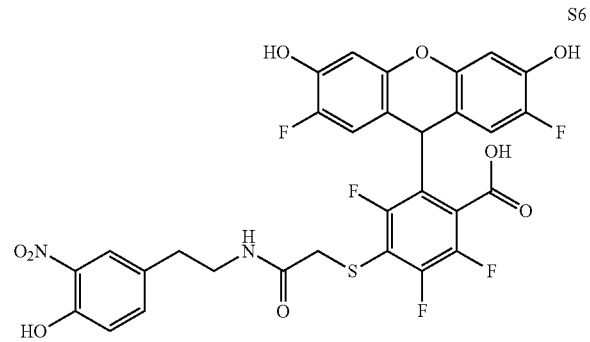 [SMILES: O=C(CSc1c(F)c(F)c(C(=O)O)c(C2c3cc(F)c(O)cc3Oc3cc(O)c(F)cc32)c1F)NCCc1ccc(O)c([N+](=O)[O-])c1]

S6

Synthesis of Oregon Green 514 o-Aminophenol.

To a 0.5 mL solution of 100 mM sodium dithionite in 200 mM pH 6.5 phosphate buffer was added 10-30 μL of 5 mM S6. The reaction was stirred for 10 min, at which point excess dithionite was removed using a C18 Sep-Pak according to the manufacturer's instructions. The eluent was concentrated to dryness, and the product was dissolved in 10 mM pH 6.5 phosphate buffer. The product was used immediately without characterization.

Modification of Mth1491 with Alexauor 350 maleimide.

To 100 μL of 50 M Mth1491 in 25 mM pH 7.2 phosphate buffer was added κ equivalents of AF350 maleimide. The reaction stood at room temperature for 1 h, at which point excess reagent was removed by repeated centrifugal filtration against a 10 kDa MWCO membrane.

Modification of Mth1491 with Azo 2 Maleimide.

To 100 μL of 50 M Mth1491 in 25 mM pH 7.2 phosphate buffer was added 0.3-5 equivalents of 6. After mixing, the reaction stood at room temperature for 1 h, at which point excess reagent was removed by repeated centrifugal filtration against a 10 kDa MWCO membrane.

Cleavage of Purification Handles.

To 100 μL of 50 m Mth1491 in 25 mM pH 7.2 phosphate buffer was added an equal volume of 50 mM sodium dithionite in 25 mM pH 7.2 phosphate buffer. Prior to use, sodium dithionite was stored in a dessicator under vacuum. After 1 min, excess sodium dithionite was removed with a NAP-5 Sephadex size exclusion column. Any remaining sodium dithionite was removed by repeated centrifugal filtration against a 10 kDa MWCO membrane.

Protection of Free Cysteines with Ellman's Reagent.

To a solution of 100 μL of 50 M protein in 10 mM pH 6.5 phosphate buffer was added an equal volume of 10 mM DTNB in 25 mM pH 7.2 phosphate buffer with 1 mM EDTA. The reaction was incubated at room temperature for 3 h, at which point excess reagent was removed and the protein was exchanged into 10 mM pH 6.5 phosphate buffer by repeated centrifugal filtration against a 10 kDa MWCO membrane.

Oxidative Coupling.

A 100 μL portion of a 50 μM Mth1491 monomer in solution was diluted to 250 μL with 10 mM pH 6.5 phosphate buffer. To this solution was added 50 L of 10 mM potassium ferricyanide (100 eq. relative to protein) and 200 μL of 200 μM o-aminophenol OG514 (8 eq. relative to protein). This reaction was allowed to proceed for 15 min, at which point excess reagent was removed by repeated centrifugal filtration against a 10 kDa MWCO membrane.

Deprotection of Free Cysteines.

To 100 μL of 50 μL protein was added 5 μL of 0.5 M tris-(2-carboxyethyl)phosphine (TCEP). After 10 min excess reagent was removed by repeated centrifugal filtration against a 10 kDa MWCO membrane.

Results and Discussion.

Of particular interest to our research group has been the construction and study of artificial systems for light harvesting. These systems are typically composed of dyes that are covalently templated by homomultimeric proteins, such as the tobacco mosaic virus coat protein or the MS2 viral capsid. However, because of the statistical nature of the modification of these proteins, we have been unable to characterize the FRET that occurs for distinct samples of homogeneous protein and have instead studied ensemble averages.

To test this new method for protein modification, we set out to construct a series of scaffolds with precise donor:acceptor ratios of 3:0, 1:2, 2:1, and 0:3. We selected Alexauor 350 (AF350) and Oregon green 514 (OG514) as the FRET pair because of their spectral overlap and the separation between their emission maxima.

Figure 7:
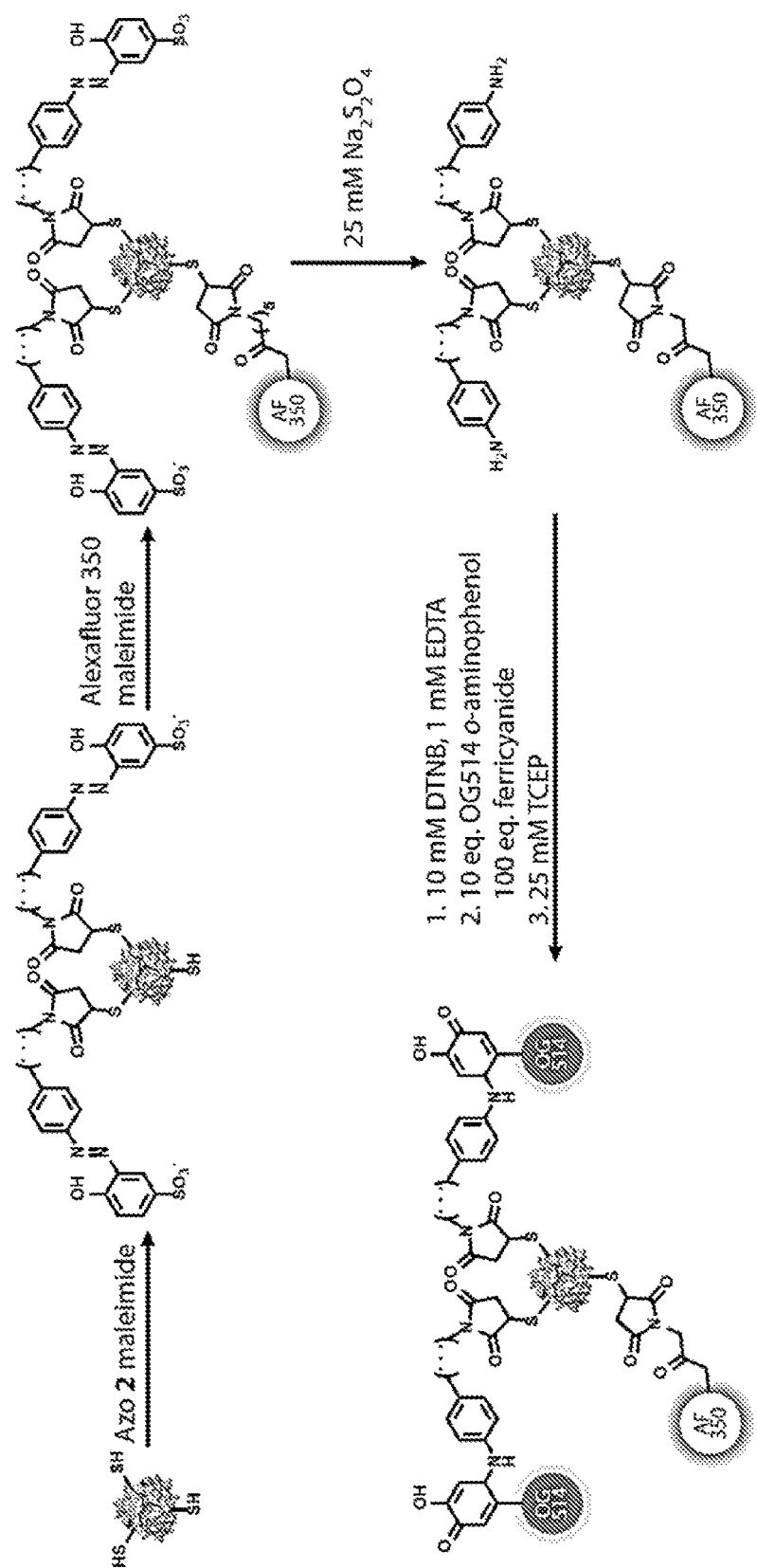
FIG. 7 shows the construction of a two-dye FRET system. Mth1491 is first modified with azo 5, and the singly or doubly modified species is isolated via chromatography. The remaining cysteines are modified with AF350 maleimide. Cleavage of the azo purification handle next affords protein modified with two anilines. The endogenous cysteines (which do not react with maleimides) are protected as disulfides using Ellman's reagent, modified with OG514 o-aminophenol via oxidative coupling, and then deprotected to afford the final two-dye system.
Figure 8:
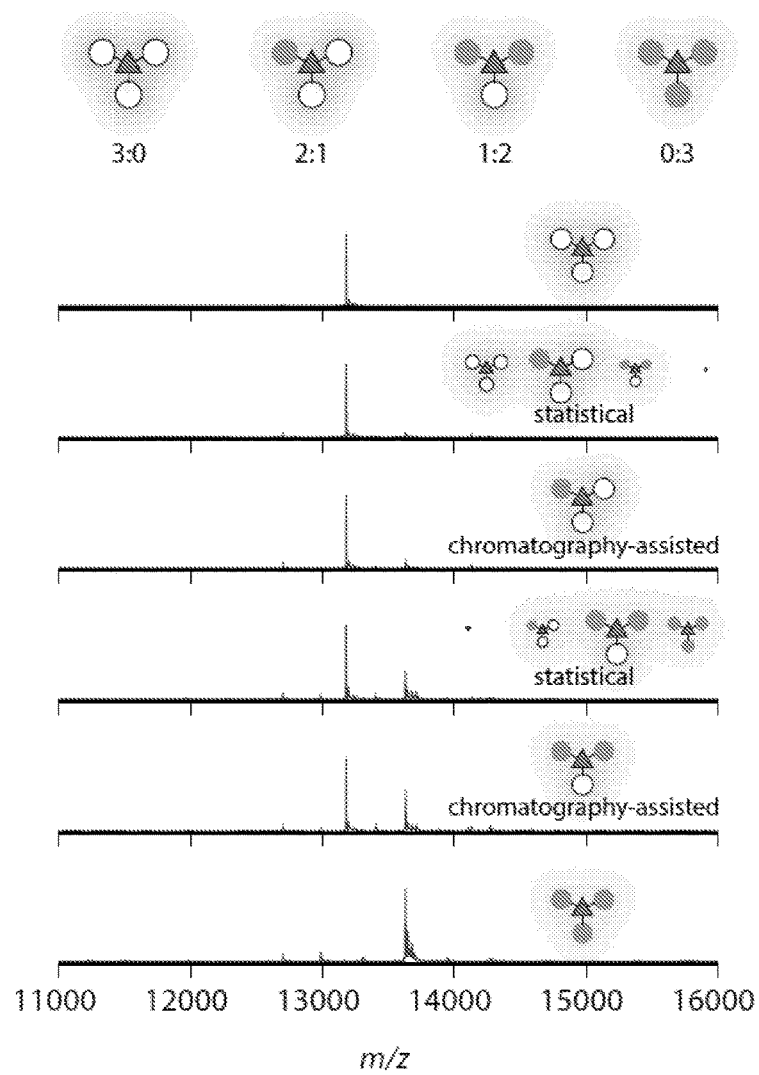
FIG. 8 shows mass spectra of FRET systems after protein disassembly during analysis. The first peak at 13,178 m/z corresponds to the Mth1491 monomer modified with AF350 maleimide, and the second peak at 13,632 m/z corresponds to monomer modified with OG514 o-aminophenol. Under-integration of the OG514 peak was attributed to differing ionizabilities of the two modified monomers. Integrations of the peaks for statistical and purified samples agreed to within 6%. The sizes of the depictions of Mth1491 are proportional to the amount of each species in each sample.

To construct the 1:2 and 2:1 systems, we started with purified Mth1491 ligated to either one or two molecules of azo maleimide 6 (FIG. 7). Onto the remaining solvent-accessible cysteine(s) was installed the AF350 maleimide donor. The azo maleimide 6 handles were cleaved with sodium dithionite to unmask the aniline oxidative coupling partners on the surface of the protein. Early attempts to modify these protein species revealed that oxidized o-aminophenols exhibited minor reactivity with the two endogenous cysteines. As a result, before oxidative coupling the protein was first exposed to Ellman's reagent to protect any solvent-accessible cysteines. The aniline was then coupled to OG514 o-aminophenol using potassium ferricyanide. Protected cysteines were unmasked with tris(2-carboxyethyl)phosphine to afford the templated two-dye systems (FIG. 8, third and fifth traces from top). For comparison purposes, 1:2 and 2:1 AF350:OG514 systems were also constructed statistically without the purification step, such that they had the same dye content as the purified systems to within 5% (FIG. 8, second and fourth traces from top). It was noted that the peak height ratios in the mass spectra of these samples did not correspond to the actual ratio of dyes on the proteins. This feature likely resulted from differing ionizabilities of the dye-protein conjugates, and thus the degree of modification was confirmed by measuring the absorbance spectrum of each sample (FIG. 15).

Figure 9:
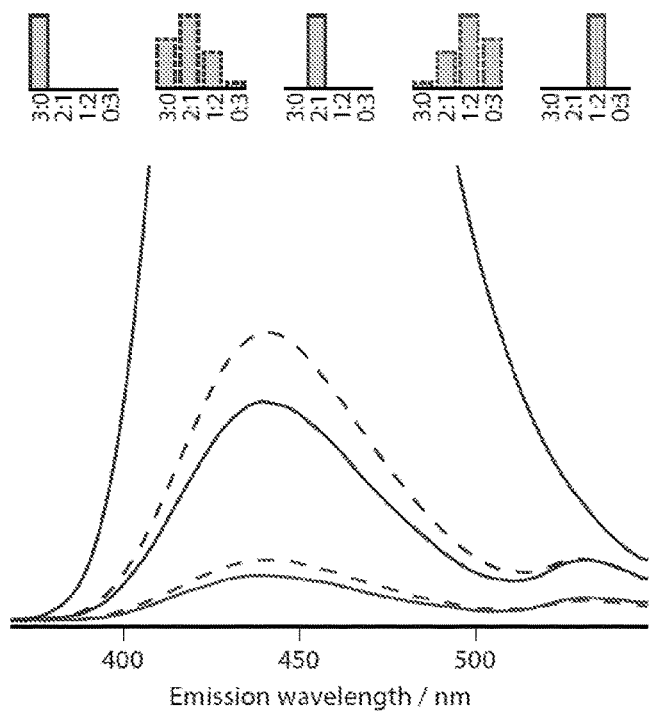
FIG. 9 shows emission spectra of protein-templated dyes. The composition of each sample is indicated by the bar charts above the emission spectra; ratios refer to the ratio of AF350:OG514.

The emission spectra of these samples were characterized upon excitation at 365 nm (FIG. 9). Given the minor overlap between the absorption spectra of AF350 and OG514, the emission spectra were normalized by the absorption of the samples at 365 nm with the contribution from OG514 subtracted. The data showed a clear trend in which the presence of larger amounts of OG514 acceptor led to increased quenching of the AF350 donor. Relative to statistically prepared samples, the purified samples demonstrated increased donor quenching because all donors are on proteins possessing an acceptor partner. We also observed that the relative FRET efficiencies of the purified proteins were larger than those of the statistically prepared proteins because of the increased proximity of the donor and acceptor groups.

Example 5. Recovery and Recycling and Modified Enzymes

Here, we take advantage of the non-covalent interaction between ß-cyclodextrin and strongly hydrophobic molecules to selectively capture and reuse modified enzymes. Specifically, we functionalize sepharose resin with ß-cyclodextrin to enable non-covalent immobilization of enzymes modified with a hydrophobic moiety, such as adamantane or lithocholic acid. After selective capture the enzyme is released from the resin through competitive binding with excess ß-cyclodextrin, adamantane or lithocholic acid. This allows reuse of the enzyme over several cycles. The concept is outlined in FIG. 16 with lithocholic acid as the binding partner to ß-cyclodextrin.

Figure 17A:
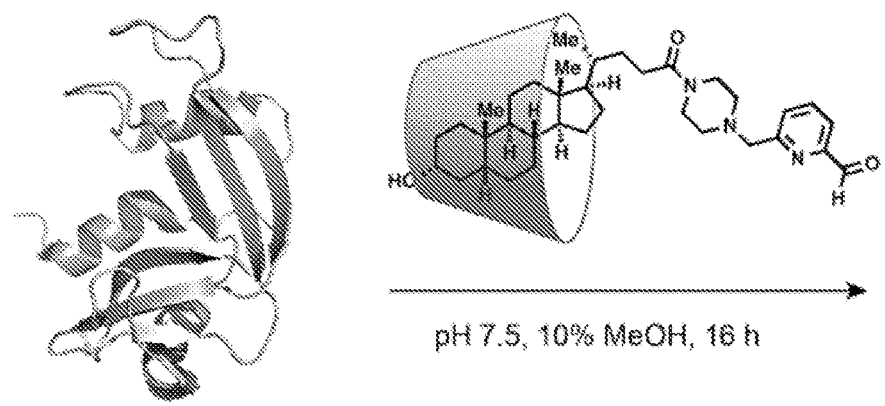
FIG. 17A shows 2-pyridinecarboxaldehyde-mediated N-terminal labeling of wild-type RNase A from bovine pancreas. β-cyclodextrin provides lithocholic acid solubility.
Figure 17A:
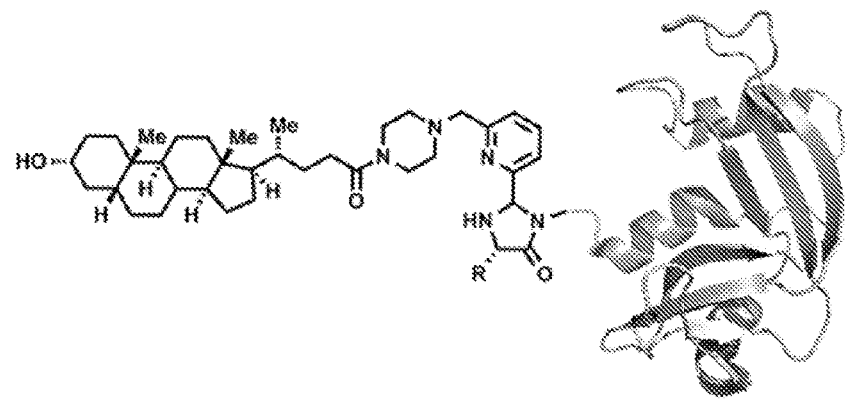
Figure 17B:
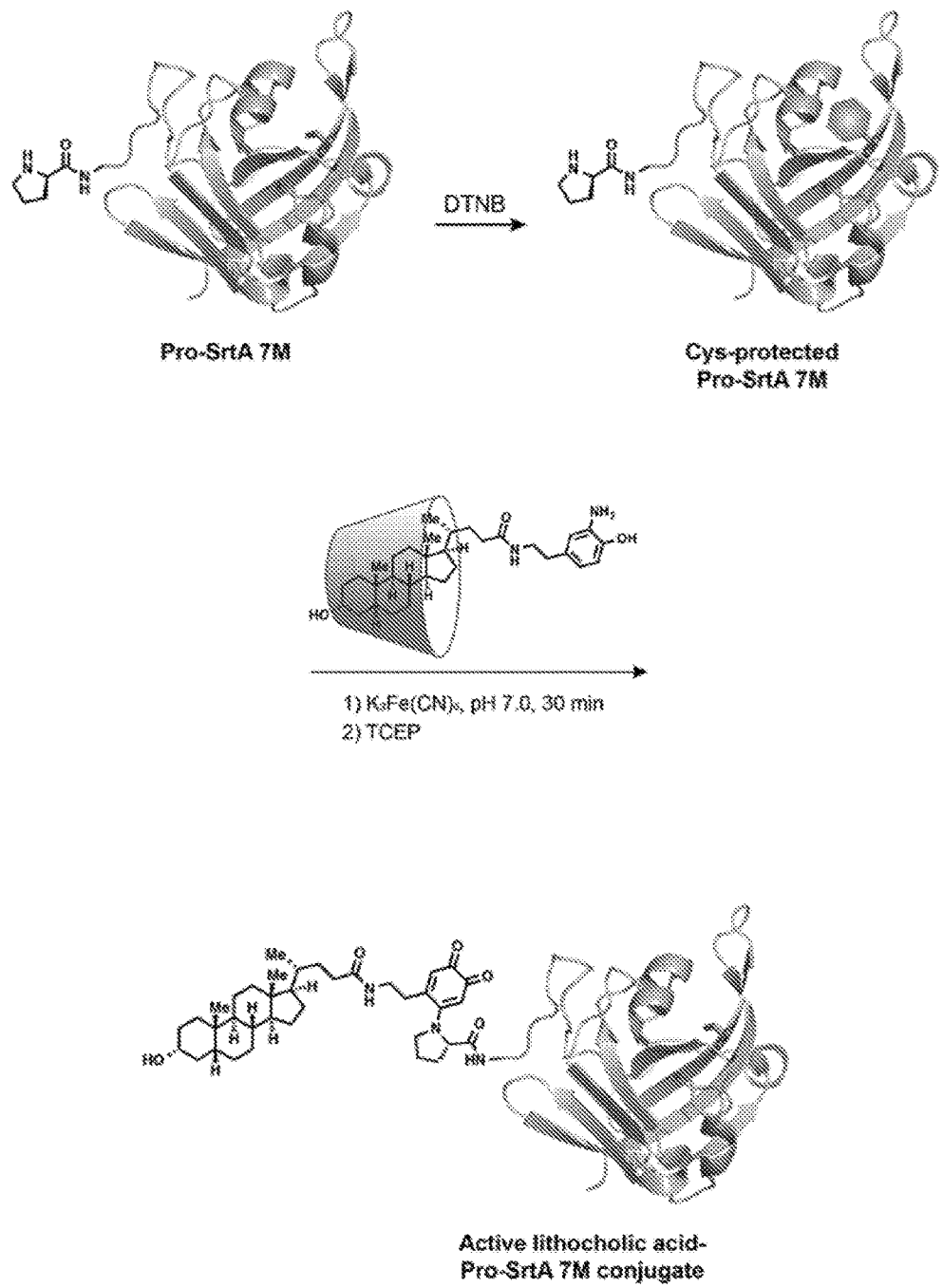
FIG. 17B shows the protection of sortase A (SrtA) cysteine with DTNB (hexagon structure) followed by N-terminal oxidative coupling with lithocholic acid-aminophenol and subsequent DTNB cleavage. β-cyclodextrin provides lithocholic acid solubility.
Figure 17C:
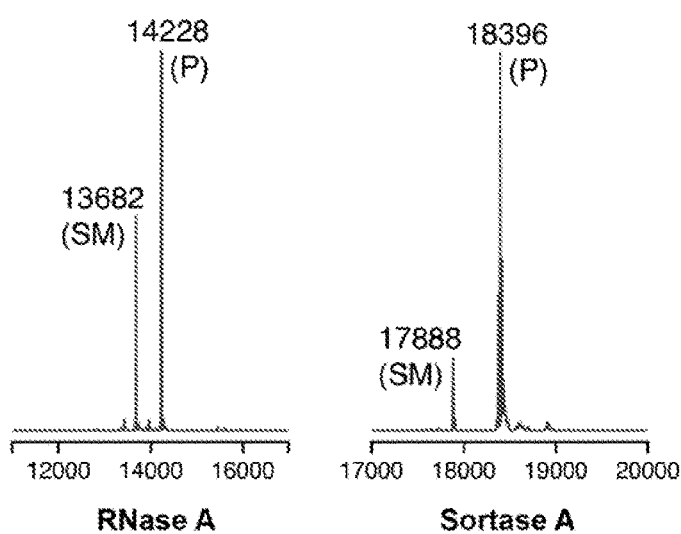
FIG. 17C shows mass spectrometry analysis of the conjugation reactions for RNase A and SrtA. SM: starting material, P: product.

Recycling of RNase A and sortase A is described herein. RNase A was modified using a 2-pyridinecarboxaldehyde-lithocholic acid construct, as shown in FIG. 2a. Sortase A was genetically engineered to hold an N-terminal proline enabling labeling with lithocholic acid through oxidative coupling after temporary protection of the catalytic site cysteine (FIG. 17B). The presence of excess (10 mM) ß-cyclodextrin provided sufficient solubility of the lithocholic acid molecular constructs (FIG. 17A and FIG. 17B). Mass spectrometry analysis showed excellent conversion for both conjugation reactions (FIG. 17C).

Figure 18A:
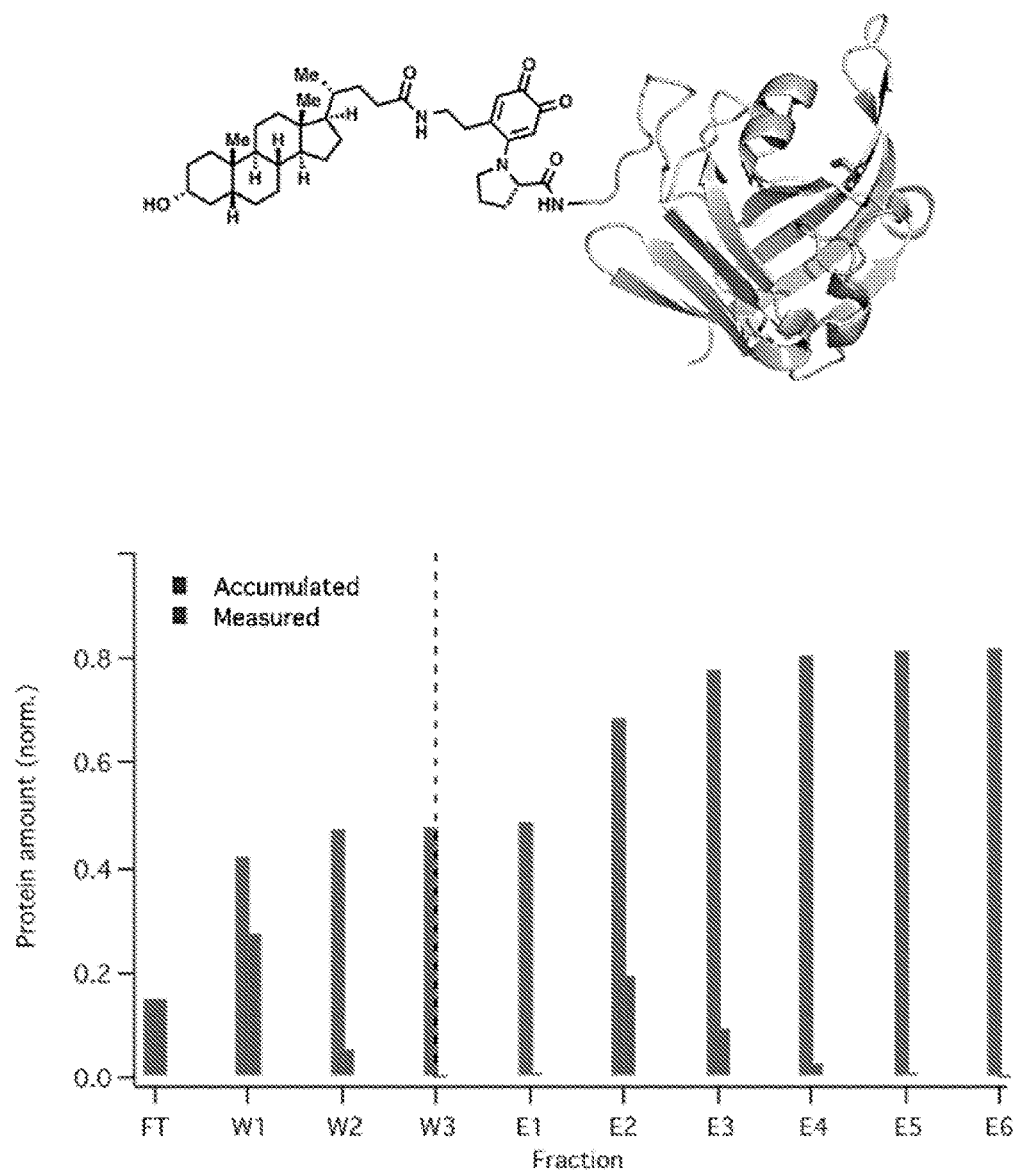
FIG. 18A shows the separation of modified from non-modified sortase A using β-cyclodextrin-functionalized resin for the recovery of the enzyme-lithocholic acid conjugate. Washing with buffer (W1-W3) eluted non-modified enzyme, whereas recovery of the sortase A-lithocholic acid conjugate was obtained by elution with β-cyclodextrin-containing buffer (E1-E5). Protein quantities were determined by UV-Vis absorbance at 280 nm.
Figure 18B:
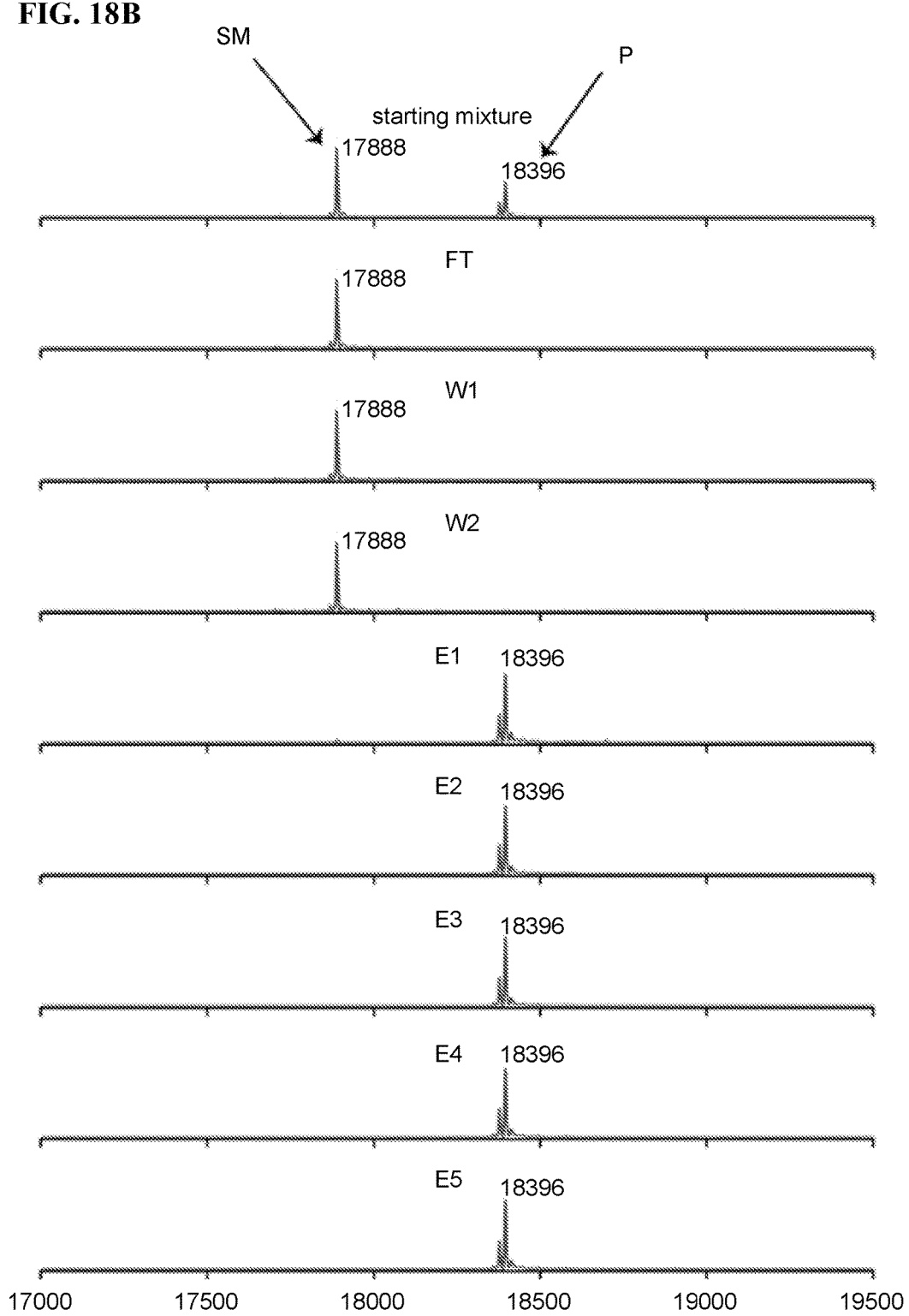
FIG. 18B shows mass spectrometry data of the elution fractions collected during recovery of the sortase A-lithocholic acid conjugate.

Separation and recycling was demonstrated by loading a mixture of modified and non-modified enzyme onto the ß-cyclodextrin-functionalized resin. The resin was then washed with buffered water to elute only the non-modified enzymes, while all modified enzyme was retained on the resin. Efficient release and recovery of the modified enzyme was achieved by eluting with ß-cyclodextrin-containing buffer. FIG. 18 shows separation and recovery of lithocholic acid-modified sortase A. In FIG. 18A the bars at the right in each set of data points denotes the measured protein amounts determined by UV-Vis absorbance at 280 nm. The bars at the left in each set of data points show the accumulated amounts along the x-axis. FT denotes the flow-through resulting from loading the enzyme mixture on the resin. By washing with buffer (W1-W3) a part of the enzyme elutes, which was identified as non-modified sortase A (SM) by mass spectrometry (FIG. 18B). Finally, the enzyme eluted with 1-cyclodextrin-containing buffer (E1-E5) was identified as the modified sortase A (P) (FIG. 18B).

Figure 19A:
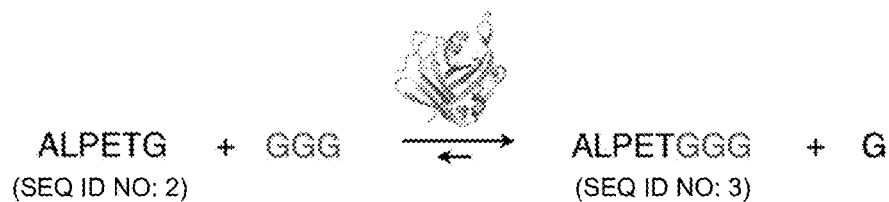
FIG. 19A shows the reaction scheme for sortase A-catalyzed transpeptidation of glycine oligomer (GGG) to the recognition sequence LPXTG, SEQ ID NO: 1, (ALPETG, SEQ ID NO: 2) between T and G.
Figure 19B:
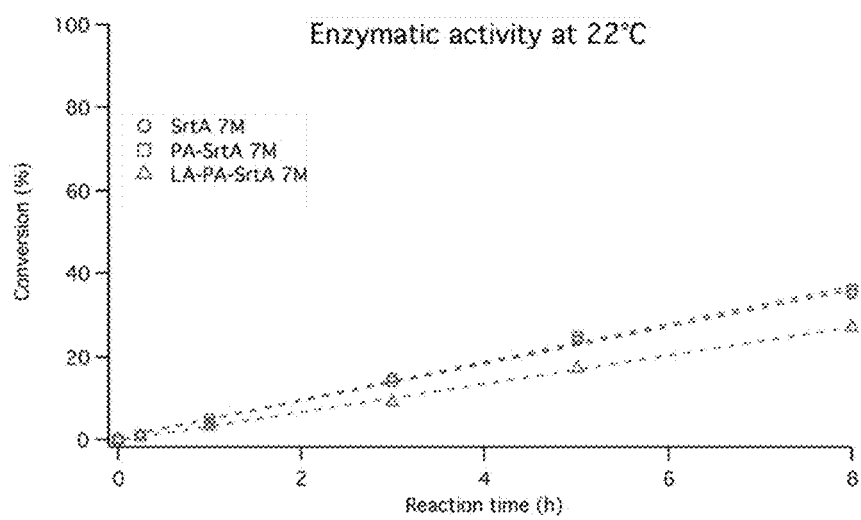
FIG. 19B shows a comparison of enzyme activities of modified (LA-PA-SrtA 7M) and non-modified (SrtA 7M and PA-SrtA 7M) sortase A variants. The lithocholic acid conjugate showed approximately 75% retained activity.
Figure 19C:
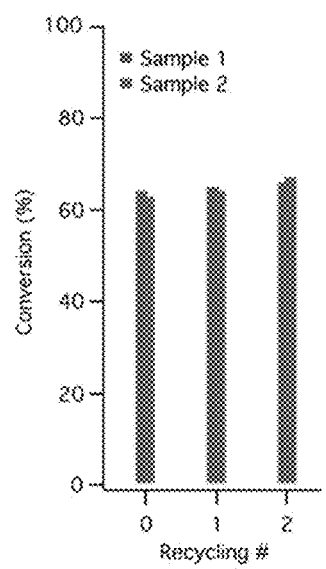
FIG. 19C shows enzyme activity measured over two rounds of recycling after 23 hours of reaction. Sample 1 and 2 are separate measurements of the same reaction sample.

The activity of sortase A was evaluated by its ability to catalyze the transpeptidation between two peptides at room temperature (FIG. 19A). Conversion to the ALPETGGG (SEQ ID NO: 3) product was quantified by mass spectrometry and compared to non-modified sortase A variants (SrtA 7M and PA-SrtA 7M; PA denotes the genetically engineered N-terminal proline). A time-course study revealed 75% retained activity of the sortase A-lithocholic acid conjugate compared to non-modified enzymes (FIG. 19B). After enzymatic reaction (23 hours at room temperature) and subsequent resin-mediated recovery the sortase A-lithocholic acid conjugate was successfully reused over two cycles without any decrease in activity (FIG. 19C).

Although the foregoing invention has been described in some detail by way of illustration and example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference. Where a conflict exists between the instant application and a reference provided herein, the instant application shall dominate.

What is claimed is:

1. A method for preparing a protein conjugate having a defined number of conjugate groups, the method comprising:
   i) forming a mixture comprising a cyclodextrin matrix material and a plurality of proteins, wherein:
   each protein in a first population of proteins in the plurality comprises a first number of handle moieties,
   each protein in a second population of proteins in the plurality comprises a second number of handle moieties,
   the first number of handle moieties and the second number of handle moieties are at least one and differ from one another, and
   the mixture is formed under conditions sufficient to bind the modified proteins to the cyclodextrin matrix material;
   ii) eluting the proteins from the cyclodextrin matrix material to obtain a first separated protein fraction and a second separated protein fraction, wherein:
   substantially all of the proteins in the first separated protein fraction comprise the first number of handle moieties, and
   substantially all of the proteins in the second separated protein fraction comprise the second number of handle moieties;
   iii) contacting the handle moieties with a conversion reagent under conditions sufficient to convert the handle moieties in the first separated protein fraction to reactive moieties; and
   iv) contacting the reactive moieties with a conjugation reagent under conditions sufficient to form a plurality of protein conjugates, wherein substantially all of the protein conjugates in the plurality have the same number of conjugate groups;
   thereby preparing the protein conjugate
   wherein the handle moieties comprise a structure according to Formula I:

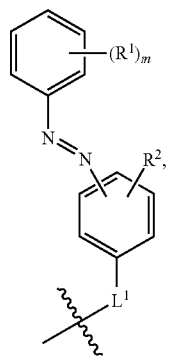

(I)

or a salt thereof, wherein m is an integer ranging from 0 to 5;

each $R^1$ is independently selected from the group consisting of —$OR^a$, —$N(R^a)_3$, —$SO_3H$, and —$CO_2H$;

$R^2$ is selected from the group consisting of H and —$OR^a$;

each $R^a$ is independently selected from the group consisting of H and $C_{1-6}$ alkyl; and $L^1$ is a linking moiety.

2. The method of claim 1, wherein the handle moiety comprises a structure according to Formula Ia:

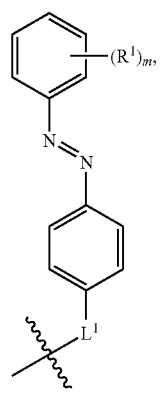

(Ia)

or a salt thereof, wherein m is an integer ranging from 0 to 5;

each $R^1$ is independently selected from the group consisting of —$OR^a$, —$N(R^a)_3$, —$SO_3H$, and —$CO_2H$, wherein each $R^a$ is independently selected from the group consisting of H and $C_{1-6}$ alkyl; and $L^1$ is a linking moiety.

3. The method of claim 1, wherein the linking moiety comprises a structure selected from the group consisting of:

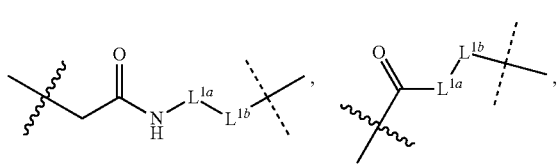

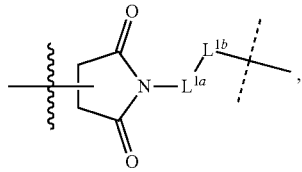

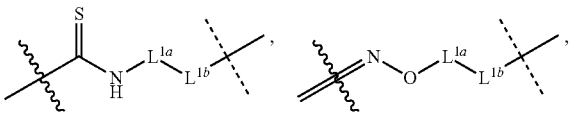

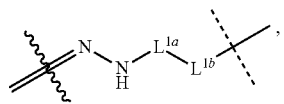

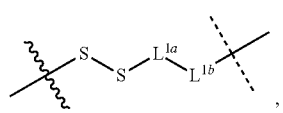

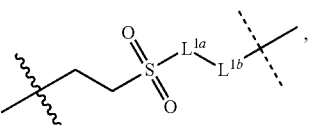

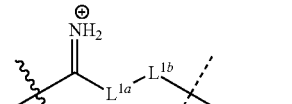

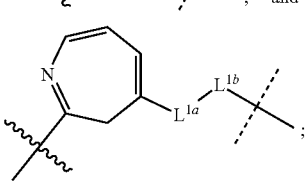

wherein $L^{1a}$ and $L^{1b}$ are independently selected from the group consisting of a bond, a divalent polymer moiety, and linear or branched, saturated or unsaturated $C_{1-30}$ alkyl; wherein one or more carbon atoms in the $C_{1-30}$ alkyl is optionally and independently replaced by O, S, NW; wherein two or more groupings of adjacent carbon atoms in the $C_{1-30}$ alkyl are optionally and independently replaced by —$NR^a(CO)$— or —$(CO)NR^a$—; and wherein two or more groupings of adjacent carbon atoms in the $C_{1-30}$ alkyl are optionally and independently replaced by a 4- to 8-membered, divalent carbocycle or a 4- to 8-membered, divalent heterocycle having one to four heteroatoms selected from the group consisting of O, S, and N; each $R^a$ is independently selected from the group consisting of H and $C_{1-6}$ alkyl; the wavy line represents the point of connection to the protein; and the dashed line represents the point of connection to the structure of Formula I.

4. The method of claim 1, wherein the reactive moiety comprises a structure according to Formula II:

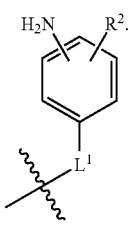

(II)

5. The method of claim 1, wherein the reactive moiety comprises a structure according to Formula IIa:

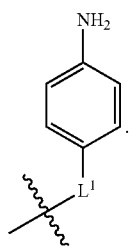

(IIa)

6. The method of claim 2, wherein the conjugation reagent comprises a structure according to Formula III:

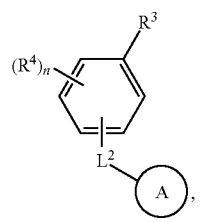

(III)

wherein:
$R^3$ is selected from the group consisting of —N($R^a$)$_2$ and —O$R^a$;
$R^4$ is selected from the group consisting of —O$R^a$, $C_{1-6}$ alkyl, —N($R^a$)$_2$, —N$_3$, and —NH(CO)$R^a$;
subscript n is an integer ranging from 0 to 3;
each $R^a$ is independently selected from the group consisting of H and $C_{1-6}$ alkyl;
$L^2$ is a linking moiety; and
A is a prosthetic moiety.

7. The method of claim 6, wherein the conjugation reagent comprises a structure according to Formula IIIa:

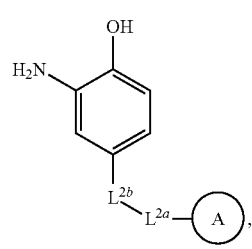

(IIIa)

wherein
$L^{2a}$ and $L^{2b}$ are independently selected from the group consisting of a bond, a divalent polymer moiety, and linear or branched, saturated or unsaturated $C_{1-30}$ alkyl; wherein one or more carbon atoms in the $C_{1-30}$ alkyl is optionally and independently replaced by O, S, NW; wherein two or more groupings of adjacent carbon atoms in the $C_{1-30}$ alkyl are optionally and independently replaced by —$NR^a$(CO)— or —(CO)$NR^a$—; and wherein two or more groupings of adjacent carbon atoms in the $C_{1-30}$ alkyl are optionally and independently replaced by a 4- to 8-membered, divalent carbocycle or a 4- to 8-membered, divalent heterocycle having one to four heteroatoms selected from the group consisting of O, S, and N; and
each $R^a$ is independently selected from the group consisting of H and $C_{1-6}$ alkyl.

8. The method of claim 1, wherein the contacting is conducted in the presence of an oxidizing agent, wherein the oxidizing agent is potassium ferricyanide.

9. The method of claim 6, wherein the protein conjugate comprises a structure according to Formula IV:

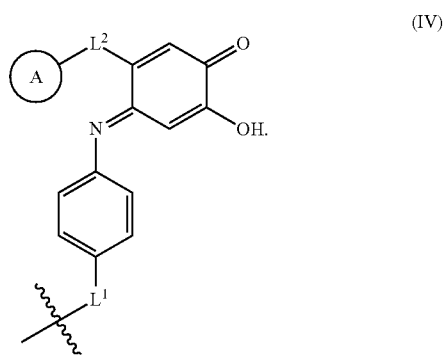

(IV)

10. The method of claim 1, wherein the cyclodextrin matrix material comprises a plurality of cyclodextrin moieties, wherein the cyclodextrin moiety comprises a structure according to Formula VI:

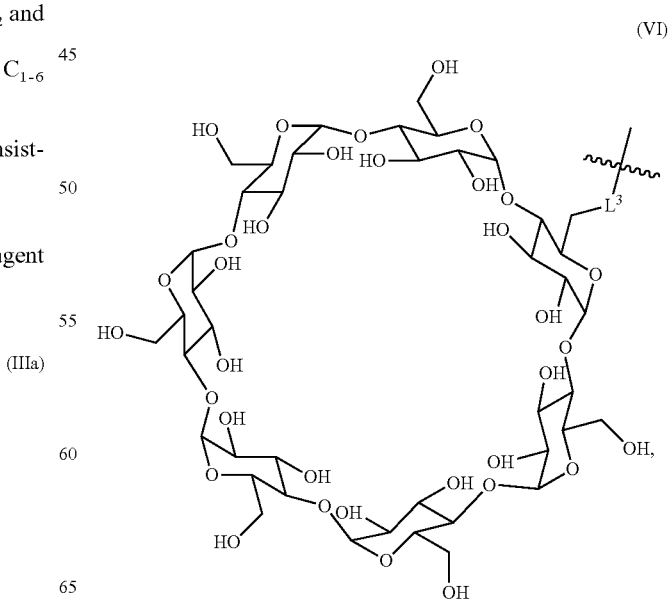

(VI)

wherein L³ is a linking moiety, and
the wavy line represents the connection point to the matrix material.

11. The method of claim 10, wherein the linking moiety comprises the grouping L$^{3a}$-L$^{3b}$-,
wherein L$^{3a}$ and L$^{3b}$ independently selected from the group consisting of a bond, a divalent polymer moiety, and linear or branched, saturated or unsaturated C$_{1-30}$ alkyl; wherein one or more carbon atoms in the C$_{1-30}$ alkyl is optionally and independently replaced by O, S, NW; wherein two or more groupings of adjacent carbon atoms in the C$_{1-30}$ alkyl are optionally and independently replaced by —NR$^a$(CO)— or —(CO)NR$^a$—; and wherein two or more groupings of adjacent carbon atoms in the C$_{1-30}$ alkyl are optionally and independently replaced by a 4- to 8-membered, divalent carbocycle or a 4- to 8-membered, divalent heterocycle having one to four heteroatoms selected from the group consisting of O, S, and N; and each R$^a$ is independently selected from the group consisting of H and C$_{1-6}$ alkyl.

12. The method of claim 10, wherein the cyclodextrin moiety comprises a structure according to Formula VIa:

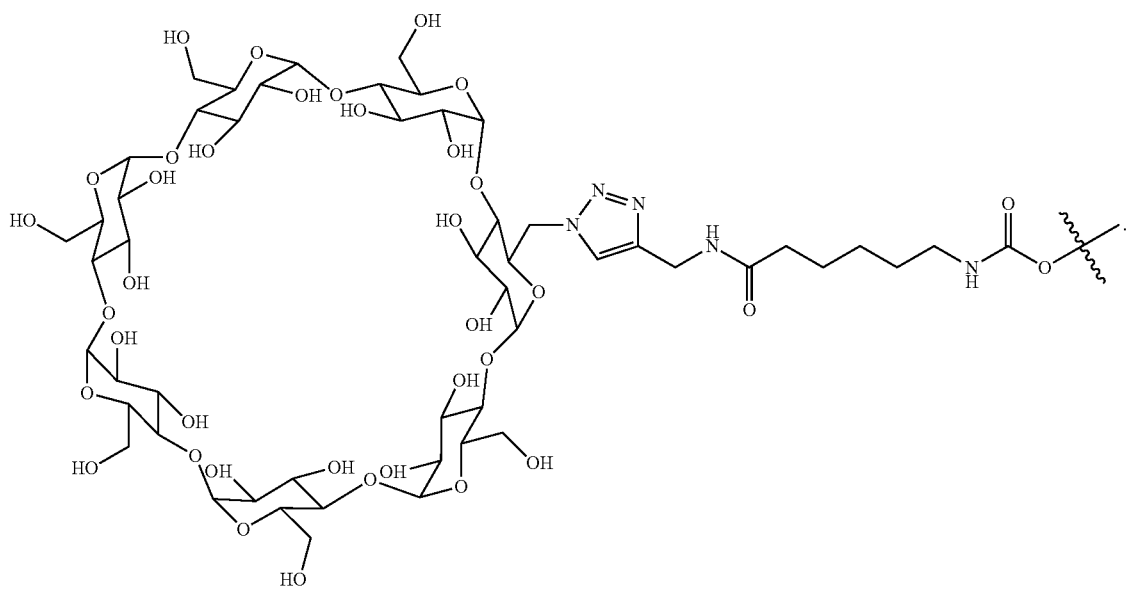

(VIa)

13. The method of claim 1, wherein the cyclodextrin matrix material comprises crosslinked agarose, crosslinked dextran, or a combination thereof.

14. The method of claim 1, wherein the protein is an enzyme.

* * * * *

SEQUENCE LISTING

```
<160> NUMBER OF SEQ ID NOS: 3

<210> SEQ ID NO 1
<211> LENGTH: 5
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<223> OTHER INFORMATION: sortase A recognition motif
<220> FEATURE:
<221> NAME/KEY: misc_feature
<222> LOCATION: (3)..(3)
<223> OTHER INFORMATION: Xaa is any amino acid

<400> SEQUENCE: 1

Leu Pro Xaa Thr Gly
1               5

<210> SEQ ID NO 2
<211> LENGTH: 6
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<223> OTHER INFORMATION: peptide 1

<400> SEQUENCE: 2

Ala Leu Pro Glu Thr Gly
1               5

<210> SEQ ID NO 3
<211> LENGTH: 8
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<223> OTHER INFORMATION: transpeptidation product of peptide 1

<400> SEQUENCE: 3

Ala Leu Pro Glu Thr Gly Gly Gly
1               5
```